(12) United States Patent
Rigatti et al.

(10) Patent No.: US 8,765,381 B2
(45) Date of Patent: *Jul. 1, 2014

(54) METHOD FOR PAIRWISE SEQUENCING OF TARGET POLYNUCLEOTIDES

(71) Applicant: Illumina Cambridge Limited, Essex (GB)

(72) Inventors: Roberto Rigatti, Essex (GB); Tobias William Barr Ost, Essex (GB)

(73) Assignee: Illumina Cambridge Limited, Nr Saffron Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,027

(22) Filed: Apr. 4, 2013

(65) Prior Publication Data

US 2013/0274115 A1    Oct. 17, 2013

Related U.S. Application Data

(63) Continuation of application No. 13/539,000, filed on Jun. 29, 2012, now Pat. No. 8,431,348, which is a continuation of application No. 13/330,117, filed on Dec. 19, 2011, now Pat. No. 8,236,505, which is a continuation of application No. 13/100,166, filed on May 3, 2011, now Pat. No. 8,105,784, which is a continuation of application No. 12/798,329, filed on Apr. 1, 2010, now Pat. No. 7,960,120, which is a continuation of application No. 11/973,321, filed on Oct. 5, 2007, now Pat. No. 7,754,429.

(60) Provisional application No. 60/898,910, filed on Feb. 1, 2007, provisional application No. 60/850,210, filed on Oct. 6, 2006.

(51) Int. Cl.
*C12Q 1/68* (2006.01)
*C12P 19/34* (2006.01)

(52) U.S. Cl.
CPC .................................. *C12Q 1/6874* (2013.01)
USPC ...................... 435/6.12; 435/91.1; 435/91.2

(58) Field of Classification Search
USPC ...................................... 435/6.12, 91.1, 91.2
See application file for complete search history.

(56) References Cited

U.S. PATENT DOCUMENTS 5,118,604 A    6/1992  Weissman et al.
5,302,509 A    4/1994  Cheeseman
(Continued)

FOREIGN PATENT DOCUMENTS

DE    10051564    1/2002
DE    10051564    8/2002
(Continued)

OTHER PUBLICATIONS

Adessi, et al., "Solid Phase DNA amplification: characterisation of primer attachment and amplification mechanisms", Nucleic Acids Research 28, 2000, 1-8.

(Continued)

*Primary Examiner* — Kenneth Horlick
(74) *Attorney, Agent, or Firm* — Brent C. Moore; Illumina, Inc.

(57) ABSTRACT

The invention relates to methods for pairwise sequencing of a double-stranded polynucleotide template, which methods result in the sequential determination of nucleotide sequences in two distinct and separate regions of the polynucleotide template. Using the methods of the invention it is possible to obtain two linked or paired reads of sequence information from each double-stranded template on a clustered array, rather than just a single sequencing read from one strand of the template.

16 Claims, 15 Drawing Sheets

(56) References Cited

U.S. PATENT DOCUMENTS

| | | | |
|---|---|---|---|
| 5,547,839 | A | 8/1996 | Dower et al. |
| 5,616,478 | A | 4/1997 | Chetverin |
| 5,629,158 | A | 5/1997 | Uhlen |
| 5,641,658 | A | 6/1997 | Adams et al. |
| 5,800,992 | A | 9/1998 | Fodor et al. |
| 5,837,466 | A | 11/1998 | Lane et al. |
| 5,922,574 | A | 7/1999 | Minter |
| 5,935,788 | A | 8/1999 | Burmer et al. |
| 5,976,802 | A | 11/1999 | Ansorge et al. |
| 6,060,288 | A | 5/2000 | Adams et al. |
| 6,090,592 | A | 7/2000 | Adams et al. |
| 6,107,023 | A | 8/2000 | Reyes et al. |
| 6,251,610 | B1 | 6/2001 | Gupte et al. |
| 6,322,971 | B1 | 11/2001 | Chetverin et al. |
| 6,326,489 | B1 | 12/2001 | Church et al. |
| 6,361,947 | B1 | 3/2002 | Dong et al. |
| 6,511,803 | B1 | 1/2003 | Church et al. |
| 7,115,400 | B1 | 10/2006 | Adessi et al. |
| 2002/0055100 | A1 | 5/2002 | Kawashima et al. |
| 2002/0061532 | A1 | 5/2002 | Adams et al. |
| 2002/0081591 | A1 | 6/2002 | Lukhtanov et al. |
| 2002/0098499 | A1 | 7/2002 | Asp et al. |
| 2003/0022207 | A1 | 1/2003 | Balasubramanian et al. |
| 2003/0082576 | A1 | 5/2003 | Jones et al. |
| 2003/0108867 | A1 | 6/2003 | Chee |
| 2004/0002090 | A1 | 1/2004 | Mayer et al. |
| 2004/0096853 | A1 | 5/2004 | Mayer |
| 2004/0126765 | A1 | 7/2004 | Adams |
| 2005/0100900 | A1 | 5/2005 | Kawashima et al. |
| 2006/0024681 | A1 | 2/2006 | Smith et al. |
| 2006/0134633 | A1 | 6/2006 | Chen et al. |
| 2006/0292611 | A1 | 12/2006 | Berka et al. |
| 2007/0128624 | A1 | 6/2007 | Gormley et al. |
| 2008/0009420 | A1 | 1/2008 | Schroth et al. |
| 2009/0093378 | A1 | 4/2009 | Bignell et al. |

FOREIGN PATENT DOCUMENTS

| | | |
|---|---|---|
| EP | 0 224 126 | 6/1987 |
| EP | 0 356 021 | 2/1990 |
| EP | 0 374 665 | 6/1990 |
| EP | 0 438 292 | 7/1991 |
| EP | 0 201 184 | 12/1992 |
| EP | 0 534 858 | 3/1993 |
| EP | 0 665 293 | 8/1995 |
| EP | 0 763 135 | 3/1997 |
| EP | 1256632 | 11/2002 |
| EP | 1 591 541 | 11/2005 |
| EP | 1634963 | 3/2006 |
| EP | 1 647 602 | 4/2006 |
| EP | 2 032 686 | 3/2009 |
| GB | 0205153.0 | 4/2002 |
| GB | 2412170 | 9/2005 |
| GB | 0522310.2 | 12/2005 |
| WO | 89/01050 | 2/1989 |
| WO | 89/09282 | 10/1989 |
| WO | 92/10587 | 6/1992 |
| WO | 93/04199 | 3/1993 |
| WO | 94/02634 | 2/1994 |
| WO | 95/33073 | 12/1995 |
| WO | 96/04404 | 2/1996 |
| WO | 96/32504 | 10/1996 |
| WO | 98/36094 | 8/1998 |
| WO | 98/44151 | 10/1998 |
| WO | 98/44152 | 10/1998 |
| WO | 00/18957 | 4/2000 |
| WO | 00/75374 | 12/2000 |
| WO | 01/49882 | 7/2001 |
| WO | 01/79553 | 10/2001 |
| WO | 02/46456 | 6/2002 |
| WO | 03/056030 | 7/2003 |
| WO | 03/074734 | 9/2003 |
| WO | 2004/070005 | 8/2004 |
| WO | 2004/072294 | 8/2004 |
| WO | 2005/003375 | 1/2005 |
| WO | 2005/040425 | 5/2005 |
| WO | 2005/042781 | 5/2005 |
| WO | 2005/060345 | 7/2005 |
| WO | 2005/068656 | 7/2005 |
| WO | 2005/093094 | 10/2005 |
| WO | 2006040104 | 4/2006 |
| WO | 2006/110855 | 10/2006 |
| WO | 2006/135342 | 12/2006 |
| WO | 2007/010251 | 1/2007 |
| WO | 2007/010252 | 1/2007 |
| WO | 2007/010263 | 1/2007 |
| WO | 2007010252 | 1/2007 |
| WO | 2007/052006 | 5/2007 |
| WO | 2007/076726 | 7/2007 |
| WO | 2007/091077 | 8/2007 |
| WO | 2007091077 | 8/2007 |
| WO | 2007/107710 | 9/2007 |
| WO | 2007/111937 | 10/2007 |
| WO | 2008/002502 | 1/2008 |

OTHER PUBLICATIONS

Bennett, et al., "Toward the $1000 Human Genome", Pharmacogenomics, Ashley Productions GB vol. 6 No. 4, 2005, 373-382.

Braslavsky, et al., "Sequence information can be obtained from single DNA molecules", PNAS, 100(7), 2003, 3960-3964.

Cheng, et al., "Chip PCR II Investigation of different PCR amplification systems in microfabricated silicon-glass chips", Nucleic Acids Research 24, 1996, 380-385.

Dubiley, et al., "Polymorphism analysis and gene detection by minisequencing on an array of gel-immobilized primers", Nucleic Acids Research 27, 1999, 1-6.

Frommer, et al., "A genomic sequencing protocol that yields a positive display of 5-methylcytosine residues in individual DNA strands", Proc Natl Acad Sci USA, 89 (5):1827-1831 (1992), 1992, 1827-1831.

Fu, et al., "Sequencing Double-stranded DNA by Strand Displacement", Nucleic Acids Research vol. 25 No. 3, 1997, 677-679.

Fullwood, Melissa J. et al., "Next-generation DNA sequencing of paired-end tags (PET) for transcriptome and genome analyses", Genome Research, vol. 19, No. 4, Apr. 1, 2009, 521-532.

Helfman, et al., "Identification of clones that encode chicken tropomyosin by direct immunological screening of a cDNA expression library", PNAS US 80, 1983, 31-35.

Kaderali, et al., Nucleic Acids Research, 31(6), 2003, 1796-1802.

Kalisch, et al., "Covalently linked sequencing primer linkers (splinkers) for sequence analysis of restriction fragments", Gene 44, 1986, 263-270.

Kimmel, et al., "Preparation of cDNA and the Generation of cDNA Libraries: Overview", Methods in Enzymology 152, 1987, 307-316.

Kinzler, et al., "Whole genome PCR: application to the identification of sequences bound by gene regulatory proteins", Nucleic Acids Research, 17(10), 1989, 3645-3653.

Lucito, et al., "Genetic analysis using genomic representations", PNAS, 95, 1998, 4487-4492.

Mardis, "next-generation DNA sequencing methods", Annual Review of Genomics and Human Genetics, Sep. 2008, 387-402.

Margulies, Marcel et al., "Genome Sequencing in microfabricated high-density picolitre reactors", Nature, vol. 437 No. 7057, Jul. 31, 2005, 376-380.

Matsunaga, et al., "Selecting and amplifying one fragement from a DNA fragment mixture by polyermerase chain reaction with a pair of selective primers", Electrophoresis, vol. 17, 1996, 1833-1840.

Ng, et al., "Multiplex sequencing of paired-end ditags (MS-PET): a strategy for the ultra-high-throughput analysis of transcriptomes and genomes", Nucleic Acids research 2006—vol. 34 No. 12, Jul. 2006, E84.

O'Meara, et al., "SNP typing by apyrase-mediated allele-specific primer extension on DNA microarrays", NAR, 30, 2002, 1-8.

Oroskar, et al., "Detection of immobilized amplicons by ELISA-like techniques", Clinical Chemistry 42, 1996, 1547-1555.

(56) References Cited

OTHER PUBLICATIONS

Roach, et al., "Pairwise end sequencing: A unified approach to genomic mapping and sequencing", Genomics 26, 1995, 345-353.

Ronaghi, et al., "Analyses of Secondary Structures in DNA by Pyrosequencing", Anal. Biochem. Feb. 1, 1999;267 (1):65-71, Feb. 1, 1999, 65-71.

Saiki, et al., "Analysis of enzymatically amplified . . . —globin and HLA-DQ . . . DNA with allele-specific oligonucleotide probes", Nature 324, 1986, 163-166.

Saiki, et al., "Primer-Directed Enzymatic Amplification of DNA with a Thermostable DNA Polymerase", Science 239, 1988, 487-491.

San Luis, et al., "Analysis of a gene (vch) encoding hemolysin isolated and sequenced from *Vibrio campbellii*", Journal of general and Applied Microbiology; vol. 52; No. 6, Dec. 2006, 303-313 (307-308?).

Sanger, et al., "Cloning in Single-Stranded Bacteriophage as an Aid to Rapid DNA Sequencing", Mol Biologiy 143, 1980, 161-178.

Sarkar, et al., "Restriction-site PCR: A direct method of unknown sequence retrieval adjacent to a known locus by using universal primers", PCR Methods and Applications, 1993, 2:318-322.

Shapero, et al., "SNP Genotyping by multiplexed solid-phase amplification and fluorescent minisequencing", Genome Research vol. 11 No. 11, 2001, 1926-1934.

Shendure, et al., "Accurate Multiplex Polony Sequencing of an Evolved Bacterial Genome", Science, vol. 309 No. 5741, 2005, 1728-1732.

Shi, "Enablling large-scale Pharmacogenetic studies by high-throughput mutation detection and genotyping technologies", Clinical Chemistry vol. 47 No. 2, 2000, 164-172.

Solexa, "Solexa Application Note: DNA Sequencing", 2006.

Sterky, et al., "Direct sequencing of bacterial artificial chromosomes [bacS] prokaryotic genomes by biotin capture PCR", Journal of Biotechnology, vol. 60, 1998, 119-129.

Strick, et al., "Stress-Induced Structural Transistions of DNA and Proteins", Annu Rev. Biophys. Biomol. Struct. 29, 2000, 523-543.

Velculescu, et al., "Serial analysis of gene expression", Science, 270, 1995, 484-487.

Warren, Rene et al., "Assembling Millions of short DNA sequences using SSAKE", Bioinformatics (Oxford) vol. 23 No. 4, 2007, 500-501.

Westin, et al., "Anchored multiplex amplification on a microelectric chip array", Nature Biotechnology 18, 2000, 199-204.

Wiemann, et al., "Doublex Fluorescent DNA sequencing: two independent sequences obtained simultaneously in one reaction with internal labeling and unlabeled primers", Analytical Biochemistry US, 1996, 166-174.

Beaucage, Serge L. , "Strategies in the Preparation of DNA Oligonucleotide Arrays for Diagnostic Applications", Curren Medicinal Chemistry, 2001, 1213-1244.

Szybalski, Waclaw , "From the double-helix to novel approaches to the sequencing of large genomes", Gene, 135, Elesvier Science Publishers B.V., 1993, 279-290.

Voss, et al., "Efficient low redundancy large-scale DNA sequencing at EMBL", Journal of Biotechnology 41, Elsevier Science B.V., 1995, 121-129.

Zhou, Guo-Hua et al., "Multiplex SNP typing by bioluminometric assay coupled with terminator incorporation (BATI)", Nucleic Acids Research, vol. 33, No. 15, Sep. 1, 2005, e133.

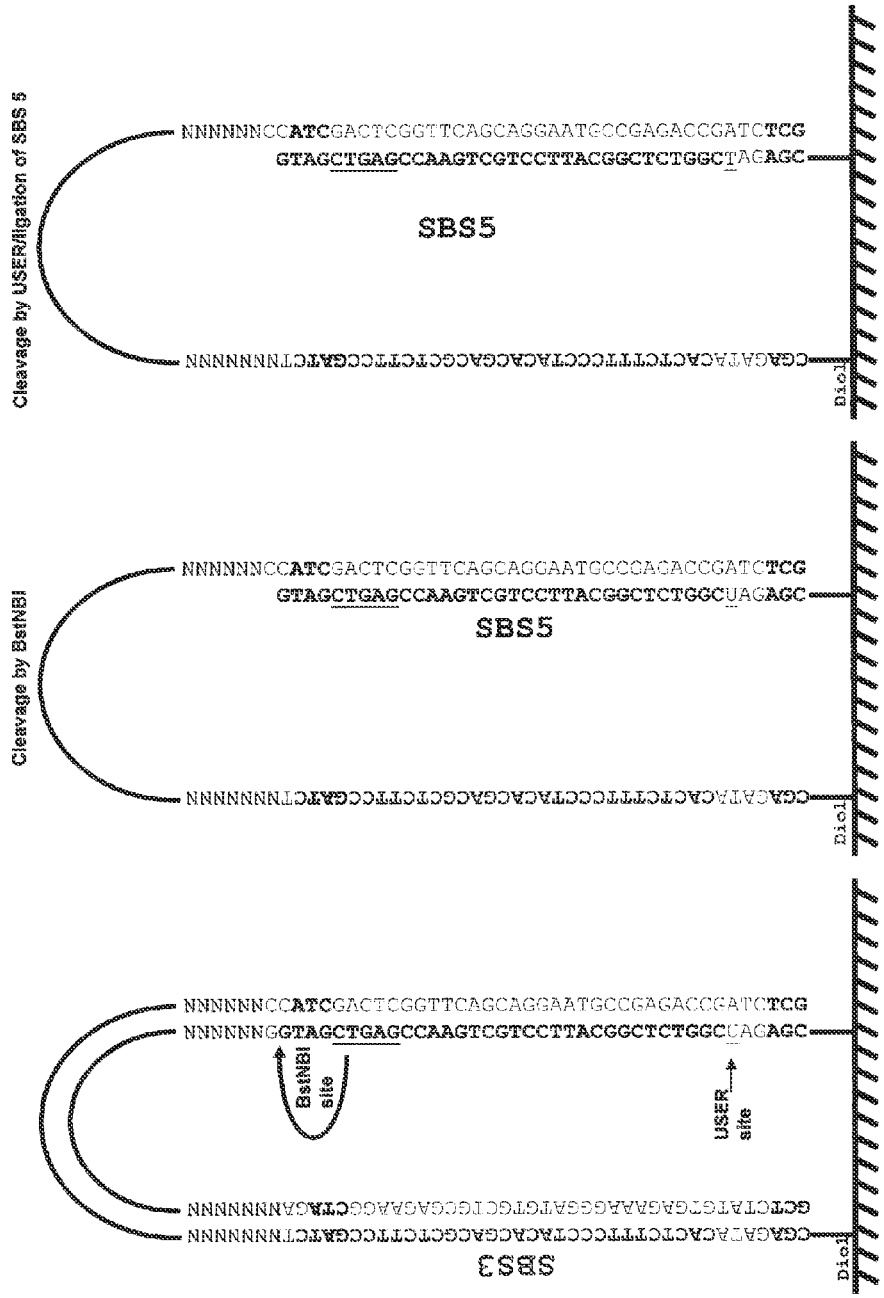

Paired-end sequencing: DNA construct for cluster growth

TTTTTTTTTTTTAATGATACGGCGACCACCGAGATACACTCTTTCCCTACACGACGCTCTTCCGATCTCAG
TGGATGCATGGCTGCGAGCTGGGGCCCGACAGGCGCTTCCTCCCGCGGGTATGAACAGTTCGCCTACGAC
GGCAAGGATTATCTCACCCTGAATGATCCATCGACTCGGTTCAGCAGGAATGCCGAGACCGATCTCGTA
TGCCCGTCTTCTGCTTGAAAAAAAA

TTTTTTTTTTTAATGATACGGCGACCACCGA = 10T-P5

ACACTCTTTCCCTACACGACGCTCTTCCGATC = SBS3

GACTC = reverse complement of the recognition sequence for N.BstNB I

ATCTCGTATGCCGTCTTCTGCTTGAAAAAAAA = reverse complement of 10T-P7-GAU

CATCGACTCGGTTCAGCAGGAATGCCGAGACCGA = reverse complement of SBS5
ligation primer

Figure 6

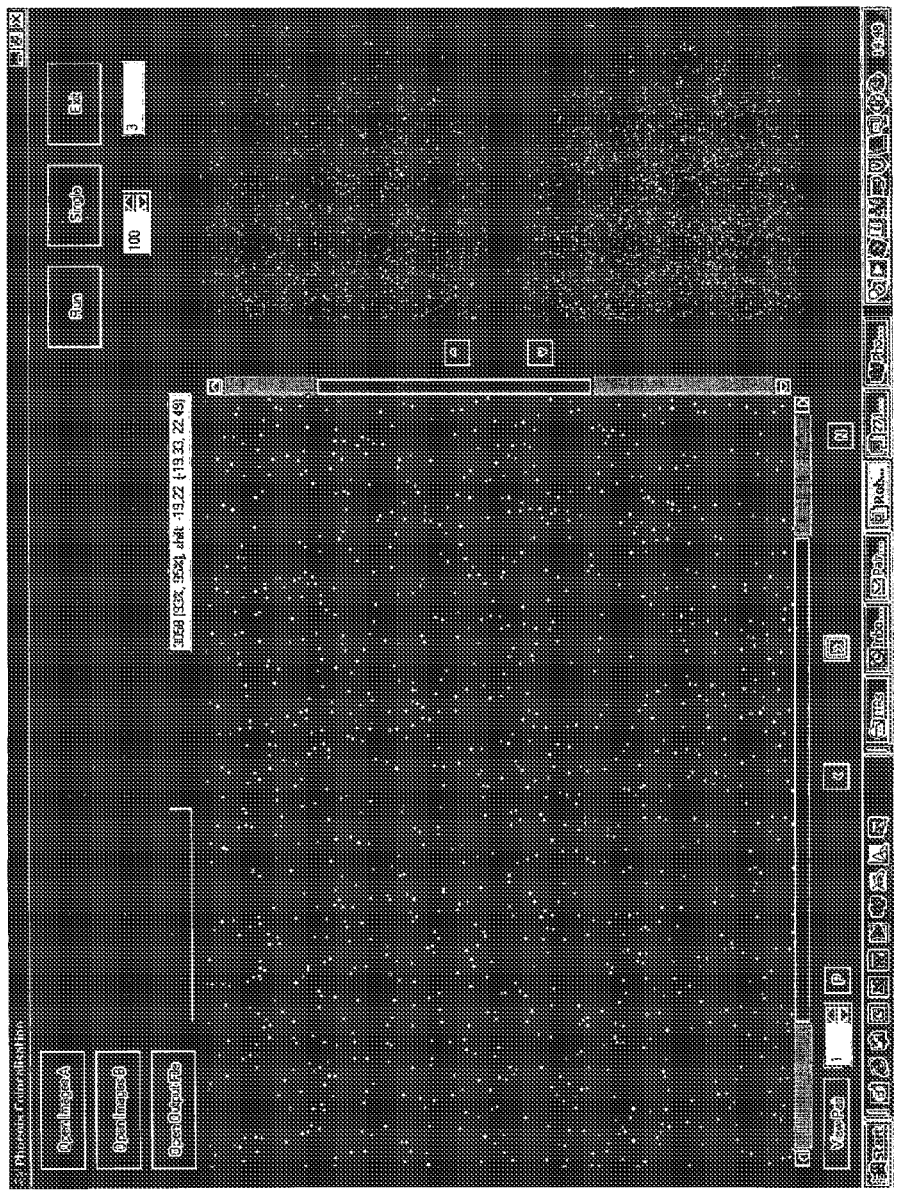
Figure 7: Two cycles of SBS using immobilised sequencing primer

Comparison Between Two Paired Reads of a library of BAC Fragments

| BAC CT413<br>FC 3433 Lane 3 | Read 1<br>(25 cyc) | Read 2<br>(25 cyc) |
|---|---|---|
| Ave.# / tile | 8572 | 8208 |
| % PF Clusters | 77.5 | 77.8 |
| Ave.% align (PF) | 95 | 95 |
| Ave. Error rate (Phagealign) | 3.24 | 4.41 |
| Ave. Error rate (ELAND) | 0.31 | 1.12 |
| Phasing | 0.69 | 0.85 |
| Prephasing | 0.21 | 0.34 |

← *E. Coli* contamination

Figure 8

SEQUENCE LISTING

```
<160> NUMBER OF SEQ ID NOS: 33

<210> SEQ ID NO 1
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(11)
<223> OTHER INFORMATION: Nucleotides at positions 10 and 11 linked by
      diol

<400> SEQUENCE: 1
tttttttttt aatgatacgg cgaccaccga                                           30

<210> SEQ ID NO 2
<211> LENGTH: 34
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (34)..(34)
<223> OTHER INFORMATION: n is 2-deoxyuridine

<400> SEQUENCE: 2
tttttttttt caagcagaag acggcatacg agan                                      34

<210> SEQ ID NO 3
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(10)
<223> OTHER INFORMATION: n is a, c, g, or t
```

<400> SEQUENCE: 3 gagtcnnnnn                                                                10

<210> SEQ ID NO 4
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(10)
<223> OTHER INFORMATION: n is a, c, g, or t

<400> SEQUENCE: 4 ctcagnnnnn                                                                10

<210> SEQ ID NO 5
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 5
gtagctgagc caagtcgtcc ttacggctct ggct                                      34

<210> SEQ ID NO 6
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 6
acactctttc cctacacgac gctcttccga tc                                        32

<210> SEQ ID NO 7
<211> LENGTH: 33
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (32)..(33)
<223> OTHER INFORMATION: Nucleotides at positions 32 and 33 linked by a
      phosphorothioate bond

<400> SEQUENCE: 7
acactctttc cctacacgac gctcttccga tct                                       33

<210> SEQ ID NO 8
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 8
gatcggaaga gcggttcagc aggaatgccg ag                                        32

<210> SEQ ID NO 9
<211> LENGTH: 61
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<222> LOCATION: (60)..(61)
<223> OTHER INFORMATION: Nucleotides in positions 60 and 61 linked by a
      phosphorothioate bond

<400> SEQUENCE: 9
caagcagaag acggcatacg agatcggtct cggcattcct gctgaaccgc tcttccgatc      60
t                                                                      61

<210> SEQ ID NO 10
<211> LENGTH: 204
<212> TYPE: DNA
<213> ORGANISM: Homo sapiens

<400> SEQUENCE: 10
aatgatacgg cgaccaccga gatctacact ctttccctac acgacgctct tccgatctac      60
tgatttcatt gcagccaaag gcaaactttg gctgcatcgt tttacagtcg ccataagcct     120
ttcctctgtt aaaccgcctt ctgagatcgg aagagcggtt cagcaggaat gccgagaccg     180
atctcgtatg ccgtcttctg cttg                                            204

<210> SEQ ID NO 11
<211> LENGTH: 214
<212> TYPE: DNA
<213> ORGANISM: Homo sapiens

<400> SEQUENCE: 11
aatgatacgg cgaccaccga gatctacact ctttccctac acgacgctct tccgatctat      60
caatattgtg aaaatgacca tactgccaaa aaaaaactac aaattcaatg caattttcat     120
caaaatacca tcatcattct tcacaatatt gatagatcgg aagagcggtt cagcaggaat     180
gccgagaccg atctcgtatg ccgtcttctg cttg                                 214

<210> SEQ ID NO 12
<211> LENGTH: 214
<212> TYPE: DNA
<213> ORGANISM: Homo sapiens

<400> SEQUENCE: 12
aatgatacgg cgaccaccga gatctacact ctttccctac acgacgctct tccgatctat      60
caatattgtg aaaatgacca tactgccaaa aaaaaactac aaattcaatg caattttcat     120
caaaatacca tcatcattct tcacaatatt gatagatcgg aagagcggtt cagcaggaat     180
gccgagaccg atctcgtatg ccgtcttctg cttg                                 214

<210> SEQ ID NO 13
<211> LENGTH: 215
<212> TYPE: DNA
<213> ORGANISM: Homo sapiens

<400> SEQUENCE: 13
aatgatacgg cgaccaccga gatctacact ctttccctac acgacgctct tccgatctct      60
cactcctggc agagggacgt gtgactagcc atgggcccct aggtctccag ttcctgggta     120
gcttgtattt ttgaacatct cctgtatatt agttagatcg gaagagcggt tcagcaggaa     180
tgccgagacc gatctcgtat gccgtcttct gcttg                                215
```

<210> SEQ ID NO 14
<211> LENGTH: 147
<212> TYPE: DNA
<213> ORGANISM: Homo sapiens

<400> SEQUENCE: 14
aatgatacgg cgaccaccga gatctacact ctttccctac acgacgctct tccgatctag      60
tgtagttgag atctgcctta gcagcaagat cggaagagcg gttcagcagg aatgccgaga     120
ccgatctcgt atgccgtctt ctgcttg                                          147

<210> SEQ ID NO 15
<211> LENGTH: 183
<212> TYPE: DNA
<213> ORGANISM: Homo sapiens

<400> SEQUENCE: 15
aatgatacgg cgaccaccga gatctacact ctttccctac acgacgctct tccgatctaa      60
cacatttcaa agtttggggc cctcctcctc cccaaaaaac aaaccacaaa aaacaaacaa     120
aaagatcgga gagcggttc agcaggaatg ccgagaccga tctcgtatgc cgtcttctgc      180
ttg                                                                   183

<210> SEQ ID NO 16
<211> LENGTH: 170
<212> TYPE: DNA
<213> ORGANISM: Homo sapiens

<400> SEQUENCE: 16
ggcgaccacc gagatctaca ctctttccct acacgacgct cttccgatct gaatgccttt      60
tatagcattt aattttttcct aagtataatt accaaataaa aattgtataa gatcggaaga    120
gcggttcagc aggaatgccg agaccgatct cgtatgccgt cttctgcttg                170

<210> SEQ ID NO 17
<211> LENGTH: 180
<212> TYPE: DNA
<213> ORGANISM: Homo sapiens

<400> SEQUENCE: 17
aatgatacgg cgaccaccga gatctacact ctttccctac acgacgctct tccgatcttg      60
ggcccgggag gagtttgccg gggaggagtg ggtttggaat cggggttaaa ggaaagagaa     120
gatcggaaga gcggttcagc aggaatgccg agaccgatct cgtatgccgt cttctgcttg     180

<210> SEQ ID NO 18
<211> LENGTH: 190
<212> TYPE: DNA
<213> ORGANISM: Homo sapiens

<400> SEQUENCE: 18
tgatacggcg accaccgaga tctacactct ttccctacac gacgctcttc cgatctaaga      60
tctatttcaa atggactgta gatctaagta taaaggtaa gagaataatt attctagaaa     120
gtaaatgtaa gatcggaaga gcggttcagc aggaatgccg agaccgatct cgtatgccgt     180
cttctgcttg                                                            190

<210> SEQ ID NO 19
<211> LENGTH: 192
<212> TYPE: DNA
<213> ORGANISM: Homo sapiens

<400> SEQUENCE: 19

```
aatgatacgg cgaccaccag atctacactc tttccctaca cgacgctctt ccgatctggg      60
aggccaaggt gggtggatca cctgagatca ggagttcgag accagctggc caacatgatg     120
aaactctgtc tagatcggaa gagcggttca gcaggaatgc cgagaccgat ctcgtatgcc     180
gtcttctgct tg                                                         192
```

```
<210> SEQ ID NO 20
<211> LENGTH: 185
<212> TYPE: DNA
<213> ORGANISM: Homo sapiens
```

<400> SEQUENCE: 20

```
aatgatacgg cgaccaccga gatctacact ctttccctac acgacgctct tccgatcttg      60
accattgtaa ccattaatgt agactgcaat gatatgcact atttcaaacc ttttttaaga    120
ctctagatcg aagagcggt tcagcaggaa tgccgagacc gatctcgtat gccgtcttct     180
gcttg                                                                 185
```

```
<210> SEQ ID NO 21
<211> LENGTH: 199
<212> TYPE: DNA
<213> ORGANISM: Homo sapiens
```

<400> SEQUENCE: 21

```
aatgatacgg cgaccaccga gatctacact ctttccctac acgacgctct tccgatctct      60
ttgaagagct ggcagtagaa gataaacagg ctggggaaga agagaaagtg ctcaaggaga    120
aggagcagca gcagcagcag atcggaagag cggttcagca ggaatgccga gaccgatctc    180
gtatgccgtc ttctgcttg                                                 199
```

```
<210> SEQ ID NO 22
<211> LENGTH: 212
<212> TYPE: DNA
<213> ORGANISM: Homo sapiens
```

<400> SEQUENCE: 22

```
aatgatacgg cgaccaccga gatctacact ctttccctac acgacgctct tccgatctag      60
tattcaacaa gtctgtcttt tccaagtgtc tttaaagacc agaaatacct gttttttaaca    120
cacagggttg caaaattcag aggagattgg cagatcggaa gagcggttca gcaggaatgc    180
cgagaccgat ctcgtatgcc gtcttctgct tg                                   212
```

```
<210> SEQ ID NO 23
<211> LENGTH: 247
<212> TYPE: DNA
<213> ORGANISM: Homo sapiens
```

<400> SEQUENCE: 23

```
aatgatacgg cgaccaccga gatctacact ctttccctac acgacgctct tccgatctct      60
tgagatgagt gatgacggcg cgctggaagt tgctcgtcgc gctcgcggta cgccgcgcat    120
tgccaaccgt ctgctgcgtc gagtgcgtga tttcgccgaa gtgaagcacg atggcaccat    180
ctcaagagat cggaagagcg gttcagcagg aatgccgaga ccgatctcgt atgccgtctt    240
ctgcttg                                                              247
```

```
<210> SEQ ID NO 24
<211> LENGTH: 202
```

<212> TYPE: DNA
<213> ORGANISM: Homo sapiens

<400> SEQUENCE: 24
aatgatacgg cgaccaccga gatctacact ctttccctac acgacgctct tccgatctgg       60
ggttggtgga acccagatgc ctcccaggat tggtgggccc tgtggcactt gtacctgctg      120
ttgctgttgc tgctgctgct gagatcggaa gagcggttca gcaggaatgc cgagaccgat      180
ctcgtatgcc gtcttctgct tg                                               202

<210> SEQ ID NO 25
<211> LENGTH: 166
<212> TYPE: DNA
<213> ORGANISM: Homo sapiens

<400> SEQUENCE: 25
aatgatacgg cgaccaccga gatctacact ctttccctac acgacgctct tccgatctat       60
gataaggagc aggtttacag atcataagtg caaaagcggg cgagaagatc ggaagagcgg      120
ttcagcagga atgccgagac cgatctcgta tgccgtcttc tgcttg                     166

<210> SEQ ID NO 26
<211> LENGTH: 147
<212> TYPE: DNA
<213> ORGANISM: Homo sapiens

<400> SEQUENCE: 26
gatacggcga ccaccgagat ctacactctt ccctacacg acgctcttcc gatctctgat       60
actgttgtaa ccacccaatt ggttcaagat cggaagagcg gttcagcagg aatgccgaga      120
ccgatctcgt atgccgtctt ctgcttg                                          147

<210> SEQ ID NO 27
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 27
aatgatacgg cgaccaccga gatctacact ctttccctac acgacgctct tccgatct         58

<210> SEQ ID NO 28
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 28
agatcggaag agcggttcag caggaatgcc gagaccgatc tcgtatgccg tcttctgctt       60
g                                                                       61

<210> SEQ ID NO 29
<211> LENGTH: 31
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: n is 2-deoxyuridine -continued

```
<400> SEQUENCE: 29
tttttttttn caagcagaag acggcatacg a                              31

<210> SEQ ID NO 30
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 30
tttttttttt aatgatacgg cgaccaccga                                30

<210> SEQ ID NO 31
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 31
cggtctcggc attcctgctg aaccgctctt ccgatc                         36

<210> SEQ ID NO 32
<211> LENGTH: 37
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (31)..(31)
<223> OTHER INFORMATION: n is 2-deoxyuridine

<400> SEQUENCE: 32
tttttttttt aatgatacgg cgaccaccga nctacac                        37

<210> SEQ ID NO 33
<211> LENGTH: 34
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (32)..(32)
<223> OTHER INFORMATION: n is 8-oxoguanine

<400> SEQUENCE: 33
tttttttttt caagcagaag acggcatacg anat                           34
```

METHOD FOR PAIRWISE SEQUENCING OF TARGET POLYNUCLEOTIDES

CROSS REFERENCE TO RELATED APPLICATIONS

This application is a continuation of U.S. application Ser. No. 13/539,000 filed Jun. 29, 2012, now U.S. Pat. No. 8,431, 348, which is a continuation of U.S. application Ser. No. 13/330,117 filed Dec. 19, 2011, now U.S. Pat. No. 8,236,505, which is a continuation of U.S. application Ser. No. 13/100, 166 filed May 3, 2011, now U.S. Pat. No. 8,105,784, which is a continuation of U.S. application Ser. No. 12/798,329 filed Apr. 1, 2010, now U.S. Pat. No. 7,960,120, which is a continuation of U.S. application Ser. No. 11/973,321 filed Oct. 5, 2007, now U.S. Pat. No. 7,754,429, which claims the priority of U.S. Provisional Application No. 60/898,910, filed on Feb. 1, 2007 and U.S. Provisional Application No. 60/850,210, filed on Oct. 6, 2006. The contents of all applications are hereby incorporated by reference in their entireties.

FIELD OF THE INVENTION

The invention relates to methods for pairwise sequencing of a double-stranded polynucleotide template, which methods result in the sequential determination of nucleotide sequences in two distinct and separate regions of the polynucleotide template.

BACKGROUND TO THE INVENTION

Several publications and patent documents are referenced in this application in order to more fully describe the state of the art to which this invention pertains. The disclosure of each of these publications and documents is incorporated by reference herein.

Advances in the study of biological molecules have been led, in part, by improvement in technologies used to characterise the molecules or their biological reactions. In particular, the study of the nucleic acids DNA and RNA has benefited from developing technologies used for sequence analysis.

One method for sequencing a polynucleotide template involves performing multiple extension reactions using a DNA polymerase to successively incorporate labelled nucleotides to a template strand. In such a "sequencing by synthesis" reaction a new nucleotide strand base-paired to the template strand is built up in the 5' to 3' direction by successive incorporation of individual nucleotides complementary to the template strand. If used simultaneously, the substrate nucleoside triphosphates used in the sequencing reaction may be blocked to prevent over-incorporation and labelled differently, permitting determination of the identity of the incorporated nucleotide as successive nucleotides are added.

In order to carry out accurate sequencing a reversible chain-terminating structural modification or "blocking group" may be added to the substrate nucleotides to ensure that nucleotides are incorporated one at a time in a controlled manner. As each single nucleotide is incorporated, the blocking group prevents any further nucleotide incorporation into the polynucleotide chain. Once the identity of the last-incorporated labelled nucleotide has been determined the label moiety and blocking group are removed, allowing the next blocked, labelled nucleotide to be incorporated in a subsequent round of sequencing.

In certain circumstances the amount of sequence data that can be reliably obtained with the use of sequencing-by-synthesis techniques, particularly when using blocked, labelled nucleotides, may be limited. In some circumstances it is preferred to limit the sequencing "run" to a number of bases that permits sequence realignment with the human genome, typically around 25-30 cycles of incorporation. Whilst sequencing runs of this length are extremely useful, particularly in applications such as, for example, SNP analysis and genotyping, it would be advantageous in many circumstances to be able to reliably obtain further sequence data for the same template molecule.

The technique of "paired-end" or "pairwise" sequencing is generally known in the art of molecular biology, particularly in the context of whole-genomic shotgun sequencing. Paired-end sequencing allows the determination of two "reads" of sequence from two places on a single polynucleotide duplex. The advantage of the paired-end approach is that there is significantly more information to be gained from sequencing two stretches each of "n" bases from a single template than from sequencing "n" bases from each of two independent templates in a random fashion. With the use of appropriate software tools for the assembly of sequence information it is possible to make use of the knowledge that the "paired-end" sequences are not completely random, but are known to occur on a single duplex, and are therefore linked or paired in the genome. This information has been shown to greatly aid the assembly of whole genome sequences into a consensus sequence.

Paired-end sequencing has typically been performed by making use of specialized circular shotgun cloning vectors. After cutting the vector at a specific single site, the template DNA to be sequenced (typically genomic DNA) is inserted into the vector and the ends resealed to form a new construct. The vector sequences flanking the insert DNA include binding sites for sequencing primers which permit sequencing of the insert DNA on opposite strands. However, the need for sequencing primers at both ends of the template fragment makes the use of array-based sequencing techniques extremely difficult. With array-based techniques, which usually rely on a single stranded template, it is generally only possible to sequence from one end of a nucleotide template, as the complementary strand is not attached to the surface.

A number of methods for double-ended sequencing of a polynucleotide template which can be carried out on a solid support have been reported, for example US20060024681, US20060292611, WO06110855, WO06135342, WO03074734, WO07010252, WO07091077 and WO00179553.

WO 98/44151 and WO 00/18957 both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions, for example as described in WO 98/44152. It is advantageous to enable the efficient sequencing of both strands of such clusters, as described in detail in the methods herein.

SUMMARY OF THE INVENTION

The present inventors have now developed methods for paired-end sequencing of double-stranded polynucleotide templates, including double-stranded templates present on clustered arrays, such as those described herein. The methods permit sequencing of two distinct regions, one at each end of the complementary strands of a target polynucleotide duplex.

Using the methods of the invention it is possible to obtain two linked or paired reads of sequence information from each double-stranded template on a clustered array, rather than just a single sequencing read from one strand of the template.

According to one method of the invention there is provided a method for pairwise sequencing of first and second regions of a target double-stranded polynucleotide, wherein said first and second regions are in the same target double-stranded polynucleotide, the method comprising:
(a) providing a solid support having immobilised thereon a plurality of double stranded template polynucleotides each formed from complementary first and second template strands linked to the solid support at their 5' ends, and multiple copies of one or more 5'-end immobilised primers capable of hybridising to the 3' end of the first template strand;
(b) treating the plurality of double stranded template polynucleotides such that the first template strands are hybridised to 5'-end immobilised primers;
(c) carrying out a first sequencing read to determine the sequence of a first region of the template polynucleotide;
(d) carrying out an extension reaction to extend one or more of the immobilised primers to copy the first template strand to generate a second immobilised template strand;
(e) treating the plurality of first and second immobilised template strands to remove the first template strand from the solid support;
(f) carrying out a second sequencing read to determine the sequence of a second region of the template polynucleotide, wherein determining the sequences of the first and second regions of the target polynucleotide achieves pairwise sequencing of said first and second regions of said target double-stranded polynucleotide.

A second method of the invention provides a method for sequencing end regions A and B of a target double-stranded polynucleotide, wherein said end regions A and B are in the same target double-stranded polynucleotide, the method comprising:
(a) providing a solid support having immobilised thereon a plurality of double stranded template polynucleotides each formed from complementary first and second template strands linked to the solid support at their 5' ends;
(b) treating the double stranded template polynucleotides such that each double stranded template polynucleotide is cut in at least two places to generate two shortened double stranded template fragments A and B immobilised at one end, wherein A and B are no longer directly connected;
(c) treating the two shortened double stranded template fragments A and B immobilised at one end to make the two non-immobilised ends a blunt ended duplex;
(d) treating the two blunt ended duplexes such that the two blunt ends A and B are connected to form a double stranded nucleotide sequence containing both ends A and B of the original target fragment in a shortened contiguous sequence, immobilised at both ends;
(e) cleaving one strand of the double stranded nucleotide sequence containing both distal ends A and B of the original target fragment joined in a shortened contiguous sequence immobilised at both ends to generate a single stranded nucleotide target sequence containing both distal ends A and B of the original target fragment in a shortened contiguous sequence, wherein said single stranded nucleotide target sequence is immobilised at a single 5' or 3' end;
(f) hybridising a sequencing primer to the single stranded nucleotide target sequence containing both distal ends A and B of the original target fragment in a shortened contiguous sequence; and
(g) carrying out a single sequencing reaction to determine a contiguous sequence of both ends A and B of the original target fragment.

A third method of the invention provides for pairwise sequencing of first and second regions of a target double-stranded polynucleotide, wherein said first and second regions are in the same target double-stranded polynucleotide, the method comprising:
(a) providing a solid support having immobilised thereon a plurality of double stranded template polynucleotides each formed from complementary first and second template strands linked to the solid support at both their 5' ends, and multiple copies of one or more 5'-end immobilised primers capable of hybridising to the 3' end of the first template strand;
(b) treating the plurality of double stranded template polynucleotides such that the first template strands are hybridised to a primer that is immobilised on the solid support at its 5'-end;
(c) carrying out a first sequencing to determine the sequence of a first region of the template polynucleotide;
(d) carrying out an extension reaction to extend one or more of the immobilised primers to the end of the first template strand to generate a second immobilised template strand;
(e) treating the plurality of template polynucleotides such that the first template strand is removed from the solid support leaving the second immobilised template strand single stranded;
(f) carrying out a second sequencing read to determine the sequence of a second region of the template polynucleotide, wherein determining the sequences of the first and second regions of the target polynucleotide achieves pairwise sequencing of said first and second regions of said target double-stranded polynucleotide.

In a more specific example, said third method is a method for pairwise sequencing of first and second regions of a target double-stranded polynucleotide, wherein said first and second regions are in the same target double-stranded polynucleotide, the method comprising:
(a) providing a solid support having immobilised thereon a plurality of double stranded template polynucleotides each formed from complementary first and second template strands linked to the solid support at their 5' ends;
(b) treating the plurality of double stranded template polynucleotides such that one of the strands is released from the surface leaving a single stranded first template strand immobilised on the solid support at its 5'-end;
(c) hybridising a primer to said first template strand and carrying out a first sequencing reaction to monitor the incorporation of labelled nucleotides onto the hybridised primer using cycles of primer extension with a polymerase and labelled nucleotides to generate a first extended sequencing primer and determine the sequence of a first region of the template polynucleotide;
(d) removing said first extended sequencing primer;
(e) hybridising the immobilised first template strand with immobilised primers and extending said immobilised primers to regenerate said plurality of double stranded template polynucleotides each formed from complementary first and second template strands linked to the solid support at their 5' ends;
(f) treating the plurality of template polynucleotides such that the first template strand is removed from the surface leaving the second immobilised template strand single stranded;
(g) hybridising a second sequencing primer to the second immobilised template strands; and
(h) carrying out a second sequencing run to monitor the incorporation of labelled nucleotides onto the second sequencing primer using cycles of primer extension with a polymerase and labelled nucleotides to generate a second extended sequencing primer and determine the sequence of a second region of the template polynucleotide, wherein determining the sequences of the first and second regions of the target polynucleotide achieves pairwise sequencing of said first and second regions of said target double-stranded polynucleotide.

Further covered within the embodiments of the inventions are clustered arrays prepared according to any method described herein, for example using strand resynthesis between two sequencing reads, or using a restriction endonuclease treatment to excise the central region of an immobilised duplex.

Further described herein is a method of improving the data quality of a sequencing reaction on an immobilised template, the method comprising hybridising the template to an immobilised primer such that the template is immobilised through both ends.

BRIEF DESCRIPTION OF THE FIGURES

FIG. 5 shows a representation of the clusters as grown on the surface.

FIG. 6 shows the full sequence of one strand of the template used for amplification.

FIG. 7 shows data from two cycles of nucleotide incorporation onto immobilised sequencing primer.

FIG. 8 shows data from sequencing reads obtained from the method shown in FIG. 4b. The sample used was a fragmented BAC of 140 KB fragmented to an average insert size of 80 base pairs. The two reads were obtained from either end of the fragment. Numerical data from a single tile of a sequencing run is shown. Both reads clearly align against the BAC sequence, with only 4% of the read derived from *E. coli* that contaminated the original sample.

DETAILED DESCRIPTION OF THE INVENTION

Figure 1:
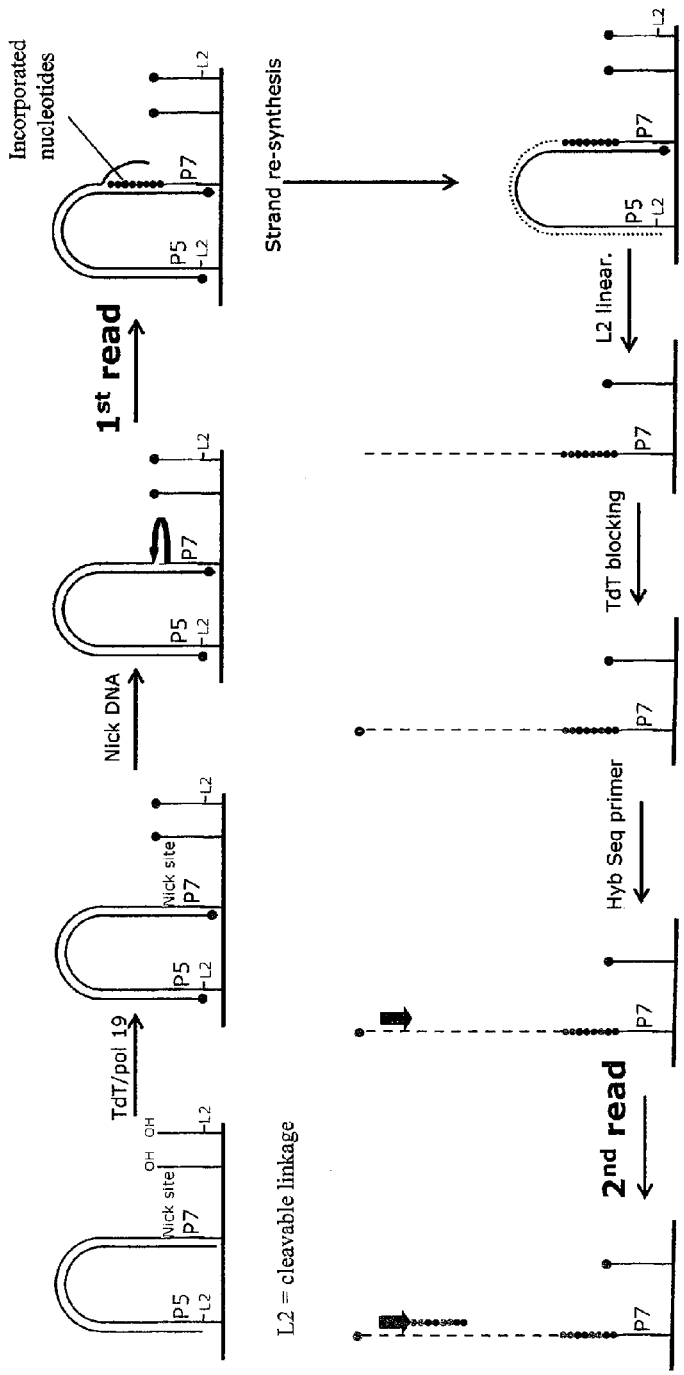
FIG. 1 shows a schematic of a paired-end read using a first method of the invention enabled with a nicking enzyme.

The invention provides a method for sequencing two regions of a target double-stranded polynucleotide template, referred to herein as the first and second regions for sequence determination. The first and second regions for sequence determination are at both ends of complementary strands of the double-stranded polynucleotide template, which are referred to herein respectively as first and second template strands. Once the sequence of a strand is known, the sequence of its complementary strand is also known, therefore the term two regions can apply equally to both ends of a single stranded template, or both ends of a double stranded template, wherein a first region and its complement are known, and a second region and its complement are known.

The starting point for the method of the invention is the provision of a plurality of template polynucleotide duplexes immobilised on a solid support. The template polynucleotides may be immobilised in the form of an array of amplified single template molecules, or 'clusters'. Each of the duplexes within a particular cluster comprises the same double-stranded target region to be sequenced. The duplexes are each formed from complementary first and second template strands which are linked to the solid support at or near to their 5' ends. Typically, the template polynucleotide duplexes will be provided in the form of a clustered array.

An alternate starting point is a plurality of single stranded templates which are attached to the same surface as a plurality of primers that are complementary to the 3' end of the immobilised template. The primers may be reversibly blocked to prevent extension. The single stranded templates may be sequenced using a hybridised primer at the 3' end. The sequencing primer may be removed after sequencing, and the immobilised primers deblocked to release an extendable 3' hydroxyl. These primers may be used to copy the template using bridged strand resynthesis to produce a second immobilised template that is complementary to the first. Removal of the first template from the surface allows the newly single stranded second template to be sequenced, again from the 3' end. Thus both ends of the original immobilised template can be sequenced. Such a technique allows paired end reads where the templates are amplified using a single extendable immobilised primer, for example as described in Polony technology (*Nucleic Acids Research* 27, 24, e34 (1999)) or emulsion PCR (*Science* 309, 5741, 1728-1732 (2005); *Nature* 437, 376-380 (2005)). The details described herein below regarding the individual steps apply mutatis mutandis to the steps described above, for example the primers may be blocked using the same techniques as described in the relevant sections below.

If the amplification is performed on beads, either with a single or multiple extendable primers, the beads may be analysed in solution, in individual wells of a microtitre or picotitre plate, immobilised in individual wells, for example in a fibre optic type device, or immobilised as an array on a solid support. The solid support may be a planar surface, for example a microscope slide, wherein the beads are deposited randomly and held in place with a film of polymer, for example agarose or acrylamide.

When referring to immobilisation or attachment of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc) which is been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

Figure 3:
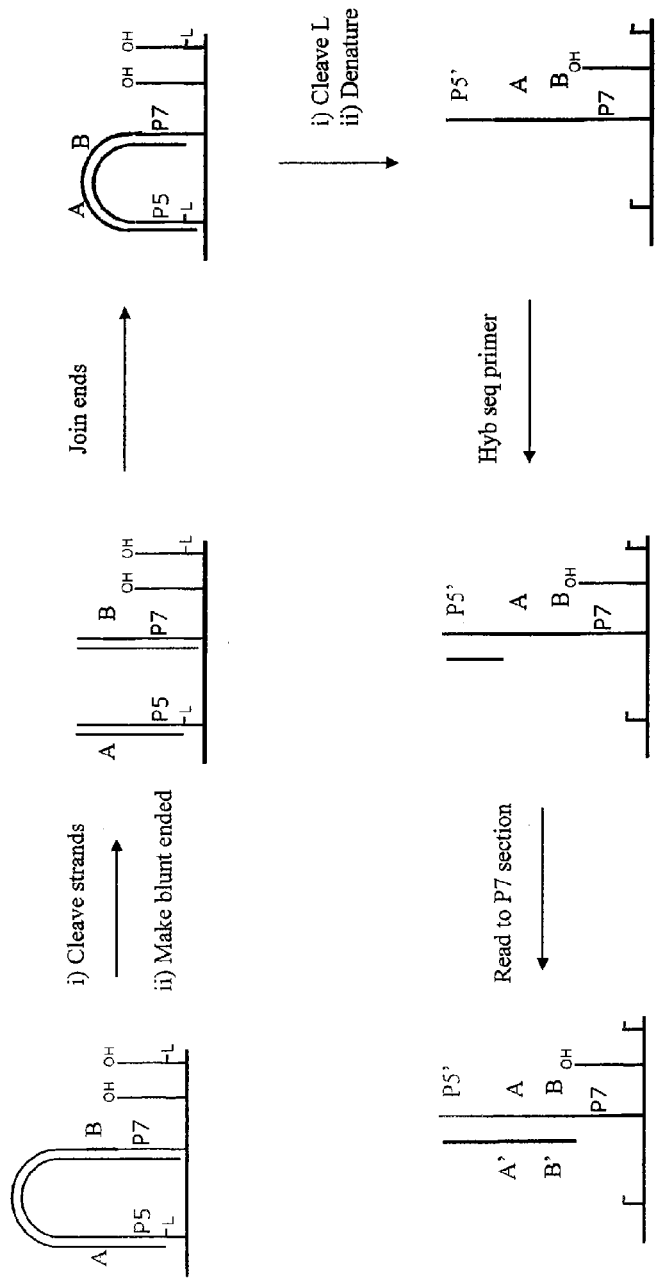
FIG. 3 shows a schematic of a paired read using a second method of the invention.

In order to sequence two regions of a given target double-stranded polynucleotide using the methods of the invention, the clusters can be manipulated either to excise the region of the target DNA between the two ends, or to obtain sequence data from both strands of the duplex. If the central portion of the cluster is excised, and the ends joined, it is possible to read the shortened contiguous sequence of the cluster in a single sequencing reaction that reads across both ends of the original template. This is similar to the idea of vector based (ditag) cloning in solution, but uses the cluster on the surface, which comprises a single sequence to ensure the two ends of the original fragment are joined. In the case of vectors in solution, the DNA fragments are ligated into circular constructs, and therefore the two ends (or tags) of the fragments remain on the same molecule even when the circle is cut open. This ensures two ends from the same original fragment are joined back together (to form ditags), without inter-molecular scrambling. In the case of clusters, the fact that the ends of the duplex fragments remain attached to the surface ensures that the ends from the original fragment are joined, which also prevents sequences from different molecules, or clusters, from mixing together. See FIG. 3 for a schematic of paired-end sequencing that calls for ligation of shortened ends. At the start of the procedure, the two ends A and B are covalently linked together via a series of intermediate bases, for example 100-1000 bases. A first treatment step cuts the cluster strands to leave only the ends A and B as separate short duplexes that are no longer covalently connected. A single strand of each duplex is attached to the surface, with the other strand hybridised. If the duplexes are made blunt ended, and ligated back together, ends AB (and AA and BB) are rejoined covalently without the intermediate bases.

Methods of treating the duplex to cut the strands at specific, but sequence independent, positions include using a restriction enzyme. Suitable restrictions enzymes are well known in the prior art, for example Mme1, that cuts 18 and 20 bases remotely to its binding site. It is desirable for the restriction enzyme to reach as far as possible into the unknown region of the DNA, and an enzyme that cuts between 10-50 bases, or further, is preferred. In a particular embodiment, an enzyme that cuts between 15-30 bases remote from its binding site, such as EcoP15, is envisioned.

The recognition sites for the particular restriction enzyme used can be engineered into both the primer used for solid phase amplification, and attached to the ends of the target fragments in the sample preparation step. The attachment of universal known ends to a library of DNA fragments by ligation allows the amplification of a large variety of different sequences in a single amplification reaction. The sequences of the known sequence portion of the nucleic acid template can be designed such the type 2s restriction enzymes bind to the known region, and cut into the unknown region of the amplified template.

Treatment of the duplexes where both strands are immobilised with the restriction enzyme(s) will give rise to two shortened duplex fragments in each cluster, each duplex anchored to the surface by one of its 5'-ends. Treatment with restriction enzymes usually leaves an overhang on one of the strands. The single stranded overhang can be filled in or removed, with a polymerase or exonuclease respectively, to ensure the ends of the duplex are blunt.

The blunt ended duplex fragments can then be joined together by ligation to produce duplexes where both 5' ends are immobilised. Such shortened duplexes contain the sequences derived from the two ends of original fragment, but without any intervening bases. A single sequencing run of say, 50 bases, could obtain the sequence of 25 bases from each end of the original fragment.

To facilitate sequencing, it is preferable if one of the strands is removed from the surface to allow efficient hybridisation of a sequencing primer to the remaining immobilised strand. Suitable methods for linearisation are described below, and described in more detail in application number WO07010251, the contents of which are incorporated herein by reference in their entirety. Linearisation also serves to limit the problem of ligation of two fragments from the same end rather than opposing ends. For each fragment with ends A and B, the 'stumps' A and B are left on the surface after the cleavage step. There is nothing to prevent A ligating to A or B ligating to B to give two repeated copies of one end, rather than the desired one copy of two ends. The linearisation of one of the strands helps avoid this problem, as for the three possibilities A-A, A-B or B-B, one duplex will have both strands removed, and one will have neither removed, and therefore remain as a duplex that is unavailable for hybridisation. Methods for linearisation and sequencing of clusters are described in full below.

In the first method of the invention, sequence data can be obtained from both ends of the immobilised duplex by a method wherein the duplex is treated to free a 3'-hydroxyl moiety that can be used an extension primer. The extension primer can then be used to read the first sequence from one strand of the template. After the first read, the strand can be extended to fully copy all the bases up to the end of the first strand. This second copy remains attached to the surface at the 5'-end. If the first strand is removed from the surface, the sequence of the second strand can be read. This gives a sequence read from both ends of the original fragment.

In the third method of the invention, sequence data can be obtained from both ends of a template duplex by obtaining a sequence read from one strand of the template from a primer in solution, copying the strand using immobilised primers, releasing the first strand and sequencing the second, copied strand.

Methods of generating a free 3'-hydroxyl in only one strand of a duplex immobilised at both ends include either treatment with a nicking enzyme, or chemical treatment to remove a specific nucleotide. Suitable nicking enzymes are well known in the art, and would preferably cut at a site that is 3'-remote to their binding site to avoid having to sequence bases that derive from the known nicked site. The nicking enzyme should cut only one of the immobilised strands, at the end closest to the surface. See FIG. 1 for schematic of paired end sequencing methodology utilising a nicking enzyme. Examples of suitable restriction enzymes would include Nt.BstNBI and Nt.AlwI, which have no bases of defined sequence beyond the released 3'-hydroxyl.

Methods of removing nucleotides from the duplex involve the design of the template such that the base immediately adjacent to the unknown target region can be removed to make an abasic site. An "abasic site" is defined as a nucleotide position in a polynucleotide chain from which the base component has been removed. Abasic sites can occur naturally in DNA under physiological conditions by hydrolysis of nucleotide residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

Figure 2:
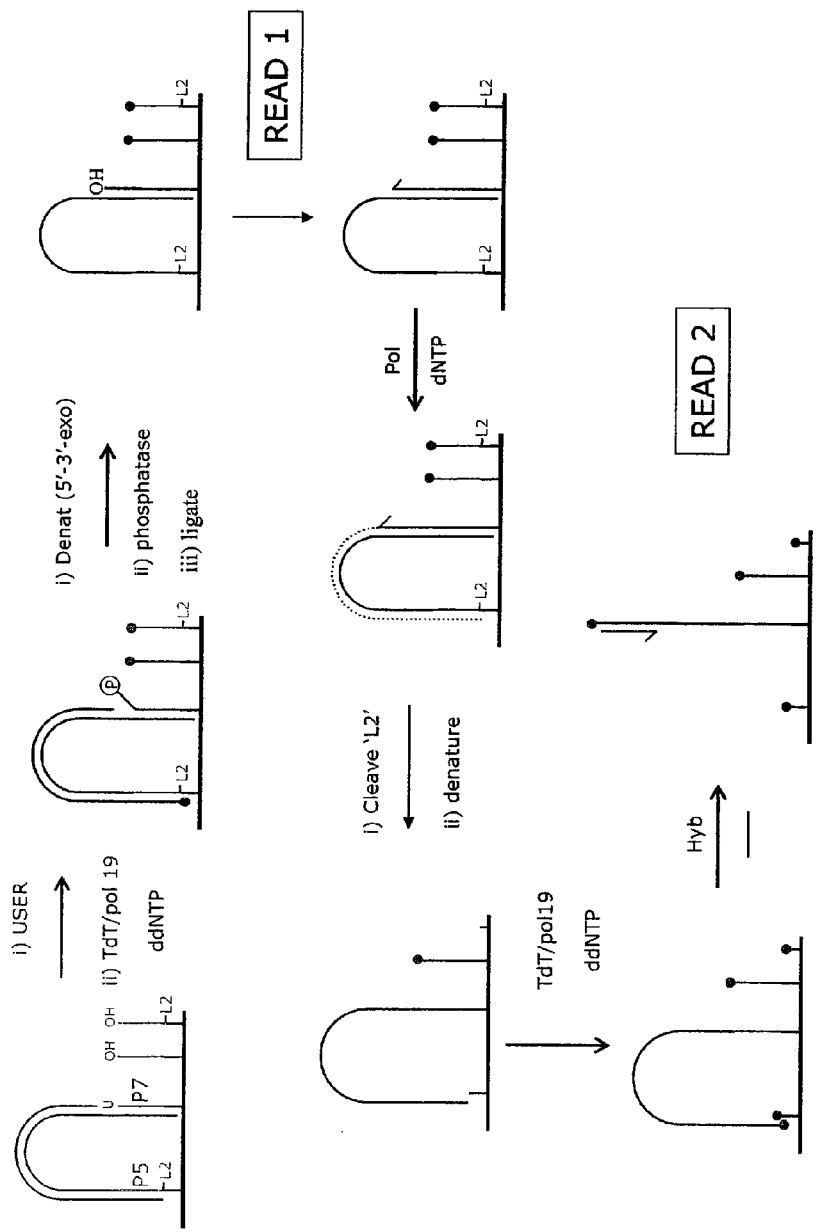
FIG. 2 shows a schematic of a paired read using a first method of the invention enabled with a uracil primer.

In a non-limiting embodiment an abasic site may be created at a pre-determined position on one strand of a template polynucleotide duplex and then cleaved by first incorporating deoxyuridine (U) at a pre-determined cleavage site in one strand of the template polynucleotide duplex. This can be achieved, for example, by including U in one of the primers used for preparation of the template polynucleotide duplex by solid-phase amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In a particular embodiment, the USER reagent available from New England Biolabs (M5505S) is used for the creation of a single nucleotide gap at a uracil base in a duplex strand. Treatment with endonuclease enzymes gives rise to a 3'-phosphate moiety at the cleavage site, which can be removed with a suitable phosphatase such as alkaline phosphatase. See FIG. 2 for a schematic of a paired-end sequencing reaction that utilizes USER linearization resynthesis.

Abasic sites may also be generated at non-natural/modified deoxyribonucleotides other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase). A further example includes the use of a specific non methylated cytosine. If the remainder of the primer sequences, and the dNTP's used in cluster formation are methylated cytosine residues, then the non-methylated cytosines can be specifically converted to uracil residues by treatment with bisulfite. This allows the use of the same 'USER' treatment to linearise both strands of the cluster, as one of the primers may contain a uracil, and one may contain the cytosine that can be converted into a uracil (effectively a 'protected uracil' species). If the non-natural/modified nucleotide is to be incorporated into an amplification primer for use in solid-phase amplification, then the non-natural/modified nucleotide should be capable of being copied by the polymerase used for the amplification reaction.

In one embodiment, the molecules to be cleaved may be exposed to a mixture containing the appropriate glycosylase and one or more suitable endonucleases. In such mixtures the glycosylase and the endonuclease will typically be present in an activity ratio of at least about 2:1.

This method of cleavage has particular advantages in relation to the creation of templates for nucleic acid sequencing. In particular, cleavage of an abasic site generated by treatment with a reagent such as USER automatically releases a free 3' phosphate group on the cleaved strand which after phosphatase treatment can provide an initiation point for sequencing a region of the complementary strand. Moreover, if the initial double-stranded nucleic acid contains only one cleavable (e.g. uracil) base on one strand then a single "nick" can be generated at a unique position in this strand of the duplex. Since the cleavage reaction requires a residue, e.g. deoxyuridine, which does not occur naturally in DNA, but is otherwise independent of sequence context, if only one non-natural base is included there is no possibility of glycosylase-mediated cleavage occurring elsewhere at unwanted positions in the duplex. In contrast, were the double-stranded nucleic acid to be cleaved with a "nicking" endonuclease that recognises a specific sequence, there is a possibility that the enzyme may create nicks at "other" sites in the duplex (in addition to the desired cleavage site) if these possess the correct recognition sequence. This could present a problem if nicks are created in the strand it is intended to copy, rather than the strand that will be fully or partially removed, and is a particular risk if the target portion of the double-stranded nucleic acid molecule is of unknown sequence. These limitations may be overcome by preparing a sample with the recognition site for two different nicking enzymes. If both preparations are processed separately using the method, the regions of the genome cleaved by one nicking enzyme should be represented in the other preparation.

The fact that there is no requirement for the non-natural (e.g. uracil) residue to be located in a detailed sequence context in order to provide a site for cleavage using this approach is itself advantageous. In particular, if the cleavage site is to be incorporated into an amplification primer to be used in the production of a clustered array by solid-phase amplification, it is only necessary to replace one natural nucleotide (e.g. T) in the primer with a non-natural nucleotide (e.g. U) in order to enable cleavage. There is no need to engineer the primer to include a restriction enzyme recognition sequence of several nucleotides in length. Oligonucleotide primers including U nucleotides, and other non-natural nucleotides, such as those listed above, can easily be prepared using conventional techniques and apparatus for chemical synthesis of oligonucleotides.

Another advantage gained by cleavage of abasic sites in a double-stranded molecule generated by action of UDG on uracil is that the first base incorporated in a "sequencing-by-synthesis" reaction initiating at the free 3' hydroxyl group formed by cleavage at such a site will always be T. Hence, if the template polynucleotide duplex forms part of a clustered array comprised of many such molecules, all of which are cleaved in this manner to produce sequencing templates, then the first base universally incorporated across the whole array will be T. This can provide a sequence-independent assay for individual cluster intensity at the start of a sequencing "run".

In particular cases, it may be advantageous to perform a blocking treatment with a dideoxynucleotide triphosphate and a polymerase and/or terminal transferase. After a solid phase amplification, there remain on the surface a large number of unused amplification primers, in addition to the free 3'-ends of each of the template strands. Treatment with such a blocked nucleotide ensures these free 3'-OH functional groups are unavailable for extension during any subsequent polymerase steps. In methods where 3'-hydroxyl groups are created with chemical treatment or restriction endonucleases, it is advantageous to block any residual 3'-hydroxyl groups before the desired 3'-hydroxyl groups are created. In the case of treatment with the USER reagent, as a phosphate group is released, the blocking step can be performed either before or after the USER treatment, as the phosphate group will act as a protecting group to prevent blocking of the desired 3'-hydroxyl moieties. The phosphate group can be removed after the blocking step has been performed.

The act of restriction enzyme treatment or abasic site generation and cleavage results in a free 5'-end on the strand that is no longer immobilised to the surface. This strand can be completely removed from the surface by treatment with a 5'-3' exonuclease, such as lambda or T7 exonuclease. Such a treatment means that the template strand is single stranded, and available for subsequent copying. If the polymerase that is used to extend the 3'-hydroxyl group has a strand displacing activity, then the 5'-3' exonuclease treatment may not be necessary.

In the embodiment of the invention, using an immobilised primer for sequencing, it is advantageous to extend the free 3'-hydroxyl primer with a plurality of bases complementary to the template prior to initiating sequencing. This both raises the melting temperature of the immobilised duplex, and helps prevent the template strand from re-hybridising to other immobilised primers during sequencing, which gives rises to phasing problems within the cluster. The ligation step is carried out after the phosphatase step has removed the phosphate group from the immobilised primer. Addition of 20-30 bases of sequence can be performed by a ligation reaction with a 5'-phosphate modified primer hydridised adjacent to the free 3'-hydroxyl. A ligase, such as T4 DNA ligase can be used to seal the gap. In the case of USER treatment which removes the U nucleotide, the 5'-base of the primer will be T that replaces the excised U. For the hybridisation step to be carried out efficiently, the 5'-non immobilised strand must have been removed by 5'-3' exonucleolysis treatment as described above. Such immobilised, extended primers with a free 3'-hydroxyl are described as extended 5'-anchored, or extended immobilised primers, and generation of such extended primers is only one of the steps involved in treating the plurality of double stranded template polynucleotides such that the first template strand is hybridised to a primer that is immobilised on the solid support at its 5'-end.

The free 3'-hydroxyl group on the 5'-anchored primer or extended primer can be used to initiate rounds of sequencing to determine the sequence of the bases in the hybridised template. Sequencing can be carried out using any suitable "sequencing-by-synthesis" technique, wherein nucleotides are added successively to the free 3' hydroxyl group, resulting in synthesis of a polynucleotide chain in the 5' to 3' direction. The nature of the nucleotide added is preferably determined after each addition. Alternative methods of sequencing include sequencing by ligation, for example as described in US6306597 or WO06084132, the contents of which are incorporated herein by reference.

The use of USER according to the present invention produces a linearised first template strand and a lawn of primers left with phosphate blocking moieties. Without further phosphatase treatment, the immobilised primer lawn is not suitable for polymerase extension. A sequencing primer in solution can be used to initiate a sequencing read for the first template strand. If the phosphate groups are removed from the lawn of primers, then the first template strands, once the first extended sequencing primer has been removed, can be hybridised to the primer lawn and subjected to one or more cycles of extension, denaturation and re-hybridisation. The denaturation can be performed thermally or isothermally, for example using chemical denaturation. The chemical denaturatant may be urea, hydroxide or formamide or other similar reagent. This re-generates the template duplexes where both strands are immobilised. The first strand can be removed by a suitable orthogonal linearisation treatment step, such as diol cleavage or removal of an 8-oxo-G residue, and after denaturation of the first template strand, a second sequencing primer can be hybridised to the second template strand, and the second template strand sequenced. This orthogonal linearisation strategy allows reads from both ends of the template.

The first method of the invention provides a sequencing reaction carried out using an immobilised primer. The immobilised sequencing primer can be denatured, and the first template strand used to re-initiate further rounds of extension or amplification as above. Again this re-generates the template duplexes where both strands are immobilised. The first strand can be removed by a suitable orthogonal linearisation treatment step, such as diol cleavage or removal of an 8-oxo-G residue, and after denaturation of the first template strand, a second sequencing primer can be hybridised to the second template strand, and the second template strand sequenced. This orthogonal linearisation strategy also allows reads from both ends of the template.

Both of the methods detailed above allow for cluster repopulation between the first and second reads. This is beneficial to increase the level of signal obtained for the second read of the cluster. Any method that results in both amplification primers being retained on the surface during the first sequencing read is within the scope of the third method of the invention, although it is advantageous if the primers can be treated, as in the case of USER, to make the 3'-hydroxyl unavailable for primer extension during the sequencing reaction. An alternative method of blocking the unextended grafting primers would be to use a nucleoside carry an unextendable 3' group. Treating the surface with such a nucleotide and terminal transferase would block the surface to further extension. After the first sequencing run, the nucleotides could be deprotected to allow further cycles of copying the template strand. If the nucleotides carry a dideoxy modification, this can be removed using an exonuclease, or a polymerase with exonuclease activity. Thus the clusters could be made with two grafted primers as described, the unused primers blocked during the first sequencing reaction, then deblocked to allow further copying of the template strands.

Figure 11:
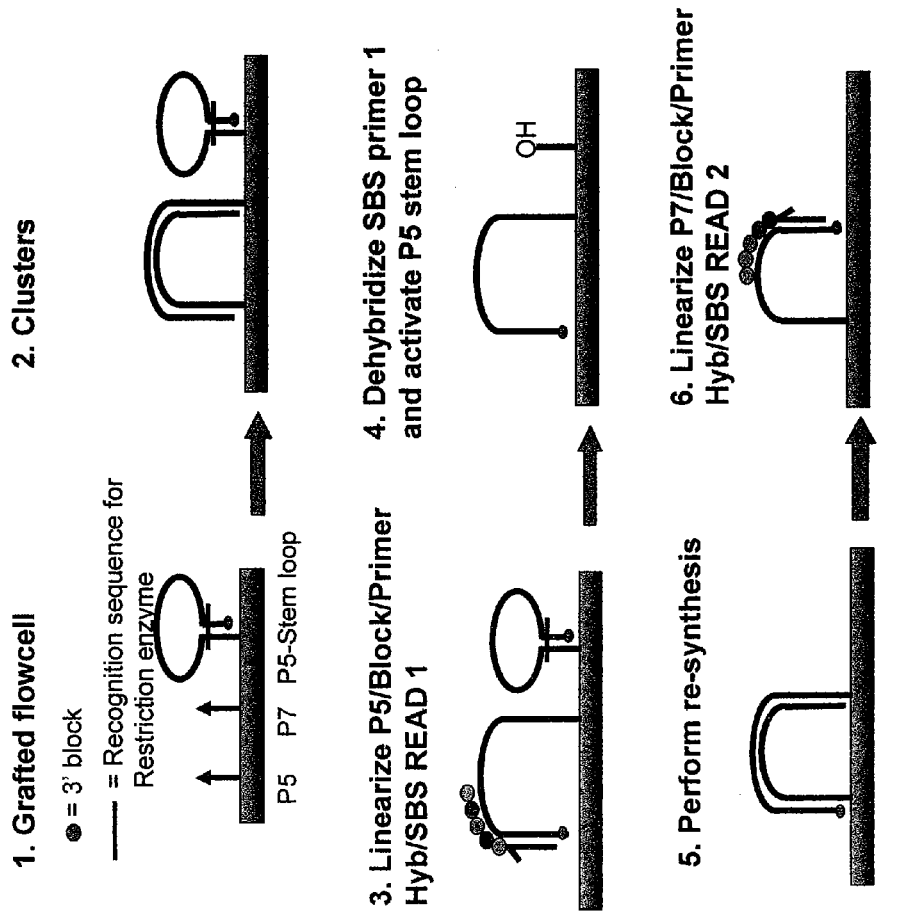
FIG. 11 shows an alternative method for reversibly blocking the immobilised primer.

A portion of the amplification primers may be attached to the surface with a modification blocking the 3' hydroxyl from extension in the amplification cycles. This in effect means that the surface is treated with three or more amplification primers rather than two. At least two of the amplification primers should comprise regions of identical sequence, but at least one primer will not be susceptible to the conditions used to remove the second primer during the linearisation process, and will contain a 3'-blocking moiety. The blocking moiety may take the form of a chemical block, such as an azidomethyl group that can be removed with a phosphine reagent, an enzymatically removable such as a phosphate group that can be removed with a phosphatase, or may be in the form of a nucleoside group that can be removed using 3'-5' exonucleolysis. Such nucleoside modifications include abasic sites, that can be removed as described, or 2',3' dideoxy nucleotides that can be removed by a polymerase with exonuclease activity. Further modifications include using an oligonucleotide sequence that can form a self complementary region with a recognition sequence for a restriction enzyme, as shown in FIG. 11. Treatment with the restriction enzyme should cut the hairpin strand and release a shorter sequence with a free 3' hydroxyl group. Treatment of the surface after the first sequencing run is completed to deblock the primers will allow the remaining first strand to hybridise to the deprotected primers and recopy the already sequenced strands. A second sequencing read can be obtained by removing the first strand, hybridising a sequencing primer and reading the newly synthesised second strand.

One particular sequencing method which can be used in the methods of the invention relies on the use of modified nucleotides that can act as reversible chain terminators. Such reversible chain terminators comprise removable 3' blocking groups. Once such a modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, to facilitate discrimination between the bases added at each incorporation step. Suitable labels are described in copending PCT application PCT/GB/2007/001770, the contents of which are incorporated herein by reference in their entirety. Alternatively, a separate reaction may be carried out containing each of the modified nucleotides added individually.

The modified nucleotides may carry a label to facilitate their detection. In a particular embodiment, the label is a fluorescent label. Each nucleotide type may carry a different fluorescent label. However the detectable label need not be a fluorescent label. Any label can be used which allows the detection of the incorporation of the nucleotide into the DNA sequence.

One method for detecting the fluorescently labelled nucleotides comprises using laser light of a wavelength specific for the labelled nucleotides, or the use of other suitable sources of illumination. The fluorescence from the label on an incorporated nucleotide may be detected by a CCD camera or other suitable detection means. Suitable detection means are described in copending application PCT/US2007/007991, the contents of which are incorporated herein by reference in their entirety.

Figure 9:
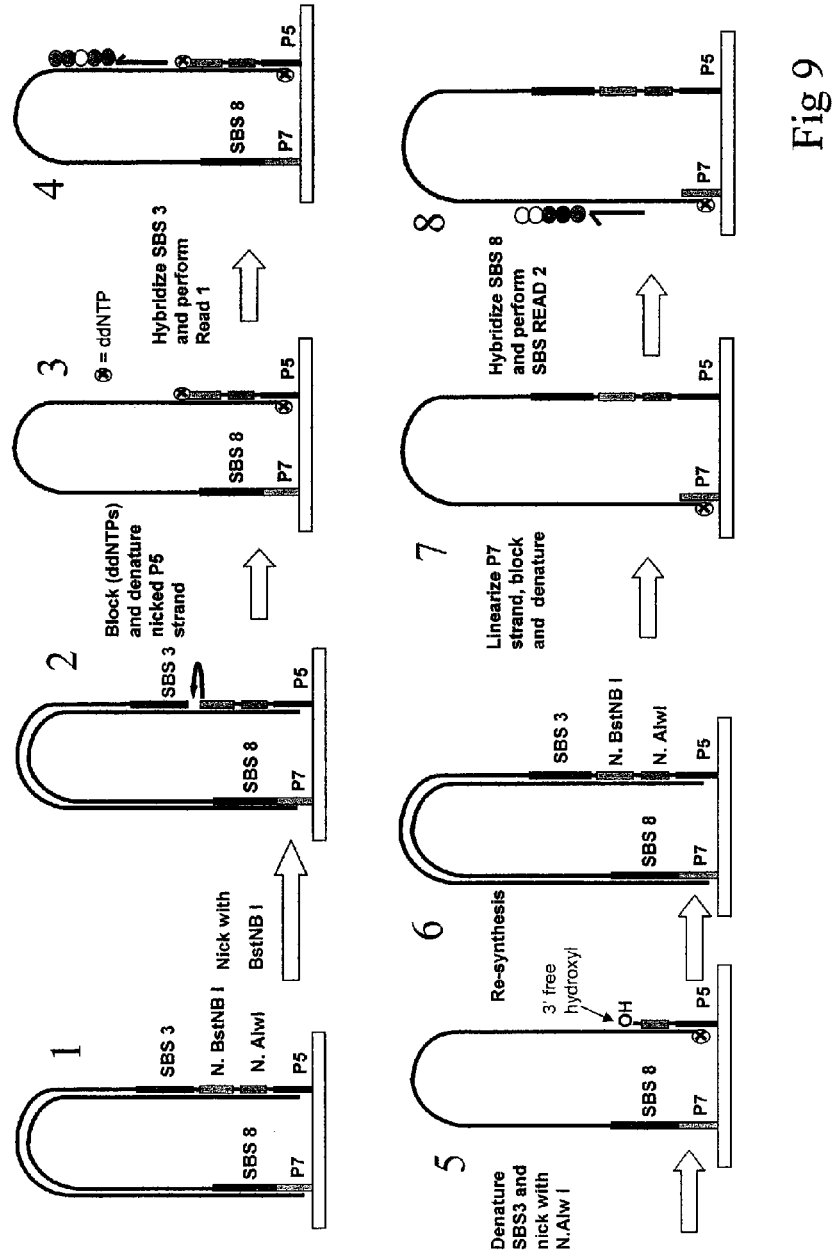
FIG. 9 shows a schematic of a method using two nicking enzymes and strand resynthesis.

Once the first sequencing read is complete, and sufficient read length has been determined, the rest of the strand can be copied. If the 3'-hydroxyl group was originally created with a nicking enzyme, then it will be possible to re-create a fresh 3'-hydroxyl group at the same position, and extend from this position, however it is equally possible to continue to copy the first template strand from the 3'-hydroxyl group of the nucleotides incorporated as part of the sequencing reaction. This extension reaction with all four unlabelled nucleotides and a polymerase will copy all the bases of first template. The immobilised primers may contain a restriction site for a nicking enzyme, and treatment with the restriction enzyme may shorten the immobilised primers, or the immobilised template duplexes to release an unblocked 3' hydroxyl group, as shown in FIG. 9.

Figure 4A:
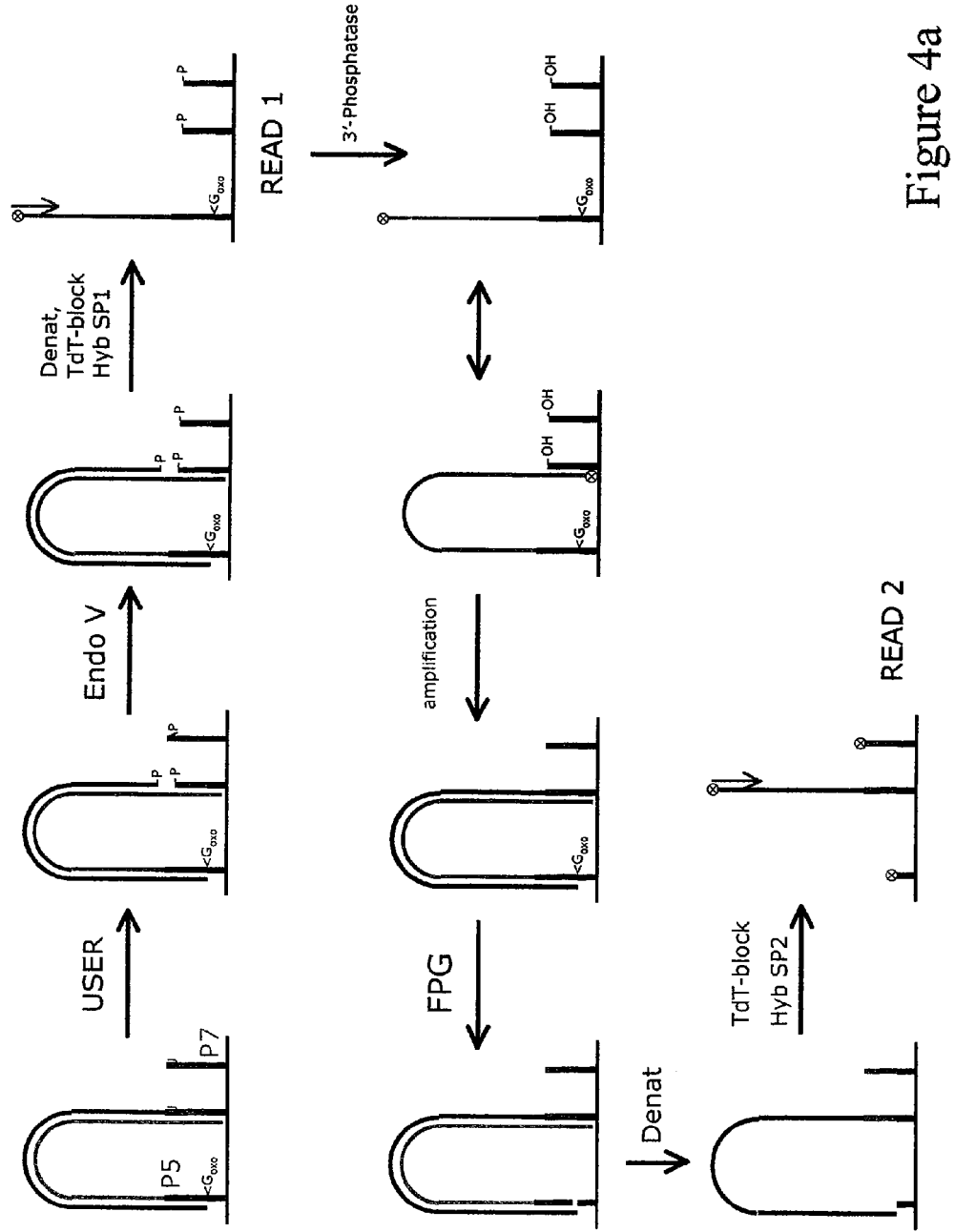
FIG. 4a shows a schematic of a paired read using a third method of the invention. The figure shows the first sequencing read occurring from a hybridised primer, but the strand may also be hybridised to the phosphate blocked primer on the surface, and hence may be immobilised via both ends (as shown in FIG. 4c).
Figure 4B:
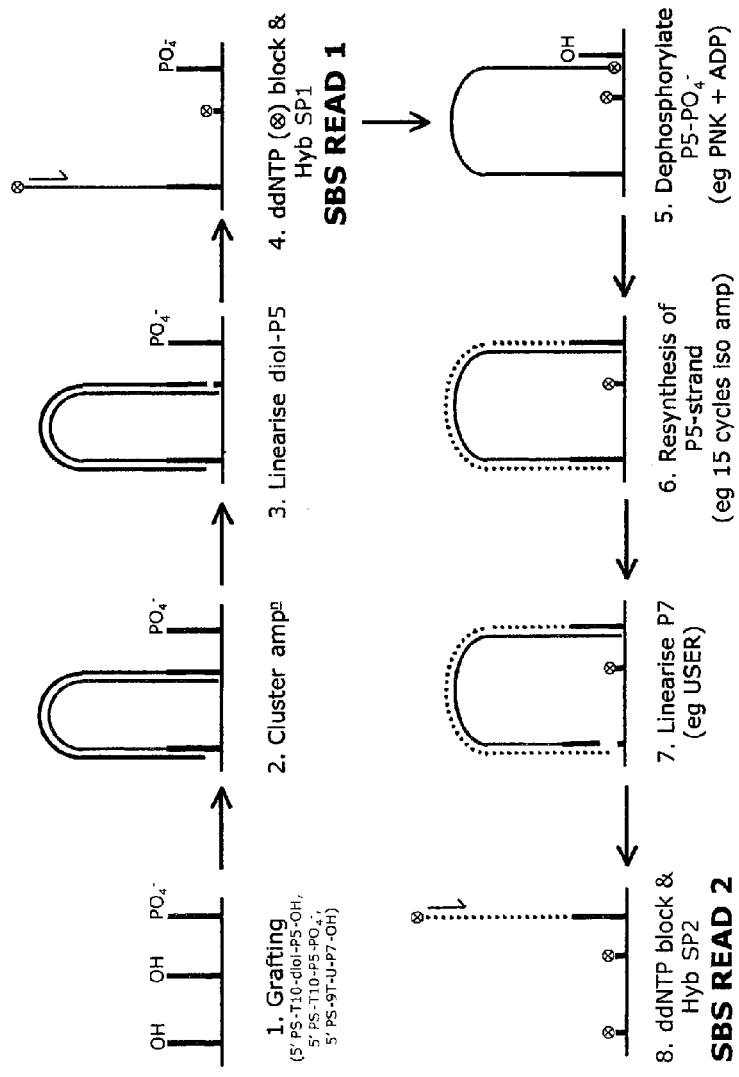
FIG. 4b shows a schematic of a paired read using the third method of the invention enabled using three grafting primers.
Figure 4C:
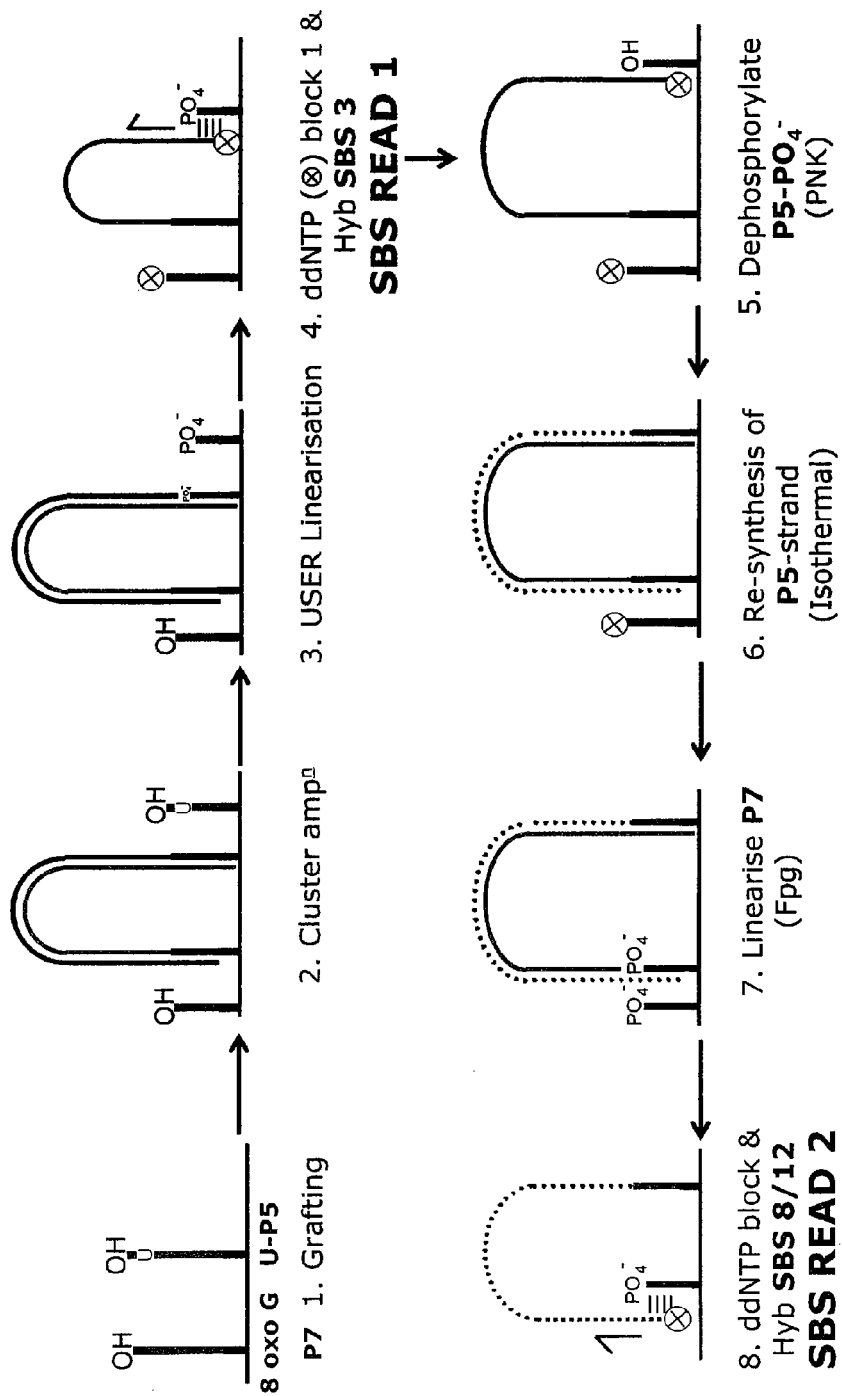
FIG. 4c shows the method of FIG. 4a, where the template is immobilised through both ends during SBS read 1.

In the course of developing the protocols included herein, it was surprisingly noticed that sequencing results were improved in situations where the 5' end of the template was capable of hybridisation to an immobilised primer. In short, sequencing as shown in FIG. 4c was better than sequencing as shown in FIG. 4a. In the experimental results shown herein, better means that the level of signal retained over multiple cycles was higher, meaning that the decay curve with both ends immobilised was less steep, and the signal higher than that where only a single end is immobilised. This may be due to the fact that any template strand breakages that occur during the sequencing process do not automatically result in loss of the template from the surface, as the 3' end of the template is also held in place by hybridisation, although there may also be other factors that cause this effect.

The first template strand may be attached to the surface in a way that allows selective removal. If the first template strand is removed from the surface, and the duplex strands denatured, for example by treatment with hydroxide or formamide, then the second, copied strand remains immobilised as a linearised single strand. As the end sequences of this strand are known, it is possible to hybridise a sequencing primer to the second template strand, and by repeating the cycles of sequencing as described above, determine the sequence of a second read for the other end of the template to the first read.

Selective removal, or linearisation of the first template strand can be achieved in a number of ways. The linearization to allow hybridization of a sequencing primer in solution does not have to leave a functional 3'-hydroxyl on the template strand, and can cleave either one strand or both strands. Thus, as used herein, the term "linearization" refers to the selective removal of a complementary strand. If one of the amplification primers is immobilised such that it can be cleaved from the surface, the resulting double stranded DNA can be made single stranded using heat or chemical denaturing conditions to give a single stranded molecule containing a primer hybridisation site. The single stranded molecule can be hybridised with a sequencing primer in solution to allow a sequencing read of the immobilised template strand. Said cleavage site is a site which allows controlled cleavage of the first template strand by chemical, enzymatic or photochemical means.

Any suitable enzymatic, chemical or photochemical cleavage reaction may be used to cleave. A number of suitable methods are described in WO07010251, the contents of which are incorporated herein by reference in their entirety. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulphide linkage with a reducing agent (e.g. TCEP), in which case the cleavage site should include an appropriate disulphide linkage; chemical cleavage of a diol linkage with periodate, in which case the cleavage site should include a diol linkage; generation of an abasic site and subsequent hydrolysis, etc.

In one embodiment cleavage may occur at a cleavage site in one or both strands of a template polynucleotide duplex which comprises one or more or any combination of non-natural nucleotides, ribonucleotides or a non-nucleotide chemical modifications.

Suitable cleavage techniques for use in the method of the invention include, but are not limited to, the following:
i) Chemical Cleavage The term "chemical cleavage" encompasses any method which utilises a non-nucleic acid and non-enzymatic chemical reagent in order to promote/achieve cleavage of one or both strands of a template polynucleotide duplex. If required, one or both strands of the template polynucleotide duplex may include one or more non-nucleotide chemical moieties and/or non-natural nucleotides and/or non-natural backbone linkages in order to permit a chemical cleavage reaction. In a particular embodiment, the modification(s) required to permit chemical cleavage may be incorporated into an amplification primer used to form the template polynucleotide duplex by solid-phase nucleic acid amplification.

In a preferred but non-limiting embodiment, one strand of the template polynucleotide duplex (or the amplification primer from which this strand is derived if formed by solid-phase amplification) may include a diol linkage which permits cleavage by treatment with periodate (e.g., sodium periodate). It will be appreciated that more than one diol can be included at the cleavage site.

Diol linker units based on phosphoamidite chemistry suitable for incorporation into polynucleotide chains are commercially available from Fidelity systems Inc. (Gaithersburg, Md., USA). One or more diol units may be incorporated into a polynucleotide using standard methods for automated chemical DNA synthesis. Hence, oligonucleotide primers including one or more diol linkers can be conveniently prepared by chemical synthesis.

In order to position the diol linker at an optimum distance from the solid support, one or more spacer molecules may be included between the diol linker and the site of attachment to the solid support. The spacer molecule may be a non-nucleotide chemical moiety. Suitable spacer units based on phosphoamidite chemistry for use in conjunction with diol linkers are also supplied by Fidelity Systems, Inc. One suitable spacer for use with diol linkers is the spacer denoted arm 26, identified in the accompanying examples. To enable attachment to a solid support at the 5' end of the polynucleotide strand, arm 26 may be modified to include a phosphorothioate group. The phosphorothioate group can easily be attached during chemical synthesis of a "polynucleotide" chain including the spacer and diol units.

Other spacer molecules could be used as an alternative to arm 26. For example, a stretch of non-target "spacer" nucleotides may be included. Typically from 1 to 20, more particularly from 1 to 15 or from 1 to 10, and even more particularly 2, 3, 4, 5, 6, 7, 8, 9 or 10 spacer nucleotides may be included. In a particular embodiment, 10 spacer nucleotides are positioned between the point of attachment to the solid support and the diol linker. In another particular embodiment, polyT spacers are used, although other nucleotides and combinations thereof can be used. In another particular embodiment, the primer may include 10T spacer nucleotides.

The diol linker is cleaved by treatment with a "cleaving agent", which can be any substance which promotes cleavage of the diol. In a particular embodiment, the cleaving agent is periodate, preferably aqueous sodium periodate ($NaIO_4$). Following treatment with the cleaving agent (e.g., periodate) to cleave the diol, the cleaved product may be treated with a "capping agent" in order to neutralise reactive species generated in the cleavage reaction. Suitable capping agents for this purpose include amines, such as ethanolamine or propanolamine. Advantageously, the capping agent (e.g., propanolamine) may be included in a mixture with the cleaving agent (e.g., periodate) so that reactive species are capped as soon as they are formed.

The combination of a diol linkage and cleaving agent (e.g., periodate) to achieve cleavage of at least one strand of a template polynucleotide duplex may be used to particular advantage for linearisation of template duplexes on solid supported polyacrylamide hydrogels because treatment with periodate is compatible with nucleic acid integrity and with the chemistry of the hydrogel surface. Utility of diol linkages/periodate as a method of linearisation is not, however, limited to polyacrylamide hydrogel surfaces but also extends to linearisation of duplexes immobilised on other solid supports and surfaces, including supports coated with functionalised silanes (etc).

In a further embodiment, the strand to be cleaved (or the amplification primer from which this strand is derived if prepared by solid-phase amplification) may include a disulphide group which permits cleavage with a chemical reducing agent, e.g. Tris(2-carboxyethyl)-phosphate hydrochloride (TCEP).

ii) Cleavage of Abasic Sites

The use of abasic sites is described above in order to generate a free 3'-hydroxyl moiety to act as a sequencing primer. If both amplification primers are modified such that they can be sequentially cleaved, the second cleavage can be used to cleave the first strand from the surface. The first (or second) primer could contain a uracil base, that can be cleaved by one enzyme (UDG), and the second (or first) primer could contain an 8-oxo-guanine base that can be cleaved by a second, orthogonal enzyme, FPG glycosylase. The second abasic site cleavage could be used to leave a sequencing primer attached to a surface, such that a G base is incorporated as the first cycle of sequencing, or the cleaved duplex strands can be denatured to allow hybridisation of a sequencing primer in solution.

iii) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, sequencing templates can be produced by cleavage of one strand of a template polynucleotide duplex at a site containing one or more consecutive ribonucleotides using such a chemical cleavage agent or an RNase. In a particular embodiment, the strand to be cleaved contains a single ribonucleotide, which provides a site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g., treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimise chemical (or enzymatic) cleavage. By way of example, rUMP or rCMP are generally preferred if cleavage is to be carried out by exposure to metal ions, especially rare earth metal ions.

The ribonucleotide(s) will typically be incorporated into one strand of a template polynucleotide duplex (or the amplification primer from which this strand is derived if prepared by solid-phase amplification), and may be situated in a region of the duplex which is single-stranded when the two complementary strands of the duplex are annealed (i.e., in a 5' overhanging portion). If the template polynucleotide duplex is prepared by solid-phase amplification using forward and reverse amplification primers, one of which contains at least one ribonucleotide, the standard DNA polymerase enzymes used for amplification are not capable of copying ribonucleotide templates. Hence, the amplification products will contain an overhanging 5' region comprising the ribonucleotide(s) and any remainder of the amplification primer upstream of the ribonucleotide(s).

The phosphodiester bond between a ribonucleotide and a deoxyribonucleotide, or between two ribonucleotides may also be cleaved by an RNase. Any endolytic ribonuclease of appropriate substrate specificity can be used for this purpose. If the ribonucleotide(s) are present in a region which is single-stranded when the two complementary strands of the double-stranded molecule are annealed (i.e., in a 5' overhanging portion), then the RNase will be an endonuclease which has specificity for single strands containing ribonucleotides. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesised using standard techniques for oligonucleotide chemical synthesis with appropriate ribonucleotide precursors. If the template polynucleotide duplex is prepared by solid-phase nucleic acid amplification, then it is convenient to incorporate one or more ribonucleotides into one of the primers to be used for the amplification reaction.

iv) Photochemical Cleavage

The term "photochemical cleavage" encompasses any method which utilises light energy in order to achieve cleavage of one or both strands of the double-stranded nucleic acid molecule.

A site for photochemical cleavage can be provided by a non-nucleotide chemical spacer unit in one of the strands of the double-stranded molecule (or the amplification primer from which this strand is derived if prepared by solid-phase amplification). Suitable photochemical cleavable spacers include the PC spacer phosphoamidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

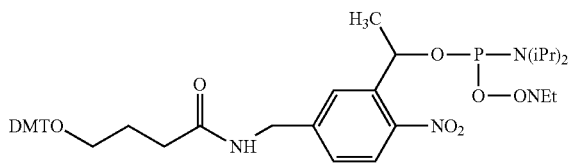

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable template polynucleotide duplex by solid-phase amplification.

v) PCR Stoppers

In another embodiment of the invention the template polynucleotide duplex may be prepared by solid-phase amplification using forward and reverse primers, one of which contains a "PCR stopper". A "PCR stopper" is any moiety (nucleotide or non-nucleotide) which prevents read-through of the polymerase used for amplification, such that it cannot extend/copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e., it may simply be a stretch of single-stranded DNA. The molecule may then be cleaved in the 5' overhanging region with the use of a cleavage reagent (e.g., an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Va., USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g. exposure to alkali) or an enzyme (e.g. AP-endonuclease VI, Shida et al. Nucleic Acids Research, 1996, Vol. 24, 4572-4576).

vi) Cleavage of Peptide Linker

A cleavage site can also be introduced into one strand of a template polynucleotide duplex by preparing a conjugate structure in which a peptide molecule is linked to one strand of the duplex (or the amplification primer from which this strand is derived if prepared by solid-phase amplification). The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the template polynucleotide duplex, with the peptide portion being conjugated to the 5' end of this strand, adjacent to the point of attachment to the solid surface. If the template polynucleotide duplex is prepared by solid-phase amplification, the peptide conjugate may be incorporated at the 5' end of one of the amplification primers. Obviously the peptide component of this primer will not be copied during amplification, hence the "bridged" amplification product will include a cleavable 5' peptide "overhang" on one strand.

Conjugates between peptides and nucleic acids wherein the peptide is conjugated to the 5' end of the nucleic acid can be prepared using techniques generally known in the art. In one such technique the peptide and nucleic acid components of the desired amino acid and nucleotide sequence can be synthesised separately, e.g. by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-5-tert-butylsulfenyl-l-cysteinyl)aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the modified peptide is converted to the thiophenyl analogue by the use of thiophenol, whilst the modified oligonucleotide is reduced using tris(carboxyethyl)-phosphine. Coupling of these two intermediates, followed by the "native ligation" step, leads to formation of the oligonucleotide-peptide conjugate.

The conjugate strand containing peptide and nucleic acid can be covalently attached to a solid support using any suitable covalent linkage technique known in the art which is compatible with the chosen surface. If the peptide/nucleic acid conjugate structure is an amplification primer to be used for solid-phase amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase amplification, then its length and nucleotide sequence will be selected to enable annealing to the template to be amplified.

vii) Enzymatic Digestion with Restriction Endonuclease/Nicking Endonuclease

Cleavage of double-stranded polynucleotides with restriction endonuclease is a technique in routine use in the art of molecular biology. Nicking endonucleases are enzymes that selectively cleave or "nick" one strand of a polynucleotide duplex and are also well known in the art of molecular biology. The invention is not limited with respect to the nature of the enzyme. Essentially any restriction or nicking endonuclease may be used, provided that a suitable recognition sequence can be included at the cleavage site. In the case of the invention using two sequencing reads, the choice of nicking enzyme will need to be different to that used in the first cycle of extension, and this can be enabled using amplification primers with recognition sites for two different enzymes.

The method of the invention is described in further detail as follows.

Any suitable solid support and any suitable attachment means known in the art may be used, of which several are described by way of example below. In a particular embodiment, linkage to the solid support is achieved via covalent attachment.

The polynucleotide duplexes will typically be formed from two complementary polynucleotide strands comprised of deoxyribonucleotides joined by phosphodiester bonds, but may additionally include one or more ribonucleotides and/or non-nucleotide chemical moieties and/or non-naturally occurring nucleotides and/or non-naturally occurring backbone linkages. In particular, the double-stranded nucleic acid may include non-nucleotide chemical moieties, e.g. linkers or spacers, at the 5' end of one or both strands. By way of non-limiting example, the double-stranded nucleic acid may include methylated nucleotides, uracil bases, phosphorothioate groups, ribonucleotides, diol linkages, disulphide linkages, peptides etc. Such non-DNA or non-natural modifications may be included in order to permit cleavage, or to confer some other desirable property, for example to enable covalent attachment to a solid support, or to act as spacers to position a site of cleavage an optimal distance from the solid support.

The template duplexes may also include non-target sequences at both the 5' and 3' ends, flanking the target polynucleotide. If the template duplexes are formed by solid-phase amplification, these non-target sequences will generally be derived from the primers used for solid-phase amplification.

The polynucleotide duplexes form part of a single cluster or colony comprised of many such first and second duplexes, and the cluster or colony will itself typically form part of an array of many such clusters or colonies. The terms "cluster" and "colony" are used interchangeably throughout and refer to a discrete site on a solid support comprised of a plurality of identical immobilised nucleic acid strands and a plurality of identical immobilised complementary nucleic acid strands. The term "clustered array" refers to an array formed from such clusters or colonies.

A key feature of the invention is that both sequencing runs can occur in the same cluster or colony on a clustered array. On such an array each duplex within each colony will comprise the same double-stranded target polynucleotide, whereas different colonies may be formed of duplexes comprising different double-stranded target polynucleotides. In a particular embodiment at least 90%, more particularly at least 95% of the colonies on a given clustered array will be formed from template duplexes comprising different double-stranded target polynucleotides, although within each individual colony on the array all template duplexes will comprise the same double-stranded target polynucleotide.

The amplified polynucleotides can be treated in such a way to enable extension of a hybridised primer. Each polynucleotide duplex on the array contains the same universal primer recognition regions to allow the same primers to be used to sequence every cluster. A first sequencing primer is then hybridised to the first template strand and a sequencing reaction proceeds via successive incorporation of nucleotides or oligonucleotides to the first sequencing primer, resulting in determination of the sequence of a first region of the target polynucleotide. In the case of the method where both ends of the original fragment are made contiguous (see FIG. 3), the first sequencing run gives sequence information for both ends of the original fragment. At this point, the method is complete; there is no need for further processing of the sample.

By contrast, the other methods of the invention require two sequencing reactions to be performed. The first sequencing reaction is initiated either by the 3'-hydroxyl group of the immobilised primer that is freed from within the immobilised duplex, or is initiated by a sequencing primer added from solution. The second sequencing reaction is initiated by a sequencing primer that can either be immobilised or applied in solution. Hybridisation of the sequencing primer in solution to the template strand is achieved by contacting the primer and template strand under conditions which promote annealing of primer to template. Such conditions will generally be well known to those skilled in the art of molecular biology.

When the first sequencing reaction is complete, if the first sequencing primer is immobilised this can be used to further extend the strand to copy every base on the template. This is carried out using the four native nucleotide triphosphates, dATP, dGTP, dCTP and dTTP, and a suitable polymerase. If the complementary strand was removed by treatment with a 5'-3' exonuclease step prior to the sequencing reaction, then the extension reaction can be carried out at any temperature as the strand is already single stranded, and therefore any polymerase such as Klenow, Taq or vent is suitable. If the strand has not been removed, then a polymerase with strand displacing activity, such as Bst polymerase will be required.

Figure 10:
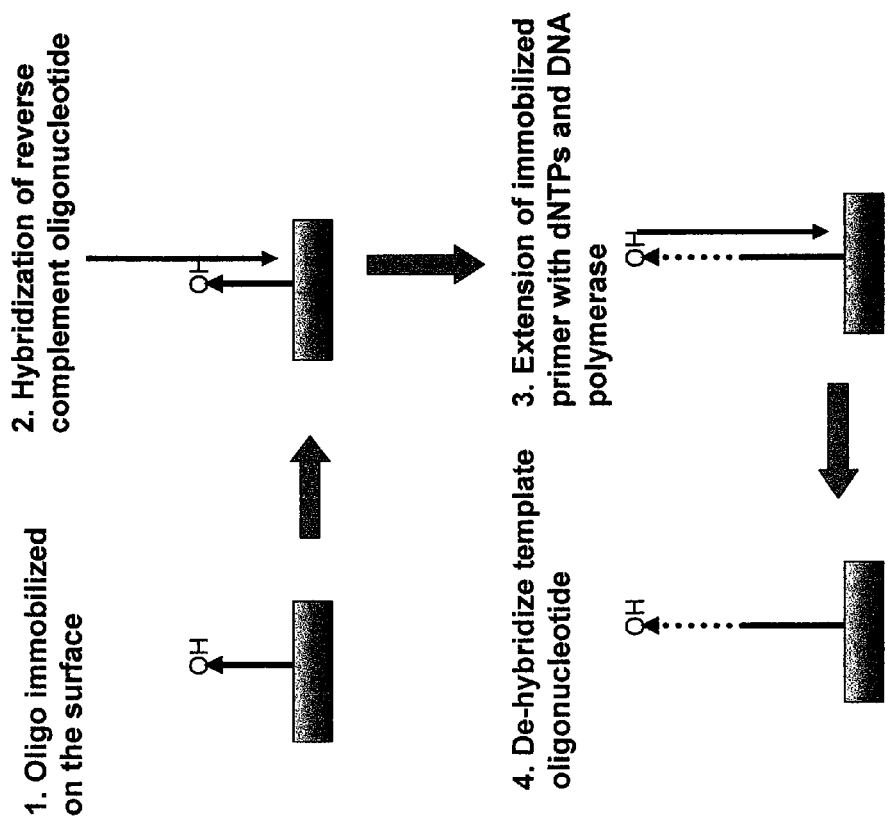
FIG. 10 shows the optional step of primer extension prior to strand resynthesis, which improves the strand resynthesis step.

Prior to undertaking the extension reaction, it may be advantageous to extend the immobilised primer, as shown in FIG. 10. The extension can performed using a hybridised oligonucleotide with a sequence that extends beyond the 3' end of the immobilised primer, whose sequence is also the same sequence as the corresponding region at the end of the template. This extended portion can serve as a basis for extension of the immobilised primer, and thus the extended primer is complementary to the immobilised template strand. The extended primers may improve the efficiency of the strand resynthesis step due to their increased length.

Once a complementary sequence of the first strand has been generated, the first strand can be removed from the surface as described above. A second sequencing primer is then hybridised to the copied strand of the template and a sequencing reaction proceeds via successive addition of nucleotides to the second sequencing primer, resulting in determination of the sequence of a second region of the target polynucleotide. See FIG. 1.

As described above, sequencing can be carried out using any suitable "sequencing-by-synthesis" technique, wherein nucleotides or oligonucleotides are added successively to a free 3' hydroxyl group, typically provided by annealing of a sequencing primer, resulting in synthesis of a polynucleotide chain in the 5' to 3' direction. In a particular embodiment, the nature of the nucleotide or oligonucleotide added is determined after each addition.

One particular sequencing method which can be used in the methods of the invention relies on the use of modified nucleotides that can act as reversible chain terminators. Nucleotides for use in the invention are described fully in WO04018497. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, which facilitates discrimination between the bases added at each incorporation step. Alternatively, a separate reaction may be carried out containing each of the modified nucleotides, which are added separately.

The modified nucleotides may carry a label to facilitate their detection. In a particular embodiment, the label is a fluorescent label. Each nucleotide type may carry a different fluorescent label. Fluorescent labels suitable for use in the current invention are described in PCT application PCT/GB2007/001770. However the detectable label need not be a fluorescent label. Any label can be used which allows the detection of the incorporation of the nucleotide into the DNA sequence.

One method for detecting the fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. An imaging system suitable for determining the fluorescence signal from incorporated nucleotides is described in PCT application number PCT/US07/007,991.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods.

The target double-stranded polynucleotide to be sequenced using the method of the invention may be any polynucleotide that it is desired to sequence. The target polynucleotide may be of known, unknown or partially known sequence, such as, for example in re-sequencing applications. Using the template preparation method described in detail below it is possible to prepare arrays of templates starting from essentially any double-stranded target polynucleotide of known, unknown or partially known sequence. With the use of arrays it is possible to sequence multiple targets of the same or different sequence in parallel. A particular application of the pairwise method is in the sequencing of fragments of genomic DNA. The method provides particular advantages in the identification of genome rearrangements, since the two regions of sequence obtained for each target molecule using the method will be known to be linked within a certain distance of each other in the genome, depending on the size of the starting target molecule.

Preparation of Templates to be Sequenced

Suitable templates for sequencing using the method of the invention can be prepared by solid-phase nucleic acid amplification to produce nucleic acid colonies. The templates to be amplified will generally comprise unknown regions flanked by known ends, for example prepared according to methods described in application WO07052006, whose contents are incorporated herein by reference in their entirety. For example, the templates may derive from a sample of genomic DNA, or from a cDNA library. The amplification can be done using procedures analogous to those described in WO 98/44151, WO 00/18957, WO0206456 or WO07107710, the contents of which are incorporated herein in their entirety by reference.

Figure 12:
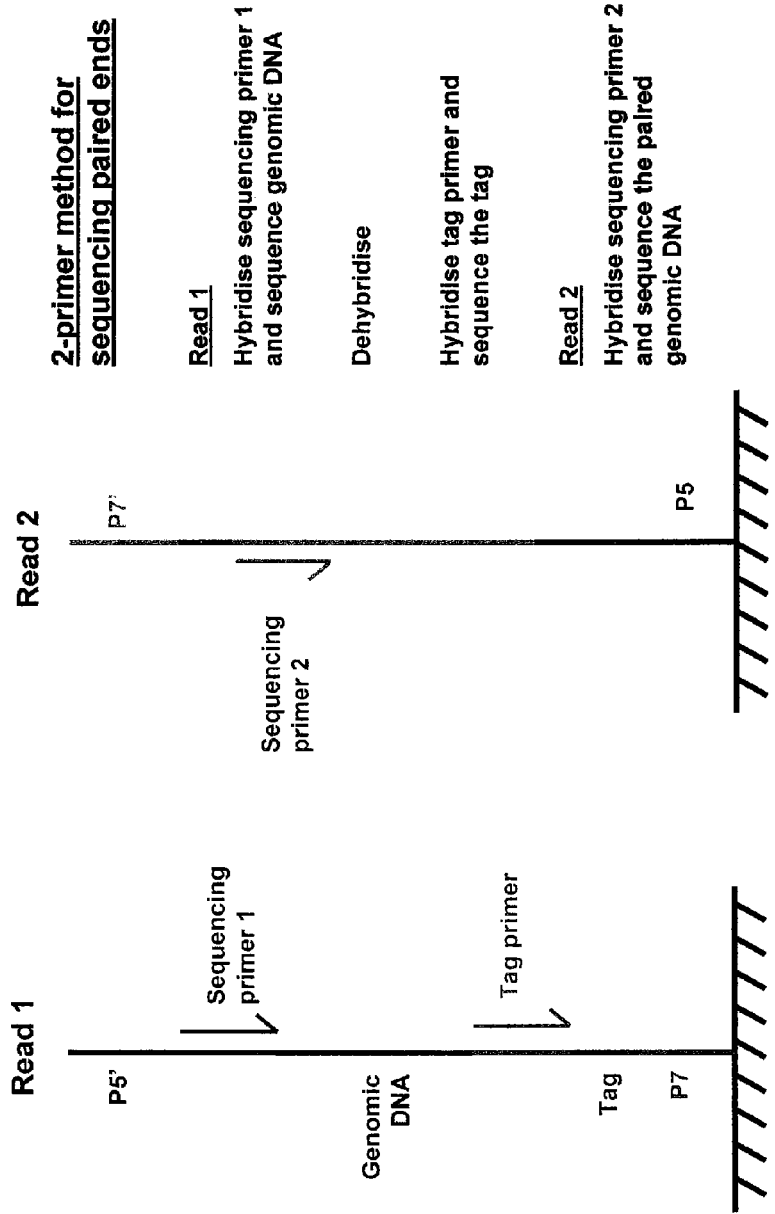
FIG. 12 shows a schematic of indexing paired reads, wherein the sample templates are prepared using an indexing sequence or tag.

The templates for amplification may be prepared to contain a tag sequence, for example as shown in FIG. 12. The use of a tag sequence, for example as described in application WO05068656, whose contents are incorporated herein by reference in their entirety, allows multiple different samples to be analysed in the same sequencing run whilst preserving the identity of each sample. FIG. 12 shows the tag that is read at the end of the first read, but the tag can equally be read at the end of the second read, for example using a sequencing primer complementary to the strand marked P7. The invention is not limited to two reads per cluster, three or more reads per cluster are obtainable simply by dehybridising a first extended sequencing primer, and rehybridising a second primer before or after the cluster repopulation/strand resynthesis step. Methods of preparing suitable samples for indexing are described in copending application US60/899,221 filed Feb. 1, 2007.

For amplification to proceed, a mixture of at least two amplification primers is immobilised or "grafted" onto the surface of a suitable solid support.

The amplification primers are oligonucleotide molecules having the following structures:
Forward primer: A-L-X-S1
Reverse primer: A-L-Y-S2

Wherein A represents a moiety which allows attachment to the solid support, L is an optional linker or spacer moiety, X and Y are optional cleavage sites as described above to allow subsequent removal of one or other of the strands from the surface and S1 and S2 are polynucleotide sequences which permit amplification of a template nucleic acid molecule comprising the target double-stranded polynucleotide.

The mixture of primers will generally comprise substantially equal amounts the forward and reverse primers.

L represents a linker which may be included but is not strictly necessary. The linker may be a carbon-containing chain such as those of formula $(CH_2)_n$ wherein "n" is from 1 to about 1500, for example less than about 1000, preferably less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA amplification and sequencing.

Linkers which do not consist of only carbon atoms may also be used. Such linkers include polyethylene glycol (PEG) having a general formula of $(CH_2-CH_2-O)_m$, wherein m is from about 1 to 600, preferably less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, and sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

As an alternative to the linkers described above, which are primarily based on linear chains of saturated carbon atoms, optionally interrupted with unsaturated carbon atoms or heteroatoms, other linkers may be envisaged which are based on nucleic acids or monosaccharide units (e.g. dextrose). It is also within the scope of this invention to utilise peptides as linkers.

In a further embodiment, a linker may comprise one or more nucleotides which form part of the amplification primer but which do not participate in any reaction carried out on or with the primer (e.g., a hybridisation or amplification reaction). Such nucleotides may also be referred to herein as "spacer" polynucleotides. Typically from 1 to 20, more preferably from 1 to 15 or from 1 to 10, and more particularly 2, 3, 4, 5, 6, 7, 8, 9 or 10 spacer nucleotides may be included. In a particular embodiment, the primer includes 10 spacer nucleotides. PolyT spacers may be used in some embodiments, although other nucleotides and combinations thereof can also be used. In a particular embodiment, the primer may include 10T spacer nucleotides.

The one or more spacer nucleotides function to space the portion of the primer required to hybridise to a target and direct amplification away from the site of attachment to the solid support (i.e., S1 or S2). The inclusion of spacer nucleotides at the 5' end can markedly improve the performance of hybridisation of complementary polynucleotides to region S1 or S2. In a more particular embodiment the polynucleotide includes 10T spacer nucleotides and a 5' phosphorothioate group for attachment to the solid support (moiety A), although other attachment moieties may be used as discussed below.

Sequences S1 and S2 in the forward and reverse primers are polynucleotide sequences which, in combination, direct amplification of a template by solid-phase bridging amplification reaction. The template to be amplified must itself comprise (when viewed as a single strand) at the 3' end a sequence capable of hybridising to sequence S1 in the forward primers and at the 5' end a sequence the complement of which is capable of hybridising to sequence S2 the reverse primer.

The precise nature of sequences S1 and S2 in the forward and reverse primer oligonucleotides will be dependent on the nature of the template it is intended to amplify. S1 and S2 must be capable of hybridising to cognate sequences on complementary strands of the template to be amplified. The term "hybridisation" encompasses sequence-specific binding between primer and template. Binding of a primer to its cognate sequence in the template should occur under typical conditions used for primer-template annealing in standard PCR. Typically hybridisation conditions are 5×SSC at 40° C., following an initial denaturation step. It is not essential for hybridisation that sequences S1 and S2 be exactly complementary to their cognate sequences in the template to be amplified, although this is preferred.

S1 and S2 may be of different or identical sequence and will typically be around 20-30 nucleotides in length. The primers can include natural and non-natural DNA bases, also ribonucleotides or any combination thereof, and may also include non-natural backbone linkages such as disulphides or phosphorothioates.

Cleavage site X and/or Y may fall within sequence S1 or S2, or if the linker L is itself a polynucleotide cleavage they may form part of linker region L. In other embodiments the cleavage site may be formed at the junction of sequences L and S1 or L and S2, or at the junction between moiety A and linker L (if present) or between moiety A and sequence S1 or S2 (if L not present).

Moiety A may be any chemical moiety which permits immobilisation of an oligonucleotide primer on a solid support. The surface of the solid support may itself be functionalised to permit attachment of the primers. Any suitable covalent or non-covalent attachment means may be used, of which many are known in the art.

By way of example, biotinylated albumins (BSA) can form a stable attachment of biotin groups by physisorption of the protein onto surfaces. Covalent modification can also be performed using silanes, which have been used to attach molecules to a solid support, usually a glass slide. By way of example, a mixture of tetraethoxysilane and triethoxy-bromoacetamidopropyl-silane (e.g. in a ratio of 1:100) can be used to prepare functionalised glass slides which permit attachment of molecules such as nucleic acids including a thiophosphate or phosphorothioate functionality. Biotin molecules can be attached to surfaces using appropriately reactive species such as biotin-PEG-succinimidyl ester which reacts with an amino surface. A mixture of amplification primers may then be brought into contact with the functionalised solid support.

In alternative embodiments functionalised polyacrylamide hydrogels may be used to attach primers wherein moiety A is a sulfur-containing nucleophilic group. Examples of appropriate sulfur nucleophile-containing polynucleotides are disclosed in Zhao et al (*Nucleic Acids Research,* 2001, 29(4), 955-959) and Pirrung et al (*Langmuir,* 2000, 16, 2185-2191) and include, for example, simple thiols, thiophosphates and thiophosphoramidates. In particular embodiments, hydrogels are formed from a mixture of (i) a first comonomer which is acrylamide, methacrylamide, hydroxyethyl methacrylate or N-vinyl pyrrolidinone; and (ii) a second comonomer which is a functionalised acrylamide or acrylate of formula (I):

or a methacrylate or methacrylamide of formula (II):

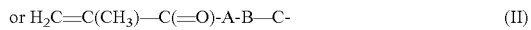

(wherein:

A is NR or O, wherein R is hydrogen or an optionally substituted saturated hydrocarbyl group comprising 1 to 5 carbon atoms;

—B— is an optionally substituted alkylene biradical of formula —(CH$_2$)$_n$— wherein n is an integer from 1 to 50; and wherein n=2 or more, one or more optionally substituted ethylene biradicals —CH$_2$CH$_2$— of said alkylene biradical may be independently replaced by ethenylene and ethynylene moieties; and wherein n=1 or more, one or more methylene biradicals —CH$_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 CH$_2$ or CH$_2$ is substituted by an oxygen sulfur or nitrogen atom or an NH group; and C is a group for reaction with a compound (to bind the compound covalently to the hydrogel) to form a polymerised product. In a particular embodiment, the hydrogel is formed by co-polymerisation of acrylamide and N-(5-bromoacetamidylpentyl)acrylamide (BRAPA), as described in application WO05065814, the contents of which are incorporated herein by reference in their entirety.

The term "solid support", as used herein, refers to the material to which the polynucleotides molecules are attached. Suitable solid supports are available commercially, and will be apparent to the skilled person. The supports can be manufactured from materials such as glass, ceramics, silica and silicon. Supports with a gold surface may also be used. The supports usually comprise a flat (planar) surface, or at least a structure in which the polynucleotides to be interrogated are in approximately the same plane. Alternatively, the solid support can be non-planar, e.g., a microbead. Any suitable size may be used. For example, the supports might be on the order of 1-10 cm in each direction.

For the grafting reaction to proceed a mixture of the amplification primers is applied to a (suitable functionalised) solid support under conditions which permit reaction between moiety A and the support. The result of the grafting reaction is a substantially even distribution of the primers over the solid support.

In certain embodiments the template to be amplified may be grafted onto the solid support together with the amplification primers in a single grafting reaction. This can be achieved by adding template molecules including moiety A at the 5' end to the mixture of primers to form a primer-template mixture. This mixture is then grafted onto the solid support in a single step. Amplification may then proceed using the immobilised template and primers in a reaction analogous to that described in WO 00/18957. The first step in such a reaction will be hybridisation between surface-bound templates and surface-bound amplification primers.

If the mixture of primers only is grafted onto the solid support and the template to be amplified is present in free solution, the amplification reaction may proceed substantially as described in WO 98/44151. Briefly, following attachment of the primers, the solid support is contacted with the template to be amplified under conditions which permit hybridisation between the template and the immobilised primers. The template is usually added in free solution under suitable hybridisation conditions, which will be apparent to the skilled reader. Typically hybridisation conditions are, for example, 5×SSC at 40° C., following an initial denaturation step. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support. Further rounds of amplification lead to the formation of clusters or colonies of template molecules bound to the solid support.

Sequences S1 and S2 in the amplification primers may be specific for a particular target nucleic acid that it is desired to amplify, but in other embodiments sequences S1 and S2 may be "universal" primer sequences which enable amplification of any target nucleic acid of known or unknown sequence which has been modified to enable amplification with the universal primers.

Suitable templates to be amplified with universal primers may be prepared by modifying target double-stranded polynucleotides by addition of known adaptor sequences to the 5' and 3' ends of the target nucleic acid molecules to be amplified. The target molecules themselves may be any double-stranded molecules it is desired to sequence (e.g., random fragments of human genomic DNA). The adaptor sequences enable amplification of these molecules on a solid support to form clusters using forward and reverse primers having the general structure described above, wherein sequences S1 and S2 are universal primer sequences.

The adaptors are typically short oligonucleotides that may be synthesised by conventional means. The adaptors may be attached to the 5' and 3' ends of target nucleic acid fragments by a variety of means (e.g. subcloning, ligation. etc). More specifically, two different adaptor sequences are attached to a target nucleic acid molecule to be amplified such that one adaptor is attached at one end of the target nucleic acid molecule and another adaptor is attached at the other end of the target nucleic acid molecule. The resultant construct comprising a target nucleic acid sequence flanked by adaptors may be referred to herein as a "template nucleic acid construct". Suitable methods of sample preparation for use in the method described herein are detailed in application number U.S. Ser. No. 11/486,953.

The target double-stranded polynucleotides may advantageously be size-fractionated prior to modification with the adaptor sequences.

The adaptors contain sequences which permit nucleic acid amplification using the amplification primer molecules immobilised on the solid support. These sequences in the adaptors may be referred to herein as "primer binding sequences". In order to act as a template for nucleic acid amplification, a single strand of the template construct must contain a sequence which is complementary to sequence S1 in the forward amplification primers (such that the forward primer molecule can bind and prime synthesis of a complementary strand) and a sequence which corresponds to sequence S2 in the reverse amplification primer molecules (such that the reverse primer molecule can bind to the complementary strand). The sequences in the adaptors which permit hybridisation to primer molecules will typically be around 20-30 nucleotides in length, although the invention is not limited to sequences of this length.

The precise identity of sequences S1 and S2 in the amplification primers, and hence the cognate sequences in the adaptors, are generally not material to the invention, as long as the primer molecules are able to interact with the amplification sequences in order to direct bridging amplification. The criteria for design of primers are generally well known to those of ordinary skill in the art.

Solid-phase amplification by either the method analogous to that of WO 98/44151 or that of WO 00/18957 will result in production of an array of colonies of "bridged" amplification products. Both strands of the amplification product will be immobilised on the solid support at or near the 5' end, this attachment being derived from the original attachment of the amplification primers. Typically the amplification products within each colony will be derived from amplification of a single target molecule.

Amplification methods suitable for the present invention include both thermocycling and isothermal amplifications. In a particular embodiment of the invention, isothermal amplification conditions, as described in application number WO07107710, are used. The lower temperatures used in isothermal amplifications, which simply involve cycles of buffer exchange to change between extension and denaturing conditions, are advantageous due to a higher retention of surface bound molecules, and therefore brighter clusters (i.e, clusters having greater fluorescence intensity following incorporation of a fluorescently labelled nucleotide).

The utility of the sequencing method of the invention is not limited to sequencing of templates produced by an amplification reaction, although this is preferred. The method may be applied to sequencing of double-stranded templates immobilised on a support by any other means amenable to repeated cycles of hybridisation and sequencing.

The invention will be further understood with reference to the following non-limiting experimental examples:

EXAMPLES

The following are examples of general techniques which may be applied in carrying out the method of the invention.

Example 1

Cluster Preparation Using the Detailed Invention

Acrylamide Coating of Glass Chips

The solid supports used are typically 8-channel glass chips such as those provided by Silex Microsystems (Sweden). However, the experimental conditions and procedures are readily applicable to other solid supports.

Chips were washed as follows: neat Decon for 30 min, milliQ H$_2$O for 30 min, NaOH 1N for 15 min, milliQ H$_2$O for 30 min, HCl 0.1N for 15 min, milliQ H$_2$O for 30 min.
Polymer Solution Preparation:
For 10 ml of 2% polymerisation mix.
    10 ml of 2% solution of acrylamide in milliQ H2O
    165 µl of a 100 mg/ml N-(5-bromoacetamidylpentyl) acrylamide (BRAPA) solution in DMF (23.5 mg in 235 µl DMF)
    11.5 µl of TEMED
    100 µl of a 50 mg/ml solution of potassium persulfate in milliQ H$_2$O (20 mg in 400 µl H$_2$O)

The 10 ml solution of acrylamide was first degassed with argon for 15 min. The solutions of BRAPA, TEMED and potassium persulfate were successively added to the acrylamide solution. The mixture was then quickly vortexed and immediately used. Polymerization was then carried out for 1 h 30 min at RT. Afterwards the channels were washed with milliQ H$_2$O for 30 min and filled with 0.1 M potassium phosphate buffer for storage until required.

Example 2

Synthesis of N-(5-bromoacetamidylpentyl) acrylamide (BRAPA) (1)

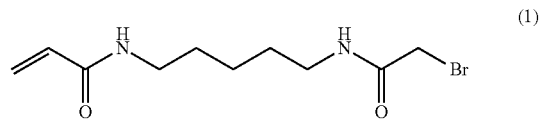

N-Boc-1,5-diaminopentane toluene sulfonic acid was obtained from Novabiochem. The bromoacetyl chloride and acryloyl chloride were obtained from Fluka. All other reagents were Aldrich products.

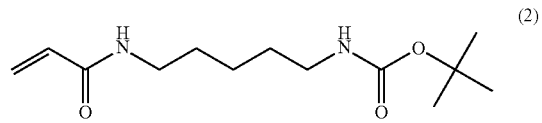 [SMILES: C=CC(=O)NCCCCCNC(=O)OC(C)(C)C]

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, d$_6$-DMSO): 1.20-1.22 (m, 2H, CH$_2$), 1.29-1.43 (m, 13H, tBu, 2×CH$_2$), 2.86 (q, 2H, J=6.8 Hz and 12.9 Hz, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C$_{13}$H$_{24}$N$_2$O$_3$ 256. found 279 (256+Na$^+$).

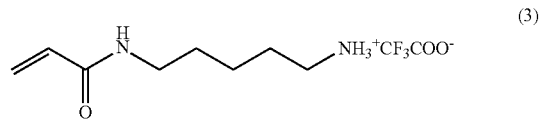

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D$_2$O): 1.29-1.40 (m, 2H, CH$_2$), 1.52 (quint., 2H, J=7.1 Hz, CH$_2$), 1.61 (quint., 2H, J=7.7 Hz, CH$_2$), 2.92 (t, 2H, J=7.6 Hz, CH$_2$), 3.21 (t, 2H, J=6.8 Hz, CH$_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for C$_8$H$_{16}$N$_2$O 156. found 179 (156+Na$^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, d$_6$-DMSO): 1.21-1.30 (m, 2H, CH$_2$), 1.34-1.48 (m, 4H, 2×CH$_2$), 3.02-3.12 (m, 4H, 2×CH$_2$), 3.81 (s, 2H, CH$_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for C$_{10}$H$_{17}$BrN$_2$O$_2$ 276 or 278. found 279 (278+H$^+$), 299 (276+Na$^+$).

Example 3

Grafting Primers onto Surface of SFA Coated Chip

An SFA coated chip is placed onto a modified MJ-Research thermocycler and attached to a peristaltic pump. Grafting mix consisting of 0.5 μM of a forward primer and 0.5 μM of a reverse primer in 10 mM phosphate buffer (pH 7.0) is pumped into the channels of the chip at a flow rate of 60 μl/min for 75 s at 20° C. The thermocycler is then heated to 51.6° C., and the chip is incubated at this temperature for 1 hour. During this time, the grafting mix undergoes 18 cycles of pumping: grafting mix is pumped in at 15 μl/min for 20 s, then the solution is pumped back and forth (5 s forward at 15 μl/min, then 5 s backward at 15 μl/min) for 180 s. After 18 cycles of pumping, the chip is washed by pumping in 5×SSC/5 mM EDTA at 15 μl/min for 300 s at 51.6° C. The thermocycler is then cooled to 20° C.

The primers are typically 5'-phosphorothioate oligonucleotides incorporating any specific sequences or modifications required for cleavage. Their sequences and suppliers vary according to the experiment for which they are to be used, and in this case were complementary to the 5'-ends of the template duplex. The DNA sequence used in this process was a single monotemplate sequence of 240 bases, with ends complementary to the grafted primers. The full sequence of the template duplex is shown in FIG. 6. The duplex DNA was denatured using sodium hydroxide treatment followed by snap dilution as described.

For some of the experiments detailed, the amplified clusters contained a diol linkage in one of the grafted primers. Diol linkages can be introduced by including a suitable linkage into one of the primers used for solid-phase amplification. Synthesis of the diol phosphoramidite is described in Example 4 below. Products containing such diol linkages can be cleaved using periodate and propanolamine as described, and the resulting single stranded polynucleotides hybridised as described.

The grafted primers contain a sequence of T bases at the 5'-end to act as a spacer group to aid linearisation and hybridization. The sequences of the two primers grafted to the chip are designed to enable the appropriate treatment to release the free 3'-hydroxyl moiety, and contain either U base as follows:

```
P5diol:
                                          (SEQ ID NO: 1)
5'PS-TTTTTTTTTT-diol-AATGATACGGCGACCACCGA P7GAU:
                                          (SEQ ID NO: 2)
5' PS-TTTTTTTTTTCAAGCAGAAGACGGCATACGAGAU
```

The same primers can enable cutting with BstNB1, assuming the samples to be amplified contain the relevant recognition site as follows:

```
                                          (SEQ ID NO: 3)
          5' . . . GAGTCNNNNNN . . . 3'

(SEQ ID NO: 4)
          3' . . . CTCAGNNNNNN . . . 5'
```

To enable the cutting with the remote cutting restriction enzyme Mme1; the ends of both the grafting primers contained the following sequence:

```
              5' . . . TCCGAC-3'
```

To enable the cutting with the remote cutting restriction enzyme EcoP15; the ends of both the grafting primers contained the following sequence:

```
              5' . . . CAGCAG-3'
```

The design of the primers is shown in FIGS. 5 and 6

Example 4

Preparation of Diol-Phosphoramidite for DNA Coupling

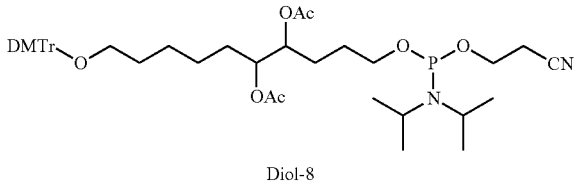

Diol-8

Step 1:

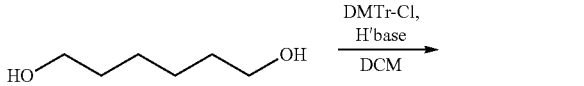

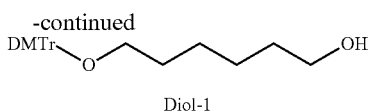

Diol-1

1,6-Hexanediol (Sigma Aldrich 99%) (14.6 g, 124 mmol), N,N-diisopropylethylamine (Hünig's base; Sigma Aldrich; redistilled) (21.6 mL, 124 mmol) is dissolved in anhydrous DCM/DMF (250/50 mL) under $N_2$. The solution is cooled to 0° C. and the first portion of 4,4'-dimethoxytrityl chloride (DMTr-Cl; Sigma-Aldrich 95%) (10.5 g, 31 mmol) is added. The reaction mixture is then warmed to room temperature. After stirring for 1 h, the reaction mixture is cooled to 0° C. again and the second portion of DMTr-Cl (10.5 g, 31 mmol) is added and then allowed to stir at room temperature for other 2 hours. TLC (EtOAc: petroleum ether 4:6) analysis indicates ca. 95% consumption of starting material derivative (DMTr-OH). The reaction is concentrated under reduced pressure and Aq. $NaHCO_3$ (sat.) solution (500 mL) is poured into the residue. The resulting mixture is extracted with petroleum ether/EtOAc (2:1) (3×1000 mL). The combined organic layers are dried over $MgSO_4$, and concentrated under vacuum. The residue is co-evaporated with xylene (2×100 mL) to remove DMF. The reaction mixture, is pre-absorbed on silica gel and subjected to flash chromatography using solvents containing 1% $Et_3N$ petroleum ether to petroleum ether/EtOAc (7:3) as eluent. The yield of pale yellow oil is 16.58 g, 64%, with a further 7.8 g (17%) of the bis-tritylated by-product.

TLC: $R_f$: 0.35 (diol-1); $R_f$: 0.7 (bis-tritylated by-product) (petroleum ether/EtOAc 6:4).

$^1$H NMR (400 MHz, $CDCl_3$): δ 1.32-1.44 (m, 4H, 2×$CH_2$), 1.54-1.68 (m, 4H, 2×$CH_2$), 3.06 (t, J=6.6 Hz, 2H, $CH_2O$), 3.62-3.68 (m, 2H, $CH_2OH$), 3.81 (s, 6H, 2× MeO), 6.83-6.85 (m, 4H, Ph), 7.24-7.35 (m, 7H, Ph), 7.45-7.47 (m, 2H, Ph).

Step 2:

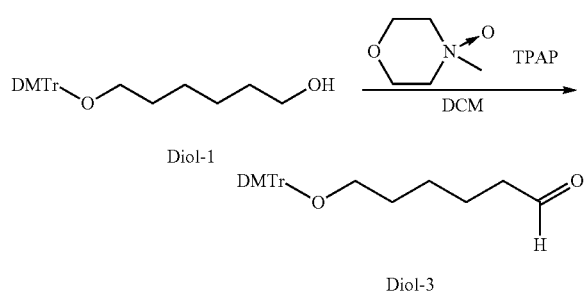

To a solution of Diol-1 (16.6 g, 39.5 mmol) in anhydrous DCM (200 mL), tetrapropylammonium perruthenate (TPAP; Sigma Aldrich 97%) (277 mg, 0.79 mmol) is added under $N_2$ atmosphere. The solution is cooled to 0° C. and N-methylmopholine N-oxide (Sigma Aldrich 97%) (2.7 g, 23 mmol) is added. The reaction is warmed to room temperature. After 1 hour, the other three portions of N-methylmopholine N-oxide (3×2.0 g, 51.2 mmol) are added within a period of four hours. TLC (EtOAc: petroleum ether 4:6) indicates the reaction goes to completion. The reaction is quenched with aq. $NaHCO_3$ (sat.) (1000 mL) and extracted to $CH_2Cl_2$ (4×1000 mL). The combined organic layers are dried over $MgSO_4$. The solution is concentrated under reduced pressure. Diol-3, 9.9 g, 60%, is isolated by flash chromatography using solvents containing 1% $Et_3N$ from petroleum ether to petroleum ether/EtOAc (6:4) as eluent, as a pale yellow oil.

TLC: $R_f$: 0.7 (petroleum ether/EtOAc 6:4).

$^1$H NMR (400 MHz, $CDCl_2$): δ 1.30-1.37 (m, 2H, $CH_2$), 1.48-1.57 (m, 4H, 2×$CH_2$), 2.34 (td, J=1.7 and 7.4 Hz, 2H, $CH_2CHO$), 2.97 (s, 2H, $CH_2O$), 3.72 (s, 6H, 2× MeO), 6.73-6.76 (m, 4H, Ph), 7.10-7.26 (m, 7H, Ph), 7.34-7.36 (m, 2H, Ph), 9.67 (t, J=1.7, 1H, CHO).

Step 3:

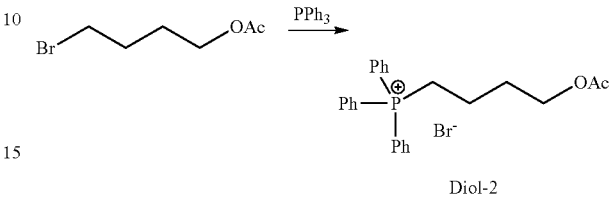

A solution of triphenylphosphine (Sigma-Aldrich 99%, ReagentPlus™). (39.3 g, 150 mmol) and 4-bromobutyl acetate (Sigma-Aldrich) (26 mL, 180 mmol) in anhydrous toluene (300 mL) is heated under reflux for 36 hours under $N_2$ in an oil-bath (140° C.). During the reflux, oil is precipitated out. The reaction mixture is cooled to room temperature. TLC (petroleum ether/EtOAc 7:3) analysis of the toluene solution showed that there is still triphenylphosphine ($R_f$: 0.8) left. The supernatant is decanted into another round-bottomed flask and concentrated down to the approximate volume of 30 mL. The solution is heated under reflux again for another 12 hours. The supernatant is decanted. The portions of oil are combined together, dissolved in water (500 mL) and extracted with EtOAc (2×500 mL). The combined organic layers are back-extracted with water (150 mL). Two lots of aqueous layers are combined, evaporated under reduced pressure. The resulting residue is co-evaporated with acetonitrile (2×100 mL) to give 78.4 g, 95% yield of a pale yellow oil. NMR indicates that the product is pure, and is used for the next step reaction without further purification.

TLC: $R_f$: 0.0 (petroleum ether/EtOAc 7:3).

$^1$H NMR (400 MHz, $CDCl_3$): δ 1.63-1.73 (m, 2H, $CH_2$), 1.94 (s, 3H, 2×$CH_3$), 2.06-2.16 (m, 2H, $CH_2$), 3.97-4.05 (m, 2H, $CH_2P$), 4.11 (t, J=6.0, 2H, $CH_2O$), 7.69-7.95 (m, 15H, Ph).

$^{31}$P NMR (162 MHz, $CDCl_3$): 25.9 ppm.

Mass spec details: LC-MS (Electrospray positive): ($M^+$) 377.

Step 4:

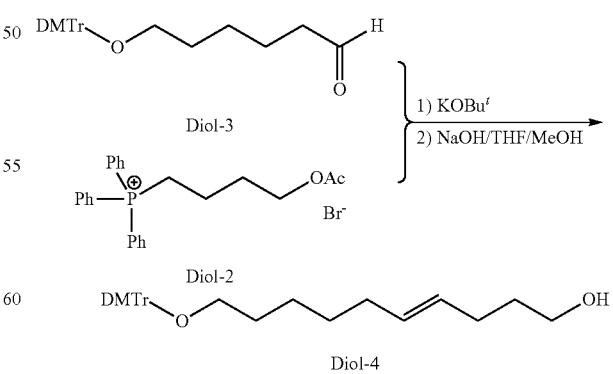

Diol-2 (10.34 g, 22.7 mmol) is weighed into a round-bottomed flask and dissolved with DCM (20 mL). The solution is then evaporated under reduced pressure until it gives a white foam. The flask is then subjected to high vacuum for 24 h. To this flask, anhydrous THF (180 mL) is added under $N_2$. The resulting suspension is cooled to −78° C. with an acetone-dry ice bath. With vigorous stirring, KOBu$^t$ (3.3 g, 29.5 mmol) is added under $N_2$. Slowly the colour of the suspension turns orange, and white solids are gradually precipitated out. To this suspension, a solution of diol-3 (dried at 60° C. under high vacuum for 1 h before the reaction), (9.5 g, 22.7 mmol) in THF (50 mL) is added drop wise over half an hour. Acetone-dry ice bath is then removed. The reaction mixture is slowly warmed to room temperature and stirred for another hour. The colour of the reaction mixture turns yellow after the addition of diol-3. The reaction mixture is concentrated down under reduced pressure. The resulting residue is partitioned between DCM (800 mL) and aq. NaCl (sat.) (800 mL). The aqueous layer is extracted with an additional DCM (2×800 mL). The organic extractions are combined, dried over $MgSO_4$, filtered, and evaporated under reduced pressure to give yellow oil. The oil is dissolved in THF/MeOH (125/100 mL) and cooled to 0° C. To this solution, NaOH (1M in $H_2O$, 25 mL) is added. After allowing the reaction to stir for 1 hour, TLC analysis indicates full consumption of starting material. The reaction mixture is neutralized with acetic acid (1.5 mL). The reaction mixture is concentrated down under reduced pressure. The resulting residue is partitioned between DCM (800 mL) and aq. $NaHCO_3$ (sat.) (800 mL). The aqueous layer is extracted with additional DCM (2×800 mL). The organic extractions are combined, dried over $MgSO_4$, filtered, and evaporated to give a pale yellow oil. Diol-4, 6.45 g, 60% is isolated by flash chromatography using solvents containing 1% $Et_3N$ from petroleum ether to petroleum ether/EtOAc (5:5) as eluent, as a light yellow oil.

TLC: $R_f$=0.45 (petroleum ether/EtOAc 6:4).

$^1$H NMR (400 MHz, $CDCl_3$) δ 1.24-1.32 (m, 4H, 2×$CH_2$), 1.54-1.57 (m, 4H, 2×$CH_2$), 1.93-1.96 (m, 2H, $CH_2$), 2.02-2.07 (m, 2H, $CH_2$), 2.96 (t, J=6.6 Hz, 2H, $CH_2O$), 3.54-3.59 (m, 2H, $CH_2OH$), 3.72 (s, 6H, 2× MeO), 5.29-5.32 (m, 2H, 2× =CH), 6.73-6.77 (m, 4H, Ph), 7.11-7.27 (m, 7H, Ph), 7.36-7.38 (m, 2H, Ph).

Step 5:

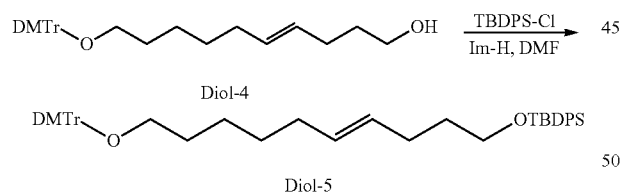

To a solution of Diol-4 (5.68 g, 12 mmol) and imidazole (Sigma Aldrich, 99%), (1.63 g, 24 mmol) in anhydrous DMF (100 mL), t-butyldiphenylsilyl chloride (Sigma Aldrich, 98%), (4.05 mL, 15.6 mmol) is added drop wise under $N_2$ atmosphere at room temperature. The reaction is stirred for 1 hour. TLC (petroleum ether/EtOAc 8:2) indicates that the starting material is fully consumed. A saturated aq. $NaHCO_3$ solution (500 mL) is added to quench the reaction. The resulting mixture is extracted with petroleum ether/EtOAc (2:1) (3×500 mL). The organic layers are combined, dried over $MgSO_4$, filtered, and evaporated to give a yellow oil. Diol-5, 8.14 g, 95% is isolated by flash chromatography using solvents containing 1% $Et_3N$ from petroleum ether to petroleum ether/EtOAc (9:1) as eluent, as a colourless oil.

TLC: $R_f$=0.7 (petroleum ether:EtOAc 8:2).

$^1$H NMR (400 MHz, $CDCl_3$): δ 0.97 (s, 9H, 3× Me), 1.19-1.30 (m, 4H, 2×$CH_2$), 1.48-1.55 (m, 4H, 2×$CH_2$), 1.91-1.95 (m, 2H, $CH_2$), 2.01-2.06 (m, 2H, $CH_2$), 2.95 (t, J=6.6 Hz, 2H, $CH_2O$), 3.58 (t, J=6.3 Hz, 2H, $CH_2O$), 3.70 (s, 6H, 2× MeO), 5.24-5.27 (m, 2H, 2× =CH), 6.72-6.75 (m, 4H, Ph), 7.11-7.37 (m, 15H, Ph), 7.57-7.60 (m, 4H, Ph).

Step 6:

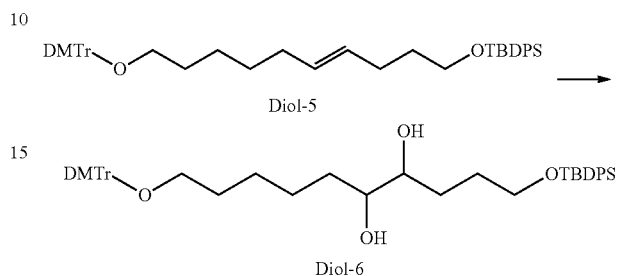

A mixture of diol-5 (9.27 g, 13 mmol), AD-mix-α (Sigma Aldrich), (18.2 g), methanesulfonamide (Sigma Aldrich, 97%), (1.23 g, 13 mmol), t-BuOH (65 mL) and water (65 mL) is stirred together vigorously at 55° C. for 14 h. The TLC analysis (petroleum ether:EtOAc 6:4) indicates ca. 95% consumption of the starting material. The reaction mixture is cooled to room temperature, treated with sodium sulfite (15.3 g, 12 mmol), then further stirred for 30 min. A saturated aq. $NaHCO_3$ solution (500 mL) is added to the reaction. The resulting mixture is extracted with EtOAc (3×500 mL). The organic layers are combined, dried over $MgSO_4$, filtered, and evaporated to give yellow oil. Diol-6, 7.96 g, 82%, is isolated by flash chromatography (silica gel, Fluka, 70-230 mesh) using solvents containing 1% $Et_3N$ from petroleum ether to petroleum ether/EtOAc (1:1) as elutant, as a white solid.

TLC: $R_f$=0.3 (petroleum ether:EtOAc 6:4).

$^1$H NMR (400 MHz, $CDCl_3$) δ 1.07 (s, 9H, 3× Me), 1.41-1.7 (m, 12H, 6×$CH_2$), 1.94 (d, J=4.3 Hz, 1H, OH), 2.94-2.95 (m, 1H, OH), 3.06 (t, J=6.6 Hz, 2H, $CH_2O$), 3.61-3.63 (m, 2H, 2×CHOH), 3.73 (t, J=5.6 Hz, 2H, $CH_2O$), 3.81 (s, 6H, 2× MeO), 5.24-5.27 (m, 2H, 2× =CH), 6.82-6.85 (m, 4H, Ph), 7.21-7.47 (m, 15H, Ph), 7.57-7.60 (m, 4H, Ph).

Step 7:

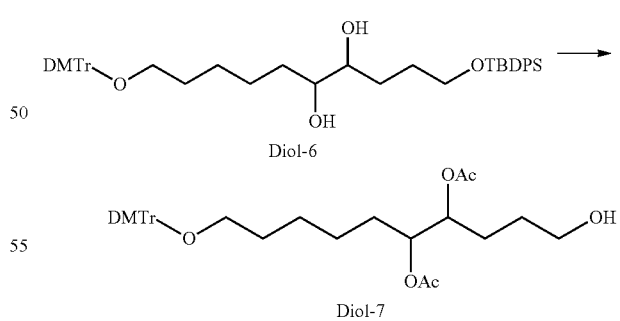

To a solution of diol-6 (7.96 g, 13 mmol) and DMAP (Sigma-Aldrich ReagentPlus™, 99%). (260 mg, 2.13 mmol) in a mixture of pyridine (15 mL) and DCM (30 mL), acetic anhydride (Fluka 99%), (2.5 mL, 26.68 mmol) is added at room temperature. TLC analysis (petroleum ether:EtOAc 6:4) indicates full consumption of the starting material after 1 h. The reaction is quenched by saturated aq. $NaHCO_3$ solution (500 mL). After 5 min. the mixture is extracted with DCM (3×500 mL). The organic layers are combined, dried over MgSO$_4$, filtered, and evaporated. The residue is co-evaporated with toluene (2×100 mL). The resulting yellow oil is subjected to a plug of silica gel (50 g, Fluka, 70-230 mesh) to remove DMAP using eluents containing 0.1% Et$_3$N from petroleum ether to petroleum ether/EtOAc (7:3) (250 mL each). The combined fractions of product are concentrated to dryness. The resulting colourless oil is dissolved in THF (100 mL) and treated with TBAF (Sigma-Aldrich; 5% wt water), (1 M in THF, 15 mL) at 0° C. The reaction solution is slowly warmed to room temperature and stirred for 2 hours. TLC analysis (petroleum ether:EtOAc 6:4) indicates that desilylation is completed. The volatile solvent (THF) is evaporated under reduced pressure at low temperature. A saturated aq. NaHCO$_3$ solution (500 mL) is added to the residue. The resulting mixture is extracted with EtOAc (3×500 mL). The organic layers are combined, dried over MgSO$_4$, filtered, and evaporated to give yellow oil. Diol-7, 4.2 g, 66%, is isolated by flash chromatography using solvents containing 1% Et$_3$N from petroleum ether to petroleum ether/EtOAc (1:1) as elutant, as a white solid.

TLC: R$_f$=0.45 (petroleum ether:EtOAc 1:1).

$^1$H NMR (400 MHz, CDCl$_3$) δ 1.29-1.33 (m, 4H, 2×CH$_2$), 1.47-1.63 (m, 8H, 4×CH$_2$), 1.99, 2.01 (2 s, 6H, 2 MeC(O)), 3.00 (t, J=6.5 Hz, 2H, CH$_2$O), 3.60-3.64 (m, 2H, CH$_2$O), 3.75 (s, 6H, 2× MeO), 4.92-4.97 (m, 2H, 2× CHOAc), 6.76-6.80 (m, 4H, Ph), 7.15-7.29 (m, 7H, Ph), 7.38-7.40 (m, 2H, Ph).

Step 8:

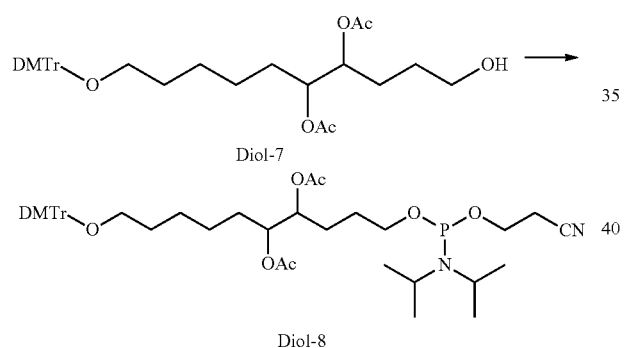

To a solution of diol-7 (2.08 g, 3.5 mmol) and diisopropylethylamine (Sigma Aldrich), (1.53 ml, 8.75 mmol) in DCM (17 mL), 2-cyanoethyl N,N-diisopropylchlorophosphoramidite (1.0 g, 4.2 mmol) is added drop wise at room temperature under N$_2$. After stirring for 1 hour, TLC analysis (petroleum ether:EtOAc 4:6) indicates the full consumption of the starting material. The solvent (THF) is concentrated under reduced pressure. The resulting residue is subjected to chromatography directly. Diol-8, 2.5 g, 90%, is isolated by flash chromatography using solvents containing 1% Et$_3$N from petroleum ether to petroleum ether/EtOAc (1:1) as eluent, as a colourless syrup.

TLC: R$_f$=0.55 (petroleum ether:EtOAc 4:6).

$^1$H NMR (400 MHz, CDCl$_3$) δ 1.09, 1.10, 1.11, 1.12 (4 s, 12H, N(CHMe$_2$)$_2$), 1.26-1.31 (m, 4H, 2×CH$_2$), 1.45-1.56 (m, 8H, 4×CH$_2$), 1.95, 1.969, 1.971, 1.98 (4 s, 6H, 2 MeCO), 2.56 (t, J=6.5 Hz, 2H, CH$_2$CN), 2.95 (t, J=6.5 Hz, 2H, CH$_2$O), 3.49-3.55 (m, 4H, CH$_2$O), 3.72 (s, 6H, 2× MeO), 4.89-4.92 (m, 2H, 2× CHOAc), 6.74-6.76 (m, 4H, Ph), 7.13-7.25 (m, 7H, Ph), 7.34-7.37 (m, 2H, Ph).

$^{31}$P NMR (162 MHz, CDCl$_3$): 148.67, 148.69 ppm.

Example 5

Preparation of Clusters by Isothermal Amplification

Step 1: Hybridisation and Amplification

The DNA sequence used in the amplification process is a single monotemplate sequence of 240 bases, with ends complementary to the grafted primers. The full sequence of one strand of the template duplex is shown in FIG. 6. The duplex DNA (1 nM) is denatured using 0.1 M sodium hydroxide treatment followed by snap dilution to the desired 0.2-2 pM 'working concentration' in 'hybridization buffer' (5×SSC/0.1% Tween).

Surface amplification was carried out by isothermal amplification using an MJ Research thermocycler, coupled with an 8-way peristaltic pump Ismatec IPC ISM931 equipped with Ismatec tubing (orange/yellow, 0.51 mm ID). A schematic of the instrument is shown below.

The single stranded template is hybridised to the grafted primers immediately prior to the amplification reaction, which thus begins with an initial primer extension step rather than template denaturation. The hybridization procedure begins with a heating step in a stringent buffer to ensure complete denaturation prior to hybridisation. After the hybridization, which occurs during a 20 min slow cooling step, the flowcell was washed for 5 minutes with a wash buffer (0.3×SSC/0.1% Tween).

Figure 13:
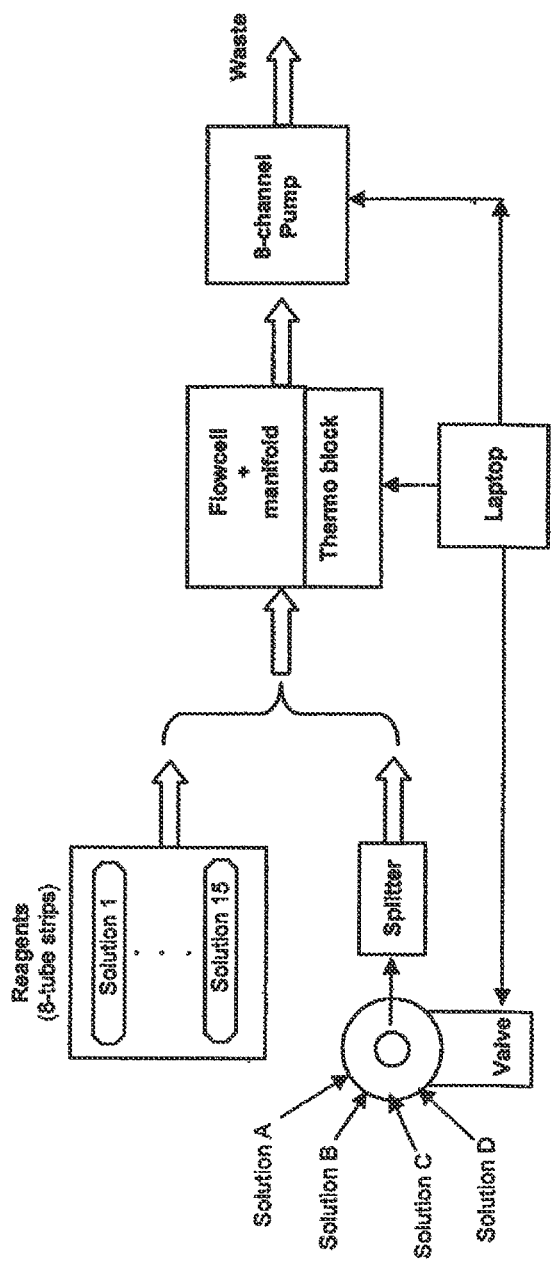
FIG. 13 shows a schematic of a typical amplification process.

A typical amplification process is detailed in FIG. 13, detailing the flow volumes per channel.

1. Template Hybridization and 1$^{st}$ Extension

| Step | Description | T (° C.) | Time (sec) | Flow rate (μl/min) | Pumped V (μl) |
|---|---|---|---|---|---|
| 1 | Pump Hybridization pre-mix | 20 | 120 | 60 | 120 |
| 2 | Pump Hybridization mix | 98.5 | 300 | 15 | 75 |
| 3 | Remove bubbles | 98.5 | 10 | 100 | 16.7 |
| 4 | Stop flow and hold T | 98.5 | 30 | static | 0 |
| 5 | Slow cooling | 98.5-40.2 | 19.5 min | static | 0 |
| 6 | Pump wash buffer | 40.2 | 300 | 15 | 75 |
| 7 | Pump amplification pre-mix | 40.2 | 200 | 15 | 50 |
| 8 | Pump amplification mix | 40.2 | 75 | 60 | 75 |
| 9 | First Extension | 74 | 90 | static | 0 |
| 10 | cool to room temperature | 20 | 0 | static | 0 |

2. Isothermal Amplification

| Step | Description | T (° C.) | Time (sec) | Flow rate (μl/min) | Pumped V (μl) |
|---|---|---|---|---|---|
| (1) | Pump Formamide | 60 | 75 | 60 | 75 |
| This sequence 35 times | Pump Amplification pre-mix | 60 | 75 | 60 | 75 |
| | Pump Bst mix | 60 | 95 | 60 | 95 |
| | Stop flow and hold T | 60 | 180 | static | 0 |
| 2 | Pump wash buffer | 60 | 120 | 60 | 120 |

Hybridisation pre mix (buffer)=5×SSC/0.1% Tween
Hybridisation mix=0.1 M hydroxide DNA sample, diluted in hybridisation pre mix
Wash buffer=0.3×SSC/0.1% tween
Amplification pre mix=2 M betaine, 20 mM Tris, 10 mM Ammonium Sulfate, 2 mM Magnesium sulfate, 0.1% Triton, 1.3% DMSO, pH 8.8

Amplification mix=2 M betaine, 20 mM Tris, 10 mM Ammonium Sulfate, 2 mM Magnesium sulfate, 0.1% Triton, 1.3% DMSO, pH 8.8 plus 200 µM dNTP's and 25 units/mL of Taq polymerase (NEB Product ref M0273L)

Bst mix=2 M betaine, 20 mM Tris, 10 mM Ammonium Sulfate, 2 mM Magnesium sulfate, 0.1% Triton, 1.3% DMSO, pH 8.8 plus 200 µM dNTP's and 80 units/mL of Bst polymerase (NEB Product ref M0275L).

Step 2: Blocking Extendable 3'-OH Groups

To prepare the blocking pre-mix, 1530 µL of water and 170 µL of 10× blocking buffer (NEB buffer 4; product number B7004S) are mixed for a final volume of 1700 µL. To prepare the blocking mix 1065.13 µL of blocking pre-mix, 21.12 µL of 125 µM ddNTP mix, and 13.75 µL of TdT terminal transferase (NEB; part no M0252S) are mixed for a final volume of 1100 µL.

To block the nucleic acid within the clusters formed in the flow cell channels, the computer component of the instrumentation flows the appropriate blocking buffer through the flow cell, and controls the temperature as shown in the exemplary embodiments below.

| Step | Description | T (° C.) | Time (sec) | Flow rate (µl/min) | Pumped V (µl) |
|---|---|---|---|---|---|
| 1 | Pump Blocking pre-mix | 20 | 200 | 15 | 50 |
| 2 | Pump Blocking mix | 37.7 | 300 | 15 | 75 |
| 3 | Stop flow and hold T | 37.7 | 20 | static | 0 |
| 4 | Cyclic pump Blocking mix and wait | 37.7 | 8 × (20 + 180) | 15/static | 45 |
| 5 | Pump wash buffer | 20 | 300 | 15 | 75 |

Example 6

Treatment of Clusters to Obtain a Free 3'-Hydroxyl Group

Method a: USER™

The amplified clusters were treated on the MJ platform to the following conditions; flow with USER premix (10 mM KCl, 20 mM Tris-HCl (pH 8.8) 10 mM $(NH_4)_2SO_4$, 2 mM $MgSO_4$, 0.1% Triton-X 100) for 5 min at 38° C.; flow with USER buffer (User premix plus 10 units/mL USER enzyme mix (NEB cat #M5505) for 5 mins and incubate for 45 min at 38° C.; wash in wash buffer for 5 mins.

The cleaved strands were treated with T7 exonuclease (100 units/mL in NEB buffer 4 (1×NEB4=50 mM potassium acetate, 20 mM Tris-acetate, 10 mM Magnesium acetate, 1 mM DTT pH 7.9) for 30 mins at 30° C. and flushed with wash buffer.

The strands were extended by ligation of SBS 5 ligation primer:

(SEQ ID NO: 5)
3'-GTAGCTGAGCCAAGTCGTCCTTACGGCTCTGGCT-PO4-5'

The primer (1 µM) in hybridization pre mix was flowed into the cell at 60° C. and allow to hybridise for 5 mins. The cell was flushed with T4 ligation buffer and cooled to 30° C. T4 DNA ligase was added, and the reaction held for 30 mins before flushing with wash buffer. The 3'-end of the hybridized ligated SBS 5 primer is available for subsequent extension reactions.

Method b: Nt.BstNBI

The amplified clusters were treated on the MJ platform with the following conditions; the flow cells were washed with NEB buffer 3 at 55° C. for 5 mins at 15 µl/min, then treated with 50 µl of Nt.BstNBI (1×NEB buffer 3; final enzyme conc 1000 units/mL). The cell was incubated for 1 hr at 55° C. then lowered to 20° C. flushed with NEB buffer 3 (5 min at 15 µl/min), then wash buffer (5 min at 15 µl/min).

The cleaved strands were treated with T7 exonuclease (100 units/mL in NEB buffer 4 (1×NEB4=50 mM potassium acetate, 20 mM Tris-acetate, 10 mM Magnesium acetate, 1 mM DTT pH 7.9) for 30 mins at 30° C. and flushed with wash buffer.

Example 7

Sequencing from an Immobilized Primer

Sequencing of the clusters from the above illustrative protocol was carried out using modified nucleotides prepared as described in International patent application WO 2004/018493, and labeled with four spectrally distinct fluorophores, as described in U.S. application No. 60/801,270; filed May 18 2006. Sequencing of clusters is described in more detail in patent WO06064199.

A mutant 9° N polymerase enzyme (an exo-variant including the triple mutation L408Y/Y409A/P410V and C223S) was used for the nucleotide incorporation steps.

Incorporation mix, Incorporation buffer (50 mM Tris-HCl pH 8.0, 6 mM $MgSO_4$, 1 mM EDTA, 0.05% (v/v) Tween –20, 50 mM NaCl) plus 110 nM YAV exo-C223S, and 1 µM each of the four labeled modified nucleotides, was applied to the clustered templates, and heated to 45° C.

Templates were maintained at 45° C. for 30 min, cooled to 20° C. and washed with Incorporation buffer, then with 5×SSC/0.05% Tween 20. Templates were then exposed to Imaging buffer (100 mM Tris pH7.0, 30 mM NaCl, 0.05% Tween 20, 50 mM sodium ascorbate, freshly dissolved). Templates were scanned in 4 colors at room temp. Templates were then exposed to sequencing cycles of Cleavage and Incorporation as follows:

Cleavage: Prime with Cleavage buffer (0.1M Tris pH 7.4, 0.1M NaCl and 0.05% Tween 20), 125 µL/channel; 60 Heat to 60° C.
Treat the clusters with Cleavage mix (100 mM TCEP in Cleavage buffer), 75 µL/channel; 60 µL/min.
Wait for a total of 15 min in addition to pumping fresh cleavage mix, 25 µL/channel; 60 µL/min, every 4 min.
Cool to 20° C.
Wash with Enzymology buffer.
Wash with 5×SSC/0.05% Tween 20.
Prime with Imaging buffer.
Scan in 4 colors at RT.
Incorporation: Prime with Incorporation buffer, 125 µL/channel; 60 µL/min, Heat to 60° C.
Treat with Incorporation mix, 75 µL/channel; 60 µL/min.
Wait for a total of 15 min in addition to pumping fresh Incorporation mix, 25 µL/channel; 60 µL/min, every 4 min.
Cool to 20° C.
Wash with Incorporation buffer, 75 µL/channel; 60 µL/min.
Wash with 5×SSC/0.05% Tween 20, 75 µL/channel; 60 µL/min
Prime with imaging buffer, 100 µL/channel; 60 µL/min
Scan in 4 colors at RT.
Repeat the process of Incorporation and Cleavage for as many cycles as required.

Incorporated nucleotides were detected using a Total Internal Reflection based fluorescent CCD imaging apparatus described in "Systems and Devices for Sequence by Synthesis Analysis," U.S. Ser. No. 60/788,248, filed Mar. 31, 2006.

A representative image showing two cycles of incorporation is shown in FIG. 7. The first cycle of incorporation (top right) shows an image with 3271 clusters that have incorporated a G triphosphate according to the monotemplate sequence. The second cycle (bottom right), shows an image of the second cycle where 3235 clusters have incorporated an A triphosphate. The main picture shows the colocalised image, where 3058 of the clusters are common to both images, showing that the clusters can go through cycles of sequencing from the immobilized primer.

Example 8

Extension with Unlabelled Nucleotides

After the final deblock step of the sequencing protocol, the array was treated to a round of extension with four dNTP's and Bst polymerase, analogous to a cycle of extension in the cluster generation process. The array was treated as follows:

| Description | T (° C.) | Time (sec) | Flow rate (µl/min) | Pumped V (µl) |
|---|---|---|---|---|
| Pump Amplification pre-mix | 60 | 75 | 60 | 75 |
| Pump Bst mix | 60 | 95 | 60 | 95 |
| Stop flow and hold T | 60 | 180 | static | 0 |
| Pump wash buffer | 60 | 120 | 60 | 120 |

Example 9

Treatment to Excise the Central Region of a Cluster

Clusters were treated with Mme1, followed by T4 polymerase to remove the dinucleotide overhangs, and T4 ligase to join the polished, blunt ends in a 36 base pair sequence. Identical protocols have been described in solution on circular vector constructs, (*Nature Methods,* 2, 105-111 (2005)), and the methods were repeated on the amplified clusters, using buffer conditions and temperatures as recommended for the appropriate enzyme.

Example 10

Linearisation and Hybridization of a Sequencing Primer

To prepare the linearization mix 1429 uL of water, 64 mg of sodium periodate, 1500 uL of formamide, 60 uL of 1M Tris pH8, and 6011.4 uL of 3-aminopropanol are mixed for a final volume of 3 mL. The periodate is first mixed with the water while the Tris is mixed with the formamide. The two solutions are then mixed together and the 3-aminopropanol is added to that mixture.

To linearize the nucleic acid within the clusters formed within the flow cell channels, 300 µL per channel of linearisation mix is flowed in at 15 µL/min at 20° C.; followed by 75 µL of water at the same flow rate.

To prepare the primer mix, 895.5 µL of hybridization buffer and 4.5 µl of sequencing primer (100 µM) are mixed to a final volume of 900 µL. The sequence of the sequencing primer used in this reaction was:

(SEQ ID NO: 6)
5'-ACACTCTTTCCCTACACGACGCTCTTCCGATC

To denature the nucleic acid within the clusters and to hybridize the sequencing primer, the following reagents are flowed through the cell:

| Step | Description | T (° C.) | Time (sec) | Flow rate (µl/min) | Pumped V (µl) |
|---|---|---|---|---|---|
| 1 | Pump 0.1M NaOH | 20 | 300 | 15 | 75 |
| 2 | Pump TE | 20 | 300 | 15 | 75 |
| 3 | Pump Primer mix | 20 | 300 | 15 | 75 |
| 4 | Hold at 60 C. | 60 | 900 | 0 | 0 |
| 5 | Pump wash buffer | 40.2 | 300 | 15 | 75 |

Example 11

Sequencing from a Non-Immobilised Primer

The sequencing process was carried out in exactly the same way as described in Example 7. The second read can be aligned with the first, in the case of two reads, or the sequencing process was carried out for 36 cycles in the case of Mme1 treatment. This single read generated 18 bases of information for each end of the original fragment.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

Example 12

Paired Reads from a Library of Fragments

The following experimental details describe the complete exposition of one embodiment of the invention as described above.

The library was made using purified human BAC DNA (140 k human chromosome 6 insert cloned into a pTARBAC vector). The DNA was first prepared for ligation to forked adaptors by: fragmentation of the DNA by nebulisation, end repair of the DNA ends to make them blunt-ended and phosphorylated, then the addition of a single 'A' nucleotide onto the 3' ends of the DNA fragments. The ligation reaction was performed with the prepared fragmented DNA and adaptors pre-formed by annealing 'Oligo A' and 'Oligo B' (sequences given below). The product of the reaction was isolated/purified from unligated adaptor by gel electrophoresis. Finally, the product of the ligation reaction was subjected to cycles of PCR to selectively amplify ligated product that contained genomic DNA with adaptor at both ends of the fragments.

Materials and Methods
Step 1) Nebulization
Materials:
 0.5 ug/ul Human BAC DNA (140 k human chromosome 6 insert cloned into a pTARBAC vector)
 Nebulization Buffer (53.1 ml glycerol, 42.1 ml water, 3.7 ml 1 M Tris HCl pH7.5, 1.1 ml 0.5 M EDTA)
 TE
 Nebulizers (Invitrogen, K7025-05)
 PCR purification kit columns (Qiagen, 28104)
Procedure:
 Mixed 10 µl (5 µg) of BAC DNA with 40 µl of TE and 700 µl of nebulization buffer. Chilled DNA solutions were each fragmented in a nebulizer on ice for 6 minutes under 32 pounds per square inch (psi) of pressure. The recovered volumes were each purified with a Qiagen PCR purification kit column and eluted in 30 µl of EB.

Step 2) End-Repair
 Materials:
 Nebulized DNA (from Step 1)
 Water
 T4 DNA ligase buffer with 10 mM ATP (10×) (NEB, B0202S)
 dNTPs mix (10 mM each) (NEB, N0447S)
 T4 DNA Polymerase (3 U/ul) (NEB, M0203L)
 E. coli DNA Pol I large fragment (Klenow) (5 U/ul) (NEB, M0210S)
 T4 polynucleotide kinase (10 U/ul) (NEB, M0201L)
 PCR purification kit columns (Qiagen, 28104)
Procedure:
 End repair mix was assembled as follows:

| | |
|---|---|
| Nebulized DNA | 30 µl |
| Water | 45 µl |
| T4 DNA ligase buffer with 10 mM ATP | 10 µl |
| dNTPs | 4 µl |
| T4 DNA pol | 5 µl |
| Klenow DNA pol | 1 ul |
| T4 PNK | 5 ul |
| | 100 µl total |

The reaction was incubated for 30 mins at room temperature. The DNA was purified on a Qiagen column, eluting in 30 µl EB.

Step 3) A-Tailing Reaction
 Materials:
 End repaired DNA (from Step 2)
 Water
 NEB buffer 2 (10×) (NEB, B7002S)
 dATP (1 mM) (Amersham-Pharmacia, 272050)
 Klenow fragment (3' to 5' exo minus) (5 U/µl) (NEB, M0212B)
 Hot block or PCR machine
 MinElute PCR purification kit column (Qiagen, 28004)
Procedure:
 The following reaction mix was assembled:

| | |
|---|---|
| End repaired DNA | 30 µl |
| Water | 2 ul |
| NEB buffer 2 | 5 µl |
| dATP | 10 µl |
| Klenow fragment (3' to 5' exo minus) | 3 µl |
| | 50 µl total |

The reaction was incubated for 30 min at 37° C., then the DNA purified on a Qiagen MinElute column, eluting in 10 µl EB.

Step 4) Annealed Adaptors
 Materials:
 Oligo A: 5'ACACTCTTTCCCTACACGACGCTCTTC-CGATCxT (x=phosphorothioate bond) (SEQ ID NO:7)
 Oligo B: 5'Phosphate-GATCGGAAGAGCGGTTCAG-CAGGAATGCCGAG (SEQ ID NO:8)
 50 mM Tris/50 mM NaCl pH7.0
 PCR machine
Procedure:
 The oligos were mixed together to a final concentration of 15 µM each, in 10 mM Tris/10 mM NaCl pH 7.0. The adaptor strands were annealed in a PCR machine programmed as follows: Ramp at 0.5° C./sec to 97.5° C.; Hold at 97.5° C. for 150 sec; then a step of 97.5° C. for 2 sec with a temperature drop of 0.1° C./cycle for 775 cycles.

Step 5) Ligation
 Materials:
 A-tailed genomic DNA (from Step 3)
 Quick ligase buffer (2×) (NEB, B2200S)
 Annealed adaptor (15 µM) (from 4.)
 Quick Ligase (1 U/µl) (NEB, M2200L)
 PCR purification kit columns (Qiagen, 28104)
Procedure:
 Reaction mix was assembled as follows:

| | |
|---|---|
| A-tailed genomic DNA | 10 µl |
| Quick ligase buffer | 25 µl |
| Annealed adaptor | 10 µl |
| Quick Ligase | 5 µl |
| | 50 µl total |

The reaction was incubated for 15 min at room temperature, then the DNA purified on a Qiagen column, eluting in 30 µl Elution buffer (EB).

Step 6) Gel Purification
 Materials:
 Ligation reaction (from Step 5)
 Agarose (Biorad, 161-3107)
 TAE (50×)
 Distilled water
 Ethidium bromide (Sigma, E1510)
 Loading buffer (4×) (50 mM Tris pH8, 40 mM EDTA, 40% w/v sucrose)
 Low molecular weight ladder (NEB, N3233L)
 Gel trays and tank. Electrophoresis unit
 Dark reader transilluminator (Clare Chemical Research, D195M)
 Gel extraction kit columns (Qiagen, 28704)
Procedure:
 The entire sample from the purified ligation reaction was loaded into one lane of a 2% agarose gel containing ethidium bromide and run at 120V for 60 min. The gel was then viewed on a 'White-light' box and fragments from 120 bp to 170 bp excised and purified with a gel extraction column, eluting in 30 µl elution buffer (EB).

Step 7) Exonuclease I Treatment of PCR Primers
 Materials:
 Exonuclease I (E. coli) (20 U/ul) (NEB, M0293S)
 Exonuclease I Reaction Buffer (10×) (NEB, M0293S)
 Water
 DNA Primers with a phosphorothioate at the n−1 position
 P6 Bio-Rad columns (Bio-Rad, 732-6221)

Procedure:

DNA Primers with a phosphorothioate at the n−1 position (5×85 µl of each Primer (approx 25 µM)) were aliquoted into Eppendorf tubes. 10 µl of 10× Exonuclease I Reaction Buffer and 5 µl of Exonuclease I was added to each tube. Each Eppendorf tube was placed in a rack and stored in an oven set at 37° C. for 16 hours. After 16 hr, the tubes were placed on a hotblock set at 80° C. for 2 minutes. Subsequently, the solutions from the Eppendorfs were passed through P6 Bio-Rad columns and spun in a centrifuge at 2000 rpm for 2 minutes. An extra 20 µl of $H_2O$ was added to the columns and the columns respun. The filtered solutions were placed into a SpeedVac® and evaporated until each was at 20 µl, and the fractions combined. The pooled fractions were injected into a reverse phase HPLC system, and the main peak was collected. The collected fractions were evaporated to dryness in a SpeedVac®, 50 µl of water was added and the fraction was subjected again to evaporation to dryness. The resulting pellets were dissolved in 50 µl of water, pooled and a UV measurement taken to determine the concentration of the oligonucleotide.

Step 8) PCR

Materials:
Gel purified DNA (from Step 6)
Water
Phusion master mix (2×) (NEB, F-531L)
Exonuclease treated universal PCR primer 1 (25 uM): 5' AATGATACGGCGACCACCGAGATCTA-CACTCTTTCCCTACACGACGCTCTTCCGA TC×T 3' (SEQ ID NO:27), where x=phosphorothioate bond (from Step 7)
Exonuclease treated universal PCR primer 2 (25 uM): 5' CAAGCAGAAGACGGCATACGAGATCG-GTCTCGGCATTCCTGCTGAACCGCTCTTC CGATC×T (SEQ ID NO:9), where x=phosphorothioate bond (from Step 7)
PCR machine
PCR purification kit columns (Qiagen, #28104)

Procedure:
The PCR reaction was prepared as follows:

| | | |
|---|---|---|
| Gel purified BAC DNA | 1 µl | |
| Phusion mastermix | 25 µl | |
| Universal PCR primer 1 | 1 µl | |
| Universal PCR primer 2 | 1 µl | |
| Water | 22 µl | |
| | 50 µl | total |

Thermocycling was carried out in a PCR machine under the following conditions:
30 secs @ 98° C.
[10 sec@ 98° C., 30 sec @ 65° C., 30 sec @ 72° C.] 18 cycles
5 min @ 72° C.
Hold @ 4° C.

PCR products were purified on a Qiagen column, eluting in 30 µl EB. The resulting DNA libraries were ready for amplification on a surface amplification platform.

Validation of Libraries by Conventional Sanger Sequencing

Four (4) µl of the libraries were cloned into a plasmid vector (Zero Blunt TOPO PCR cloning kit, Invitrogen #K2800-20) and plated out on agar, according to the manufacturer's instructions. Colonies were picked, mini-prepped and the cloned fragments sequenced by conventional Sanger sequencing.

16 Clones from BAC Library

1(204 bp) Insert: E. coli 85 bp
(SEQ ID NO: 10)
AATGATACGGCGACCACCGAGATCTACACTCTTTCCCTACACGAC
GCTCTTCCGATCTACTGATTTCATTGCAGCCAAAGGCAAACTTTG
GCTGCATCGTTTTACAGTCGCCATAAGCCTTTCCTCTGTTAAACC
GCCTTCTGAGATCGGAAGAGCGGTTCAGCAGGAATGCCGAGACCG
ATCTCGTATGCCGTCTTCTGCTTG 2(214 bp) Insert: BAC 95 bp
(SEQ ID NO: 11)
AATGATACGGCGACCACCGAGATCTACACTCTTTCCCTACACGAC
GCTCTTCCGATCTATCAATATTGTGAAAATGACCATACTGCCAAA
AAAAAACTACAAATTCAATGCAATTTTCATCAAAATACCATCATC
ATTCTTCACAATATTGATAGATCGGAAGAGCGGTTCAGCAGGAAT
GCCGAGACCGATCTCGTATGCCGTCTTCTGCTTG 3(215 bp) Insert: BAC 96 bp
(SEQ ID NO: 13)
AATGATACGGCGACCACCGAGATCTACACTCTTTCCCTACACGAC
GCTCTTCCGATCTCTCACTCCTGGCAGAGGGACGTGTGACTAGCC
ATGGGCCCCTAGGTCTCCAGTTCCTGGGTAGCTTGTATTTTTGAA
CATCTCCTGTATATTAGTTAGATCGGAAGAGCGGTTCAGCAGGAA
TGCCGAGACCGATCTCGTATGCCGTCTTCTGCTTG 4 (147 bp) Insert: BAC 28 bp
(SEQ ID NO: 14)
AATGATACGGCGACCACCGAGATCTACACTCTTTCCCTACACGAC
GCTCTTCCGATCTAGTGTAGTTGAGATCTGCCTTAGCAGCAAGAT
CGGAAGAGCGGTTCAGCAGGAATGCCGAGACCGATCTCGTATGCC
GTCTTCTGCTTG 5 (183 bp) Insert: BAC 64 bp
(SEQ ID NO: 15)
AATGATACGGCGACCACCGAGATCTACACTCTTTCCCTACACGAC
GCTCTTCCGATCTAACACATTTCAAAGTTTGGGGCCCTCCTCCTC
CCCAAAAAACAAACCACAAAAAACAAACAAAAAGATCGGAAGAGC
GGTTCAGCAGGAATGCCGAGACCGATCTCGTATGCCGTCTTCTGC
TTG 6 (170 bp) Insert: BAC 59 bp
(SEQ ID NO: 16)
GGCGACCACCGAGATCTACACTCTTTCCCTACACGACGCTCTTCC
GATCTGAATGCCTTTTATAGCATTTAATTTTTCCTAAGTATAATT
ACCAAATAAAAATTGTATAAGATCGGAAGAGCGGTTCAGCAGGAA
TGCCGAGACCGATCTCGTATGCCGTCTTCTGCTTG 7 (180 bp) Insert: BAC 61 bp
(SEQ ID NO: 17)
AATGATACGGCGACCACCGAGATCTACACTCTTTCCCTACACGAC
GCTCTTCCGATCTTGGGCCCGGGAGGAGTTTGCCGGGGAGGAGTG
GGTTTGGAATCGGGGTTAAAGGAAAGAGAAGATCGGAAGAGCGGT
TCAGCAGGAATGCCGAGACCGATCTCGTATGCCGTCTTCTGCTTG 8 (190 bp) Insert: BAC 73 bp
(SEQ ID NO: 18)
TGATACGGCGACCACCGAGATCTACACTCTTTCCCTACACGACGC
TCTTCCGATCTAAGATCTATTTCAAATGGACTGTAGATCTAAGTA
TAAAAGGTAAGAGAATAATTATTCTAGAAAGTAAATGTAAGATCG
GAAGAGCGGTTCAGCAGGAATGCCGAGACCGATCTCGTATGCCGT
CTTCTGCTTG 9 (192 bp) Insert: BAC 74 bp
(SEQ ID NO: 19)
AATGATACGGCGACCACCAGATCTACACTCTTTCCCTACACGACG
CTCTTCCGATCTGGGAGGCCAAGGTGGGTGGATCACCTGAGATCA
GGAGTTCGAGACCAGCTGGCCAACATGATGAAACTCTGTCTAGAT
CGGAAGAGCGGTTCAGCAGGAATGCCGAGACCGATCTCGTATGCC
GTCTTCTGCTTG 10 (185 bp) Insert: BAC 66 bp
(SEQ ID NO: 20)
AATGATACGGCGACCACCGAGATCTACACTCTTTCCCTACACGAC
GCTCTTCCGATCTTGACCATTGTAACCATTAATGTAGACTGCAAT
GATATGCACTATTTACAACCTTTTTTAAGACTCTAGATCGGAAGA
GCGGTTCAGCAGGAATGCCGAGACCGATCTCGTATGCCGTCTTCT
GCTTG -continued 11 (199 bp) Insert: BAC 80 bp
(SEQ ID NO: 21)
AATGATACGGCGACCACCGAGATCTACACTCTTTCCCTACACGAC
GCTCTTCCGATCTCTTTGAAGAGCTGGCAGTAGAAGATAAACAGG
CTGGGGAAGAAGAGAAAGTGCTCAAGGAGAAGGAGCAGCAGCAGC
AGCAGATCGGAAGAGCGGTTCAGCAGGAATGCCGAGACCGATCTC
GTATGCCGTCTTCTGCTTG 12 (212 bp) Insert: BAC 93 bp
(SEQ ID NO: 22)
AATGATACGGCGACCACCGAGATCTACACTCTTTCCCTACACGAC
GCTCTTCCGATCTAGTATTCAACAAGTCTGTCTTTTCCAAGTGTC
TTTAAAGACCAGAAATACCTGTTTTTAACACACAGGGTTGCAAAA
TTCAGAGGAGATTGGCAGATCGGAAGAGCGGTTCAGCAGGAATGC
CGAGACCGATCTCGTATGCCGTCTTCTGCTTG 13 (247 bp) Insert: E. coli 128 bp
(SEQ ID NO: 23)
AATGATACGGCGACCACCGAGATCTACACTCTTTCCCTACACGAC
GCTCTTCCGATCTCTTGAGATGAGTGATGACGGCGCGCTGGAAGT
TGCTCGTCGCGCTCGCGGTACGCCGCGCATTGCCAACCGTCTGCT
GCGTCGAGTGCGTGATTTCGCCGAAGTGAAGCACGATGGCACCAT
CTCAAGAGATCGGAAGAGCGGTTCAGCAGGAATGCCGAGACCGAT
CTCGTATGCCGTCTTCTGCTTG 14 (202 bp) Insert: BAC 83 bp
(SEQ ID NO: 24)
AATGATACGGCGACCACCGAGATCTACACTCTTTCCCTACACGAC
GCTCTTCCGATCTGGGGTTGGTGGAACCCAGATGCCTCCCAGAT
TGGTGGGCCCTGTGGCACTTGTACCTGCTGTTGCTGTTGCTGCTG
CTGCTGAGATCGGAAGAGCGGTTCAGCAGGAATGCCGAGACCGAT
CTCGTATGCCGTCTTCTGCTTG 15 (166 bp) Insert: BAC 47 bp
(SEQ ID NO: 25)
AATGATACGGCGACCACCGAGATCTACACTCTTTCCCTACACGAC
GCTCTTCCGATCTATGATAAGGAGCAGGTTTACAGATCATAAGTG
CAAAAGCGGGCGAGAAGATCGGAAGAGCGGTTCAGCAGGAATGCC
GAGACCGATCTCGTATGCCGTCTTCTGCTTG 16 (147 bp) Insert: BAC 31 bp
(SEQ ID NO: 26)
GATACGGCGACCACCGAGATCTACACTCTTTCCCTACACGACGCT
CTTCCGATCTCTGATACTGTTGTAACCACCCAATTGGTTCAAGAT
CGGAAGAGCGGTTCAGCAGGAATGCCGAGACCGATCTCGTATGCC
GTCTTCTGCTTG These results confirm that the library preparation method produces a library of 'sequenceable' DNA templates. Each library contained a plurality of genomic inserts, each of which was flanked by the two adaptors (AATGATACGGCGAC-CACCGAGATCTACACTCTTTCCCTACAC-GACGCTCTTCCGATCT (SEQ ID NO:27) and AGATCG-GAAGAGCGGTTCAGCAGGAATGCCGAGACCGATCT CGTATGCCGTCTTCTGCTT G (SEQ ID NO:28)), required for cluster formation and SBS sequencing. The insert DNA from each of the libraries aligned to the BAC reference, with a small amount of E. coli contamination.

Clusters were prepared from the above library as described in examples 1-5 above.

The primers grafted to the surface had the following sequence:

P5diol:
(SEQ ID NO: 1)
5' PS-TTTTTTTTTT-diol-AATGATACGGCGACCACCGA

P7-TU:
(SEQ ID NO: 29)
5'TTTTTTTTTUCAAGCAGAAGACGGCATACGA-OH

P5-phosphate:
(SEQ ID NO: 30)
5' PS-TTTTTTTTTTAATGATACGGCGACCACCGA-PO4

The three primers were mixed at a 1:1:1 concentration, and used at 0.5 µM concentration of each primer.

The clusters were linearised using periodate treatment as described in example 10, and blocked with terminal transferase as described in example 5, step 2.

The clusters were treated to hybridise a first sequencing primer, as described above. The sequence of the sequencing primer was (SEQ ID NO: 6)
5'-ACACTCTTTCCCTACACGACGCTCTTCCGATC To denature the nucleic acid within the clusters and to hybridize the sequencing primer, the following reagents are flowed through the cell as shown in Table 4:

| Step | Description | T (° C.) | Time (sec) | Flow rate (µL/min) | Pumped V (µL) |
|---|---|---|---|---|---|
| 1 | Pump 0.1M NaOH | 20 | 300 | 15 | 75 |
| 2 | Pump TE | 20 | 300 | 15 | 75 |
| 3 | Pump Primer mix | 20 | 300 | 15 | 75 |
| 4 | Hold at 60 C. | 60 | 900 | 0 | 0 |
| 5 | Pump wash buffer | 40.2 | 300 | 15 | 75 |

Sequencing from the target fragment was performed using reagents and methods described above in example 7.

Example 12a

Obtaining a Second Read

Step 1: Deblocking the Phosphate Groups with T4 Polynucleotide Kinase

The clusters were treated as follows: Flow 1× Exchange reaction buffer (50 mM Imidazole-HCl pH 6.4; 12 mM $MgCl_2$; 1 mM 2-mercaptoethanol; 70 µM ADP) at 15 µL/channel/min for 5 mins at 20° C. This was followed by PNK solution (0.2 U/µL of PNK in 1× exchange reaction buffer) at 15 µL/channel/min for 5 mins at 20° C. The flow cell was heated to 38° C. for 30 mins and allowed to cool. The channels were washed with wash buffer for 5 minutes, then 5×SSC for 5 minutes.

Step 2: Resynthesis of Clusters.

The clusters were treated to 15 cycles of isothermal amplification as described in example 5; step 1

Step 3: Linearisation with USER

The clusters were treated as described in example 6 to cleave the uracil moiety in the P7 primer. The clusters were blocked with terminal transferase as described in example 5, step 2.

The clusters were treated to hybridise a first sequencing primer, as described above. The sequence of the sequencing primer was (SEQ ID NO: 31)
5'-CGGTCTCGGCATTCCTGCTGAACCGCTCTTCCGATC To denature the nucleic acid within the clusters and to hybridize the sequencing primer, the following reagents are flowed through the cell as shown in Table 4:

| Step | Description | T (° C.) | Time (sec) | Flow rate (µL/min) | Pumped V (µL) |
|---|---|---|---|---|---|
| 1 | Pump 0.1M NaOH | 20 | 300 | 15 | 75 |
| 2 | Pump TE | 20 | 300 | 15 | 75 |
| 3 | Pump Primer mix | 20 | 300 | 15 | 75 |

-continued

| Step | Description | T (° C.) | Time (sec) | Flow rate (μl/min) | Pumped V (μl) |
|---|---|---|---|---|---|
| 4 | Hold at 60 C. | 60 | 900 | 0 | 0 |
| 5 | Pump wash buffer | 40.2 | 300 | 15 | 75 |

Sequencing from the target fragment was performed using reagents and methods described above in example 7.

The data obtained from the first and second reads is shown in FIG. 8. Both reads clearly align against the BAC sequence, with only 4% of the reads deriving from the E. coli that contaminated the original sample. The average fragment size of the inserts was 80 base pairs, so for the two 25 base pair reads, the distance between the ends of the reads was 30 base pairs on average. The majority of the clusters from the first read (8208/8572) (96%) also gave a good read for the second read.

Example 13

Preparation and Paired End Sequencing Using Two Immobilised Primers Modified with Uracil and 8-oxo G Respectively Step 1) Grafting Primers onto Surface of SFA Coated Chip An SFA coated chip is placed onto a modified MJ-Research thermocycler and attached to a peristaltic pump. Grafting mix consisting of 0.5 μM of a forward primer and 0.5 μM of a reverse primer in 10 mM phosphate buffer (pH 7.0) is pumped into the channels of the chip at a flow rate of 60 μl/minutes for 75 s at 20° C. The thermocycler is then heated to 51.6° C., and the chip is incubated at this temperature for 1 hour. During this time, the grafting mix undergoes 18 cycles of pumping: grafting mix is pumped in at 15 μl/minutes for 20 s, then the solution is pumped back and forth (5 s forward at 15 μl/minutes, then 5 s backward at 15 μl/minutes) for 180 s. After 18 cycles of pumping, the chip is washed by pumping in 5xSSC/5 mM EDTA at 15 μl/minutes for 300 s at 51.6° C. The thermocycler is then cooled to 20° C.

The primers are typically 5'-phosphorothioate oligonucleotides incorporating any specific sequences or modifications required for cleavage. Their sequences and suppliers vary according to the experiment for which they are to be used, and in this case were complementary to the 5'-ends of the template duplex. The DNA sequence used in this process was the pool of the two libraries, which have ends complementary to the grafted primers. The library mix was denatured using sodium hydroxide treatment followed by snap dilution as described.

For some of the experiments detailed, the amplified clusters contained a diol linkage in one of the grafted primers. Diol linkages can be introduced by including a suitable linkage into one of the primers used for solid-phase amplification. Synthesis of the diol phosphoramidite is described in Example 4 below. Products containing such diol linkages can be cleaved using periodate and propanolamine as described, and the resulting single stranded polynucleotides hybridised as described.

The grafted primers contain a sequence of T bases at the 5'-end to act as a spacer group to aid linearisation and hybridization. The sequences of the three primers grafted to the chip are as follows:

Oligo A:
(SEQ ID NO: 32)
5'-PS-TTTTTTTTTTAATGATACGGCGACCACCGAUCTACAC-3'
where U = 2-deoxyuridine;

Oligo B:
(SEQ ID NO: 33)
5'-PS-TTTTTTTTTTCAAGCAGAAGACGGCATACGAGoxoAT-3',
where Goxo = 8-oxoguanine).

Step 2) Preparation of Clusters by Isothermal Amplification:

The DNA sequence used in the amplification process is the mixture of the two libraries prepared in Example 1, which have ends complementary to the grafted primers. The duplex DNA (1 nM) is denatured using 0.1 M sodium hydroxide treatment followed by snap dilution to the desired 0.2-2 pM 'working concentration' in 'hybridization buffer' (5xSSC/0.1% Tween).

Surface amplification was carried out by isothermal amplification using a commercially available Solexa/Illumina cluster station as described in PCT/US/2007/014649. The cluster station is essentially a hotplate and a fluidics system for controlled delivery of reagents to a flow cell.

The single stranded template (denatured as indicated above) is hybridised to the grafted primers immediately prior to the amplification reaction, which thus begins with an initial primer extension step rather than template denaturation. The hybridization procedure begins with a heating step in a stringent buffer to ensure complete denaturation prior to hybridisation. After the hybridization, which occurs during a 20 minute slow cooling step, the flowcell was washed for 5 minutes with a wash buffer (0.3xSSC/0.1% Tween).

During template hybridization and first extension, a number of solutions/buffers are typically employed, e.g., a solution comprising the DNA samples, a hybridization buffer (5xSSC/0.1% tween), a wash buffer (0.3xSSC/0.1% tween), a 2M sodium hydroxide solution, a cluster buffer (200 mM Tris, 100 mM Ammonium Sulfate, 20 mM Magnesium sulfate, 1% Triton, 1.3% DMSO, pH 8.8); an amplification additive (5 M betaine), DNA polymerase, and 10 mM dNTP mix.

To prepare the hybridization mixes, a 0.2 ml strip sample tube and the hybridization buffer are pre-chilled. Using 1.7 ml Eppendorf tube(s), the DNA template(s) are then diluted to 1 nM in buffer EB (Qiagen). 1 μL of 2 M NaOH is added to 19 μL of template, vortexed briefly and incubated for 5 minutes at room temperature to denature the DNA template into single strands. The denatured DNA is diluted to working concentration (0.2-2 pM) in pre-chilled hybridization buffer (e.g. for 1 mL of 1 pM Hybridization mix, 1 μL of denatured DNA is diluted into 1 mL of pre-chilled hybridization buffer). The volume required depends on the number of channels used—at least 120 μL of hybridization mix per channel is optionally used. Thus, 1 mL of hybridization mix is enough for 8 channels. The samples are vortexed briefly, spun down and aliquoted into the pre-chilled 0.2 ml strip tubes (with no bubbles in the bottom of the tubes) and used immediately.

To prepare the Amplification pre-mix (of sufficient volume for the first extension and 35 cycles of isothermal amplification), 35 mL of H$_2$O (milliQ), 7 mL of Cluster buffer (200 mM Tris, 100 mM Ammonium Sulfate, 20 mM Magnesium sulfate, 1% Triton, 1.3% DMSO, pH 8.8), and 28 mL of Amplification additive (5 M betaine solution) are mixed to achieve a final volume of 70 mL.

To prepare the first extension Taq mix, 780 μL of Amplification pre-mix, 16 μL of 10 mM dNTPs, and 4 μL of Taq DNA polymerase are mixed together for a final volume of 800 μl.

A typical amplification process is detailed in the following table (Table 1), detailing the flow volumes per channel, controlled automatically by the computer component of the invention.

TABLE 1

Template hybridization and first extension.

| Step | Description | T (° C.) | Time (sec) | Flow rate (μl/min) | Pumped V (μl) |
|---|---|---|---|---|---|
| 1 | Pump Hybridization pre-mix | 20 | 120 | 60 | 120 |
| 2 | Pump Hybridization mix | 96 | 300 | 15 | 75 |
| 3 | Remove bubbles | 96 | 6 | 100 | 10 |
| 4 | Stop flow and hold T | 96 | 30 | static | 0 |
| 5 | Slow cooling | 96-40 | 1120 | static | 0 |
| 6 | Pump wash buffer | 40 | 300 | 15 | 75 |
| 7 | Pump amplification pre-mix | 40 | 280 | 15 | 70 |
| 8 | Pump amplification mix | 40 | 95 | 60 | 95 |
| 9 | First Extension | 74 | 90 | static | 0 |
| 10 | cool to room temperature | 20 | 0 | static | 0 |

Isothermal Amplification at 60° C. Using Formamide as Denaturant

The copied DNA can be isothermally amplified into clusters at 60° C. using formamide as a denaturant. The isothermal amplification (including both temperature control and reagent control) is overseen by the computer component. Table 2 gives outlines of exemplary script controls. After the isothermal amplification, and optional washing step occur, the nucleic acid of the clusters is ready to be linearized (see below).

TABLE 2

Isothermal amplification

| Step | Description | T (° C.) | Time (sec) | Flow rate (μl/min) | Pumped V (μl) |
|---|---|---|---|---|---|
| (1) This sequence 35 times | Pump Formamide | 60 | 56 | 30 | 28 |
| | Pump Amplification pre-mix | 60 | 56 | 30 | 28 |
| | Pump Bst mix | 60 | 72 | 30 | 36 |
| 2 | Pump wash buffer | 60 | 280 | 30 | 140 |
| 3 | Pump Storage Buffer | 20 | 380 | 15 | 95 |

Wash buffer=0.3×SSC/0.1% Tween
Amplification pre mix=2 M betaine, 20 mM Tris, 10 mM Ammonium Sulfate, 2 mM Magnesium sulfate, 0.1% Triton, 1.3% DMSO, pH 8.8
Bst mix=2 M betaine, 20 mM Tris, 10 mM Ammonium Sulfate, 2 mM Magnesium sulfate, 0.1% Triton, 1.3% DMSO, pH 8.8 plus 200 μM dNTPs and 80 units/mL of Bst polymerase (NEB Product ref M0275L)
Storage Buffer=5×SSC.

Step 3) Preparation of Clusters for First Sequencing Read

The preparation for read one was performed on the Illumina cluster station. All volumes used in the protocol were 95 ul per lane unless otherwise stated. Linearisation of A-type surface immobilised oligonucleotides was achieved by incubation with USER enzyme mix (cocktail of Uracil DNA Glycosylase and Endonuclease VIII, NEB #M5505, 10 U/ml, 10 mM KCl, 20 mM Tris pH 8.8, 10 mM (HN4)2SO4, 2 mM MgSO4, 0.1% Triton X-100, 37° C., 30 minutes). All exposed 3'-OH termini of DNA, either from the extended template or unextended surface oligonucleotides were blocked by dideoxy chain termination using a cocktail of terminal transferase (0.25 U/μl) and a modified polymerase (SBS polymerase as described below) (0.015 mg/ml, 100 μM ddNTP, 50 mM tris, 50 mM NaCl, 6 mM MgSO4, 1 mM EDTA, 0.05% Tween 20). Blocking was achieved in a two stage protocol, initial incubation at 37° C. for 30 minutes followed by a ramping to 60° C. and incubating the flowcell for a further 15 minutes). Linearised and blocked clusters were washed with 0.3×SSC and storage buffer prior to denaturation with 0.1N NaOH. Denatured clusters were neutralised with TE buffer (10 mM Tris pH 8.0, 1 mM EDTA) and washed with storage buffer. The read 1 specific sequencing primer (5'-ACACTCTTTCCCTACACGACGCTCTTCCGATC-3', 0.5 μM in hybridisation buffer) was annealed to the clusters by incubation at 60° C. for 15 minutes, followed by a 0.3×SSC wash at 40° C. (ramp rate 1° C./sec). The flowcell was finally flushed with storage buffer (at 20° C.). Processed flowcells were transferred to the Illumina Genome Analyser for sequencing read 1.

Step 4) Sequencing from the Target Fragment

Sequencing of the clusters from the above illustrative protocol was carried out using modified nucleotides prepared as described in International patent application WO 2004/018493, and labeled with four spectrally distinct fluorophores, as described in PCT application number PCT/GB2007/001770. Sequencing of clusters is described in more detail in patent WO06064199. The contents of the above-listed three documents are incorporated herein by reference in their entireties.

A mutant 9° N polymerase enzyme (an exo-variant including the triple mutation L408Y/Y409A/P410V and C223S) (SBS polymerase) was used for the nucleotide incorporation steps.

All processes were conducted as described in the Illumina Genome Analyser operating manual. The flowcell was mounted to the analyser, primed with sequencing reagents: position #1=incorporation mix (1 μM dNTP mix, 0.015 μg/ml SBS polymerase, 50 mM Tris pH 9.0, 50 mM NaCl, 6 mM MgSO4, 1 mM EDTA, 0.05% Tween 20); position #2=spare (MilliQ water only); position #3=scan mix (100 mM Tris pH 7.0, 50 mM sodium acsorbate); position #4=High salt wash (5×SSC, 0.05% Tween 20); position #5=incorporation buffer (50 mM Tris pH 9.0, 50 mM NaCl, 1 mM EDTA, 0.05% Tween 20); position #6=cleavage mix (100 mM TCEP, 100 mM Tris pH 9.0, 100 mM NaCl, 50 mM sodium ascorbate, 0.05% Tween 20); position #7=cleavage buffer (100 mM Tris pH 9.0, 100 mM NaCl, 0.05% Tween 20); position #8=spare (single reads) or connected to PE module outlet (paired read experiments). Flowcells were sequenced using standard sequencing recipes for either 27- or 37-cycle experiments. Data was analysed using the standard analysis pipeline.

Incorporation: Prime with Incorporation buffer, 125 μL/channel; 60 μL/minutes, Heat to 60° C.
Treat with Incorporation mix, 75 μL/channel; 60 μL/minutes. Wait for a total of 15 minutes in addition to pumping fresh Incorporation mix, 25 μL/channel; 60 μL/minutes, every 4 minutes.
Cool to 20° C.
Wash with Incorporation buffer, 75 μL/channel; 60 μL/minutes.
Wash with 5×SSC/0.05% Tween 20, 75 μL/channel; 60 μL/minutes
Prime with imaging buffer, 100 μL/channel; 60 μL/minutes
Scan in 4 colors at RT.

Cleavage: Prime with Cleavage buffer (0.1M Tris pH 7.4, 0.1M NaCl and 0.05% Tween 20), 125 μL/channel; 60 μL/minutes.
Heat to 60° C.
Treat the clusters with Cleavage mix (100 mM TCEP in Cleavage buffer), 75 μL/channel; 60 μL/minutes.
Wait for a total of 15 minutes in addition to pumping fresh cleavage mix, 25 μL/channel; 60 μL/minutes, every 4 minutes.

Cool to 20° C.
Wash with Enzymology buffer.
Wash with 5×SSC/0.05% Tween 20.
Repeat the process of Incorporation and Cleavage for as many cycles as required.

Incorporated nucleotides were detected using the Illumina genome analyzer, a Total Internal Reflection based fluorescent CCD imaging apparatus described in "Systems and Devices for Sequence by Synthesis Analysis," U.S. Ser. No. 60/788,248, filed Mar. 31, 2006 and corresponding PCT application PCT/US07/07991 filed Mar. 30, 2007.

Step 5) Preparation of the Clusters for the Second Read

Following the successful completion sequencing of read 1 on the Genome Analyser, flowcells remained mounted and were prepared for read 2 in situ, using the Illumina Paired End module. Temperature control was achieved by using the Genome Analyser peltier. All flow rates were 60 µL/min and 75 µl per lane unless otherwise stated. Clusters were denatured with 0.1 M NaOH to remove the extended sequencing primer from read 1. Clusters were 3'-dephosphorylated using T4 polynucleotide kinase (Invitrogen #18004-010, 200 U/ml, 50 mM imidazole pH 6.4, 12 mM MgCl$_2$, 70 µM ADP, 1 mM 2-mercaptoethanol, 37° C., 30 minutes), prior to re-synthesis of the A-strand achieved using 15 cycles of 60° C. isothermal amplification (same reagents and conditions as described for cluster creation except conducted at 30 µl/min). Clusters were washed before and after resynthesis with 0.3×SSC (150 µl and 245 µl respectively). Linearisation of the B-strand of the re-synthesised clusters was achieved by the excision of 8-oxoguanine from the B-type oligo using Fpg (formamidopyrimidine DNA glycosylase, NEB #M0240, 80 U/ml, 10 mM Bis Tris propane pH 7.0, 10 mM MgCl$_2$, 1 mM dithiothreitol, 37° C., 30 minutes). Blocking was performed as described for read 1 using the same blocking cocktail. Linearised and blocked clusters were denatured prior to hybridisation of the read 2 specific sequencing primer (5'-CGGTCTCGGCAT-TCCTGCTGAACCGCTCTTCCGATC-3' (SEQ ID NO: 31), 0.5 µM in hybridisation buffer) as described for read 1. Read 2 of the processed flowcells was subsequently sequenced on the Illumina Genome Analyser.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method for sequencing of first and second regions of target polynucleotides having different sequences, the method comprising:
   (a) providing beads comprising immobilized first strands of the target polynucleotides;
   (b) hybridizing a sequencing primer in solution to the immobilized first strands and sequencing the first region of the first strands of the of the target polynucleotides, wherein the sequencing comprises extension of a sequencing primer by sequential additions of nucleotides to generate an extended sequencing primer;
   (c) copying at least a portion of the first strands of the target polynucleotides by further extending the extended sequencing primer, thereby generating second strands having the second regions of the target polynucleotides;
   (d) removing a portion of the first strands from the beads, thereby generating an immobilized extension primer having a free 3'-hydroxyl; and
   (e) sequencing the second region of the second strands of the target polynucleotides using the immobilized extension primer, wherein determining the sequence of the first and second regions of the target polynucleotides achieves sequencing of the first and second regions of the target polynucleotides.

2. The method of claim 1, wherein the removal is carried out by nicking the first strands followed by digesting the first strands.

3. The method of claim 1, wherein the target polynucleotides further comprise a tag.

4. The method of claim 3, further comprising sequencing the tag.

5. The method of claim 4, wherein the tag is sequenced after step (b).

6. The method of claim 1, wherein the first and second regions are located at the ends of the target polynucleotides.

7. The method of claim 1, wherein the sequencing comprises extension of a sequencing primer by sequential addition of labeled nucleotides.

8. The method of claim 7, wherein the nature of the nucleotide added is determined after each of the sequential additions.

9. The method of claim 1, wherein the first strands comprise a cleavage site that allows for controlled cleavage of the first strands.

10. The method of claim 1, wherein the sequencing is carried out by pyrosequencing.

11. The method of claim 1, wherein the sequencing is carried out by sequencing-by-synthesis.

12. The method of claim 1, wherein step (a) comprises providing beads comprising immobilized single-stranded first strands of the target polynucleotides.

13. The method of claim 1, wherein the beads are in wells.

14. The method of claim 1, wherein the different target polynucleotides have the same universal primer recognition regions.

15. The method of claim 14, wherein the sequencing primer in solution comprises a universal primer that is hybridized to the universal primer recognition regions of the target polynucleotides in step (b).

16. The method of claim 14, wherein the immobilized extension primer comprises a universal primer that is hybridized to the universal primer recognition regions of the target polynucleotides in step (e).

\* \* \* \* \*